US012758558B2

(12) United States Patent
Campbell et al.

(10) Patent No.: US 12,758,558 B2
(45) **Date of Patent: *Oct. 13, 2026**

(54) METHODS OF TREATING SOLID TUMORS WITH CCR2 ANTAGONISTS

(71) Applicants: CHEMOCENTRYX, INC., Thousand Oaks, CA (US); THE REGENTS OF THE UNIVERSITY OF CALIFORNIA, Oakland, CA (US)

(72) Inventors: James J. Campbell, San Jose, CA (US); Rajinder Singh, Belmont, CA (US); Samuel Hwang, Oakland, CA (US); Xuesong Wu, Oakland, CA (US)

(73) Assignees: CHEMOCENTRYX, INC., Thousand Oaks, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 916 days.

This patent is subject to a terminal disclaimer.

(21) Appl. No.: 17/481,829

(22) Filed: Sep. 22, 2021

(65) Prior Publication Data

US 2022/0241290 A1 Aug. 4, 2022

Related U.S. Application Data

(63) Continuation of application No. 16/241,391, filed on Jan. 7, 2019, now Pat. No. 11,154,556.

(60) Provisional application No. 62/614,923, filed on Jan. 8, 2018.

(51) Int. Cl.

| | |
|---|---|
| ***A61K 31/536*** | (2006.01) |
| ***A61K 31/4433*** | (2006.01) |
| ***A61K 31/453*** | (2006.01) |
| ***A61K 45/06*** | (2006.01) |
| ***A61P 35/00*** | (2006.01) |

(52) U.S. Cl.

CPC ........ *A61K 31/536* (2013.01); *A61K 31/4433* (2013.01); *A61K 31/453* (2013.01); *A61K 45/06* (2013.01); *A61P 35/00* (2018.01)

(58) Field of Classification Search

CPC .............. A61K 31/536; A61K 31/4433; A61K 31/453; A61K 45/06; A61P 35/00

See application file for complete search history.

(56) References Cited

U.S. PATENT DOCUMENTS

| | | | | |
|---|---|---|---|---|
| 6,949,546 | B2 | 9/2005 | Ko et al. | |
| 8,168,757 | B2 | 5/2012 | Finnefrock et al. | |
| 8,354,509 | B2 | 1/2013 | Carven et al. | |
| 8,519,135 | B2 | 8/2013 | Chen | |
| 8,546,408 | B2 | 10/2013 | Krasinski | |
| 8,552,154 | B2 | 10/2013 | Freeman et al. | |
| 8,629,133 | B2 | 1/2014 | Sugimoto | |
| 8,741,295 | B2 | 6/2014 | Olive | |
| 9,212,224 | B2 | 12/2015 | Cogswell et al. | |
| 9,783,540 | B2 | 10/2017 | Fan et al. | |
| 10,251,888 | B2 | 4/2019 | Bekker | |
| 10,398,685 | B2 | 9/2019 | Bekker | |
| 10,583,131 | B2 | 3/2020 | Bekker | |
| 11,154,556 | B2 | 10/2021 | Campbell et al. | |
| 11,304,952 | B2 * | 4/2022 | Campbell | A61P 35/00 |
| 11,986,466 | B2 | 5/2024 | Campbell et al. | |

(Continued)

FOREIGN PATENT DOCUMENTS

| | | | |
|---|---|---|---|
| EA | 014960 | B1 | 4/2011 |
| JP | 2013-526507 | A | 6/2013 |

(Continued)

OTHER PUBLICATIONS

Wu, Xuesong, Ryan E. Sells, and Sam T. Hwang. "Upregulation of inflammatory cytokines and oncogenic signal pathways preceding tumor formation in a murine model of T-cell lymphoma in skin." Journal of Investigative Dermatology 131, No. 8 (2011): 1727-1734) (Year: 2011).*

Golay, Josee, and Martino Introna. "Chemokines and antagonists in non-Hodgkin's lymphoma." Expert Opinion on Therapeutic Targets 12, No. 5 (2008): 621-635) (Year: 2008).*

Theurich, Sebastian, Max Schlaak, Harold Steguweit, Lukas C. Heukamp, Kerstin Wennhold, Peter Kurschat, Anja Rabenhorst et al. "Targeting tumor-infiltrating B cells in cutaneous T-cell lymphoma." Journal of Clinical Oncology 34, No. 12 (2016): e110-e116 (Year: 2016).*

(Continued)

*Primary Examiner* — James H Alstrum-Acevedo
*Assistant Examiner* — Carolyn L. Ladd
(74) *Attorney, Agent, or Firm* — Mintz Levin Cohn Ferris Glovsky and Popeo PC

(57) ABSTRACT

The present disclosure provides, inter alia, methods of treating a solid-tumor by administering an effective amount of a Chemokine Receptor 2 (CCR2) antagonist. Also provided herein are methods of reducing the number of macrophages in a solid tumor microenvironment, the method comprising administering effective amount of a Chemokine Receptor 2 (CCR2) antagonist. In an additional aspect, the current disclosure further provides methods of increasing the number CD8+ T cells in a solid tumor microenvironment, the method comprising administering effective amount of a Chemokine Receptor 2 (CCR2) antagonist. In some embodiments, the CCR2 antagonist has the formula I:

(I)

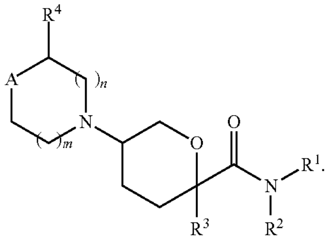

18 Claims, 19 Drawing Sheets

(56) References Cited

U.S. PATENT DOCUMENTS

| | | | |
|---|---|---|---|
| 2006/0030582 | A1 | 2/2006 | DeMartino et al. |
| 2010/0144695 | A1 | 6/2010 | Zhang et al. |
| 2011/0312936 | A1 | 12/2011 | Lanter et al. |
| 2012/0004252 | A1 | 1/2012 | Ebel et al. |
| 2012/0040960 | A1 | 2/2012 | Zhang et al. |
| 2013/0123241 | A1 | 5/2013 | Ebel et al. |
| 2013/0344070 | A1 | 12/2013 | Huang et al. |
| 2014/0294898 | A1 | 10/2014 | Miller et al. |
| 2014/0341917 | A1 | 11/2014 | Nastri et al. |
| 2015/0203580 | A1 | 7/2015 | Papadopoulos et al. |
| 2015/0320859 | A1 | 11/2015 | Maecker et al. |
| 2016/0194307 | A1 | 7/2016 | Chupak et al. |
| 2016/0222060 | A1 | 8/2016 | Miller et al. |
| 2017/0216301 | A1 | 8/2017 | Quinn et al. |
| 2017/0368043 | A1 | 12/2017 | Bekker |
| 2019/0269664 | A1 | 9/2019 | Campbell et al. |
| 2019/0275015 | A1 | 9/2019 | Campbell et al. |
| 2020/0121688 | A1 | 4/2020 | Fan et al. |
| 2020/0179359 | A1 | 6/2020 | Bekker |
| 2020/0297708 | A1 | 9/2020 | Harrison et al. |
| 2021/0346361 | A1 | 11/2021 | Campbell et al. |
| 2022/0153733 | A1 | 5/2022 | Fan et al. |
| 2023/0023075 | A1 | 1/2023 | Campbell et al. |

FOREIGN PATENT DOCUMENTS

| | | | | |
|---|---|---|---|---|
| JP | 2013-528657 | A | 7/2013 | |
| WO | 02/13824 | A1 | 2/2002 | |
| WO | 03/004487 | A1 | 1/2003 | |
| WO | 03/092586 | A2 | 11/2003 | |
| WO | 03/093231 | A2 | 11/2003 | |
| WO | 03/093266 | A1 | 11/2003 | |
| WO | 2004/041777 | A2 | 5/2004 | |
| WO | 2004/076411 | A2 | 9/2004 | |
| WO | 2004/082682 | A1 | 9/2004 | |
| WO | 2004/092124 | A2 | 10/2004 | |
| WO | 2004/094371 | A2 | 11/2004 | |
| WO | 2004/110376 | A2 | 12/2004 | |
| WO | 2005/044264 | A1 | 5/2005 | |
| WO | 2005/044795 | A1 | 5/2005 | |
| WO | 2005/067502 | A2 | 7/2005 | |
| WO | 2005/080371 | A2 | 9/2005 | |
| WO | 2005/115392 | A2 | 12/2005 | |
| WO | 2006/073592 | A2 | 7/2006 | |
| WO | 2006/074265 | A2 | 7/2006 | |
| WO | 2008/014381 | A2 | 1/2008 | |
| WO | 2008/014381 | A3 | 1/2008 | |
| WO | 2010/121011 | A1 | 10/2010 | |
| WO | 2011/100227 | A1 | 8/2011 | |
| WO | 2011/159852 | A1 | 12/2011 | |
| WO | 2013/152269 | A1 | 10/2013 | |
| WO | 2014/151634 | A1 | 9/2014 | |
| WO | 2015/009856 | A2 | 1/2015 | |
| WO | 2015/026634 | A1 | 2/2015 | |
| WO | 2015/034820 | A1 | 3/2015 | |
| WO | 2015/160641 | A2 | 10/2015 | |
| WO | 2015/160641 | A3 | 10/2015 | |
| WO | 2016/039749 | A1 | 3/2016 | |
| WO | 2016/057624 | A1 | 4/2016 | |
| WO | 2016/077518 | A1 | 5/2016 | |
| WO | 2016/100285 | A1 | 6/2016 | |
| WO | 2016/100608 | A1 | 6/2016 | |
| WO | 2016/149351 | A1 | 9/2016 | |
| WO | WO-2016187393 | A1 * | 11/2016 | ........... A61K 31/453 |
| WO | 2017/165125 | A1 | 9/2017 | |
| WO | 2018/005374 | A1 | 1/2018 | |
| WO | 2018/195283 | A1 | 10/2018 | |
| WO | 2019/144098 | A1 | 7/2019 | |

OTHER PUBLICATIONS

U.S. Appl. No. 10/464,934, filed Nov. 5, 2019, Fan et al.

Extended European Search Report corresponding to EP 16797279.3 (PCT/US2016033210) dated Oct. 26, 2018; 8 pages.

International Search Report and Written Opinion corresponding to PCT/US2016/033210 mailed Aug. 16, 2016; 8 pages.

International Preliminary Report on Patentability corresponding to PCT/US2016/033210 issued Nov. 21, 2017; 6 pages.

International Search Report and Written Opinion dated Jan. 23, 2019 corresponding to PCT/US2018/052408 filed Sep. 24, 2018; 19 pages.

International Search Report and Written Opinion dated Apr. 18, 2019 corresponding to PCT/US2019/012515 filed Jan. 7, 2019.

Partial Supplementary European Search Report dated May 27, 2021 corresponding to EP Appl 18857688.8 filed Sep. 24, 2018; 19 pages.

Extended European Search Report dated Sep. 14, 2021 corresponding to EP Appl 18857688.8 filed Sep. 24, 2018; 19 pages.

Ahmadzadeh, Mojgan et al., "Tumor antigen-specific CD8 T cells infiltrating the tumor express high levels of PD-1 and are functionally impaired," *Blood* (Aug. 20, 2009); 114(8):1537-1544.

Bonapace, L. et al., "Cessation of CCL2 inhibition accelerates breast cancer metastasis by promoting angiogenesis," *Nature* (Nov. 6, 2014); 515(7525):130-133; Abstract only.

Broggi, Achille et al., "Preparation of Single-cell Suspensions for Cytofluorimetric Analysis from Different Mouse Skin Regions," *Journal of Visualized Experiments* (Apr. 20, 2016); 110:e52589; 6 pages.

Butora, Gabor et al., "3-Amino-1-alkyl-cyclopentane carboxamides as small molecule antagonists of the human and murine CC chemokine receptor 2," *Bioorganic & Medicinal Chemistry Letters* (Apr. 16, 2007); 17:3636-3641.

Cannarile, Michael A. et al., "Colony-stimulating factor 1 receptor (CSF1R) inhibitors in cancer therapy," *Journal for Immuno Therapy of Cancer* (Published online Jul. 18, 2017); 5:53; 13 pages.

Carter, Percy H. et al., "Advances in the Discovery of CC Chemokine Receptor 2 Antagonists," *Annual Reports in Medicinal Chemistry* (2007); 42:211-227 [ISSN 0065-7743; DOI 10.1016/S0065-7743(07)42014-0].

Carter, Percy H. "Progress in the discovery of CC chemokine receptor 2 antagonists 2009-2012," Expert Opinion on Therapeutic Patents (published oline Feb. 22, 2013) 23(5):549-568.

Chen, Lieping et al., "Anti-PD-1/PD-L1 therapy of human cancer: past, present, and future," *J Clin Invest*. (Sep. 1, 2015); 125(9):3384-3391.

Chen, Xuguang et al., "CCL2/CCR2 Regulates the Tumor Microenvironment in *HER-2/neu*-Driven Mammary Carcinomas in Mice," *PLOS One* (Nov. 7, 2016); DOI:10.1371/journal.pone.01655595; 20 pages.

Cherney, Robert J. et al., "Discovery of Disubstituted Cyclohexanes as New Class of CC Chemokine Receptor 2 Antagonists," *J. Med. Chem*. (published on Web Jan. 31, 2008); 51(4):721-724.

Cheung, K-John J. et al., "Acquired *TNFRSF14* Mutations in Follicular Lymphoma are Associated with Worse Prognosis," *Molecular and Cellular Pathobiology* (Nov. 15, 2010); Cancer Res; 70(22):9166-9174.

Cohen, Ivan J. et al., "Impact of the Tumor Microenvironment on Tumor-Infiltrating Lymphocytes: Focus on Breast Cancer," *Breast Cancer: Basic and Clinical Research* (Accepted Aug. 14, 2017); 11:1-12.

De Zeeuw, D. et al., Abstract Only: "The effect of CCR2 inhibitor CCX140-B on residual albuminuria in patients with type 2 diabetes and nephropathy: a randomized trial," *Lancet Diabetes Endocrinol* (Sep. 2015; Epub Aug. 9, 2015); 3(9):687-696.

Dolan, Dawn E. et al., "PD-1 Pathway Inhibitors: Changing the Landscape of Cancer Immunotherapy," *Cancer Control* (Jul. 2014; accepted Apr. 29, 2014) 21(3):231-237.

Dörwald, F. Zaragoza, Side Reactions in Organic Synthesis: A Guide to Successful Synthesis Design, *Weinheim: Wiley-VCH Verlag GmBH & Co. KGaA*, © 2005, Preface; 6 pages.

Franklin, Ruth A. et al., "The Cellular and Molecular Origin of Tumor-associated Macrophages," *Science* (May 23, 2014); 344(6186):921-925.

Fujimura, Taku et al., "Regulatory T Cells Stimulate B7-H1 Expression in Myeloid-Derived Suppressor Cells in *ret* Melanomas," *Journal of Investigative Dermatology* (2012; published online Dec. 22, 2011); 132:1239-1246.

(56) References Cited

OTHER PUBLICATIONS

Fujimura, Taku et al., "Tumor-Associated Macrophages: Therapeutic Targets for Skin Cancer," *Frontiers in Oncology* (Jan. 23, 2018); 8(3); 6 pages.
Gao, Zhongli et al., "Unraveling the Chemistry of Chemokine Receptor Ligands," *Chem. Rev.* (2003; rec'd Nov. 26, 2002); 103:3733-3752.
Gong, Jiang-Hong et al., "An Antagonist of Monocyte Chemoattractant Protein 1 (MCP-1) Inhibits Arthritis in the MRL-*Ipr* Mouse Model," *J. Exp. Med.* (Jul. 7, 1997); 186(1):131-137.
Grivennikov, Sergei I., et al., "Immunity, Inflammation, and Cancer," *Cell* (Mar. 19, 2010); 140(6):883-899.
Guzik, Katarzyna et al., " Small-Molecule Inhibitors of the Programmed Cell Death-1/Programmed Death-Ligand 1 (PD-1/PD-L1) Interaction via Transiently Induced Protein States and Dimerization of PD-L1," *Journal of Medicinal Chemistry* (Jun. 14, 2017) 69(13):5857-5867.
Hackam, Daniel G. et al., "Translation of Research Evidence from Animals to Humans," *JAMA* (Oct. 11, 2006); 296(14):1731-1732.
Hitchcock, Jessica R. et al., "Anti-CCL2: building a reservoir or opening the floodgates to metastasis?" *Breast Cancer Research* (Published online May 21, 2015); 17:68; 2 pages.
Hwang, S.T. et al., "Mycosis fungoides and Sézary syndrome," *Lancet* (Mar. 15, 2008); 371(9616):945-957.
Janson, Christine et al., "Abstract 5655: Inhibition of CCR2 potentiates checkpoint inhibitor immunotherapy in murine model of pancreatic cancer," (Jul. 2017); 77(13):: Abstract 5655; 2 pages.
Jordan, V.Craig, "Tamoxifen: A Most Unlikely Pioneering Medicine," *Nature Reviews: Drug Discovery* (Mar. 2003); 2:205-213.
Jung, Heiyoun et al., "Abstract A107: Inhibition of CCR@ potentiates the checkpoint inhibitor immunotherapy in pancreatic cancer," *Cancer Immunology Research* (Nov. 2016) XP055804244 Retreived from the Internet: URL:https://cancerimmunolres.aacrjournals. Org/content/4/11_ Supplement/A107; 4 pages.
Kang, Young Sun et al., "CCR2 antagonism improves insulin resistance, lipid metabolism, and diabetic nepropathy in type 2 diabetic mice," *Kidney International* (published online Aug. 4, 2010); 78:883-894.
Karihaloo, Anil et al., "Macrophages Promote Cyst Growth in Polycystic Kidney Disease," *J Am Soc Nephrol* (Oct. 2011; accepted May 12, 2011); 22(10):1809-1814.
Kitagawa, Kiyoki et al., "Blockade of CCR2 Ameliorates Progressive Fibrosis in Kidney," *American Journal of Pathology* (Jul. 2004; accepted Mar. 30, 2004); 165(1):237-245.
Kothandaraman, Shankaran et al., "Design, synthesis, and structure-activity relationship of novel CCR2 antagonists," *Bioorganic & Medicinal Chemistry Letters* (2009; accepted Dec. 10, 2008); 19:1830-1834.
Krejsgaard, Thorbjørn et al., "Malignant inflammation in cutaneous T-cell lymphoma—a hostile takeover," *Semin Immunopathol* (2017; published online Oct. 7, 2016); 39:269-282.
Le, Dung et al., "Abstract CT124: A phase Ib/II study of BMS-813160, a CC chemokine receptor (CCR) 2/5 dual antagonist, in combination with chemotherapy or nivolumab in patients (pts) with advanced pancreatic or colorectal cancer," Cancer Research (Jul. 2018) XP55804393, Retrieved from the Internet URL:https://cancerres.aacrjournals.org/content/78/13_Supplement/CT124; 4 pages.
Lim, Jee Woong et al., "Synthesis and biological evaluation of 3-aminopyrrolidine derivatives as CC chemokine receptor 2 antagonsits," *Bioorganic & Medicinal Chemistry Letters* (2010; accepted Feb. 17, 2010); 20:2099-2102.
Lim, Su Yin et al., "Targeting the CCL2-CCR2 signaling axis in cancer metastasis," *Oncotarget* (Feb. 14, 2016); 7(19):28697-28710.
Miura, Kouichi et al., "Hepatic recruitment of macrophages promotes nonalcoholic steatohepatitis through CCR2," *Am J Physiol Gastrointest Liver Physiol* (Mar. 22, 2012); 302:G1310-G1321.
Miyagaki, T. et al., "Increased CCL18 expression in patients with cutaneous T-cell lymphoma: association with disease severity and prognosis," *Journal of the European Academy of Dermatology and Venereology*, (2013; Accepted Feb. 13, 2012); 27:e60-e67.
Moree, Wilna J. et al., "Potent antagonists of the CCR2b receptor. Part 3: SAR of the (*R*)-3-aminopyrrolidine series," *Bioorganic & Medicinal Chemistry Letters* (2008; accepted Feb. 7, 2008); 18:1869-1873.
Norman, Peter, "A dual CCR2/CCR5 chemokine antagonist, BMS-813160?" *Expert Opinion on Therapeutic Patents* (Sep. 22, 2011) 21(12):1919-1924.
Nywening, Timothy M., M.D. et al., "Phase 1b study targeting tumour associated macrophages with CCR2 inhibition plus Folfirinox in locally advanced and borderline resectable pancreatic cancer," *Lancet Oncol.* May 2016); 17(5):651-662.
Papadopoulos, Kyriakos P. et al., "First-in-Human Study of AMG 820, a Monoclonal Anti-Colony-Stimulating Factor 1 Receptor Antibody, in Patients with Advanced Solid Tumors," *Clin Cancer Res* (Oct. 1, 2017); 23(19):5703-5710.
Pasternak, Alexander et al., "Discovery of a Potent and Orally Bioavailable CCR2 and CCR5 Dual Antagonist," *ACS Med. Chem. Lett.* (2010; accepted Dec. 14, 2009); 1:14-18.
Pasternak, Alexander et al., "Potent heteroarylpiperidine and carboxyphenylpiperidine 1-alkyl-cyclopentane carboxamide CCR2 antagonists," *Bioorganic & Medicinal Chemistry Letters* (2008; accepted Dec. 11, 2007); 18:994-998.
Pasternak, Alexander et al., "Conformational studies of 3-amino-1-alkyl-cyclopentane carboxamide CCR2 antagonists leading to new spirocyclic antagonists," *Bioorganic & Medicinal Chemistry Letters* (2009; accepted Jan. 3, 2008); 18:1374-1377.
Pedersen, Martin B. et al., "High intratumoral macrophage content is an adverse prognostic feature in analplastic large cell lymphoma," *Histopathology* (Published online Mar. 4, 2014); 65:490-500.
Peranzoni, Elisa et al., "Macrophages impede CD8 T cells from reaching tumor cells and limit the efficacy of anti-PD-1 treatment," *PNAS* (Published online Apr. 9, 2018); 115(17):E4041-E4050.
Pienta, Kenneth J. et al., "Phase 2 study of carlumab (CNTO 888), a human monoclonal antibody against CC-chemokine ligand 2 (CCLS), in metastatic castration-resistant prostate cancer," *Invest New Drugs* (2013; published online Aug. 21, 2012); 31:760-768.
Press Release: ChemoCentryx's CCR2 Inhibitor CCX872 Shown to Reduce Liver Fibrosis in NASH Models, (Oct. 18, 2016); 4 pages.
Pubchem-'124' Create Date: Aug. 9, 2005; Date accessed Jul. 13, 2016; p. 3; compound; 13 pages.
Roblek, Marko et al. "Targeted delivery of CCR2 antagonist to activated pulmonary endothelium prevents metastasis," *J. Control Release* (Dec. 28, 2015); 220(Pt A):341-347.
Sandhu, Shahneen K. et al., "A first-in-human, first-in-class, phase I study of carlumab (CNTO 888), a human monoclonal antibody against CC-chemokine ligand 2 in patients with solid tumors," *Cancer Chemother Pharmacol* (Published online Feb. 6, 2013); 71:1041-1050.
Sanford, Dominic et al., "Inflammatory Monocyte Mobilization Decreases Patient Survival in Pancreatic Cancer: A Role for Targeting the CCL2/CCR2 Anxis," *Clin Cancer Res* (Jul. 1, 2013); 19(13):3404-3414.
Stanley, E. Richard et al., "CSF-1 Receptor Signaling in Myeloid Cells," *Cold Spring Harb Perspect Biol* (2014); 4(6):a021857; 21 pages.
Steinberg, Shannon M. et al., "Myeloid Cells that Impair Immunotherapy are Restored in Melanomas with Acquired Resistance to BRAF Inhibitors," *Cancer Research* (Feb. 15, 2017) 77(7):1599-1610.
Sugaya, Makoto et al., "Association of the numbers of CD163+ cells in lesional skin and serum levels of soluble CD163 with disease progression of cutaneous T cell lymphoma," *Journal of Dermatological Science* (Accepted Jul. 20, 2012); 68:45-51.
Tang, Xiaoqiang et al., "Anti-tumour strategies aiming to target tumour-associated macrophages," *Immunology* (Accepted Oct. 22, 2012); 138:93-104.
Trujillo, John I. et al., "Design and synthesis of novel CCR2 antagonists: Investigation of non-aryl/heteroaryl binding motifs," *Bioorganic & Medicinal Chemistry Letters* (2011; accepted Jan. 13, 2011); doi:10.1016/j.bmcl.2011.01.052.
Ueno, Takayuki et al., "Significance of Macrophage Chemoattractant Protein-1 in Macrophage Recruitment, Angiogenesis, and

(56) References Cited

OTHER PUBLICATIONS

Survival in Human Breast Cancer," *Clinical Cancer Research* (Aug. 2000; accepted May 22, 2000); 6:3282-3289.
Vestergaard, Christian et al., "Expression of CCR2 on Monocytes and Macrophages in Chronically Inflamed Skin in Atopic Dermatitis and Psoriasis," *Acta derm Venereol* (2004; accepted Apr. 12, 2004); 84:353-358.
Vippagunta, Sudha R. et al., "Crystalline solids," *Advanced Drug Delivery Reviews* (2001; accepted Dec. 21, 2000); 48:3-26.
Vogelstein Bert et al., "Cancer genes and the pathways they control," *Nature Medicine* (Aug. 2004; published online Jul. 30, 2004) 10(8):789-799.
Wein, Lironne et al., "Clinical Validity and Utility of Tumor-Infiltrating Lymphocytes in Routine Clinical Practice for Breast Cancer Patients: Current and Future Directions," *Frontiers in Oncology* (Aug. 3, 2017); 7(156); 10 pages.
Wikipedia article Spartalizumab; https://en.wikipedia.org/wiki/Spartalizumab; CAS No. 1935694-88-4; accessed Jun. 29, 2020 (1 page).
Wu, Xuesong et al., "Upregulation of Inflammatory Cytokines and Oncogenic Signal Pathways Preceding Tumor Formation in a Murine Model of T-Cell Lymphoma in Skin," *Journal of Investigative Dermatology* (Published online Apr. 14, 2011); 131:1727-1734.
Wu, Xuesong et al., "Depletion of M2-Like Tumor-Associated Macrophages Delays Cutaneous T-Cell Lymphoma Development In Vivo," *Journal of Investigative Dermatology* (Published online Jun. 5, 2014); 134:2814-2822.
Wu, Xuesong et al., "Cutaneous T-Cell Lymphoma: The Yin and Yang of Inflammation and Neoplasia," *The Journal of Investigative Dermatology Symposium* (Jul. 2015); 17:34-35.
Xue, Chu-Biao et al., "Discovery of INCB3284, a Potent, Selective, and Orally Bioavailable hCCR2 Antagonist," *ACS Med. Chem. Lett.* (2011; published Mar. 31, 2011); 2:450-454.
Xue, Chu-Biao et al., "Discovery of INCB8761/PF-4136309, a Potent, Selective, and Orally Bioavailable CCR2 Antagonist," *ACS Medicine Chemistry Letters* (Published Oct. 5, 2011); 2:913-918.
Yang, Li et al., "Tumor-associated macrophages, potential targets for cancer treatment," *Biomarker Research* (Published online Aug. 8, 2017); 5:25; 6 pages.
Yao, Min et al., "Continuous Delivery of Neutralizing Antibodies Elevate CCL2 Levels in Mice Bearing MCF10CA1d Breast Tumor Xenografts," *Translational Oncology* (Oct. 2017; accepted Jun. 15, 2017); 10(5):734-743.
Yao, Wenbo et al., "A Natural CCR2 Antagonist Relieves Tumor-associated Macrophage-mediated Immunosuppression to Produce a Therapeutic Effect for Liver Cancer," *EBioMedicine* (Available online Jul. 18, 2017); 22:58-67.
Zhang, Jian et al., "Targeting chemokine (C—C motif) ligand 2 (CCL2) as an example of translation of cancer molecular biology to the clinic," *Prog Mol Biol Transl Sci* (2010); 95:31-53. doi:10.1016/B978-0-12-385071-3.00003-4.
Zheng, Yi et al., "Structure of CC Chemokine Receptor 2 with Orthosteric and Allosteric Antagonists," *Nature* (Dec. 15, 2016); 540(7633):458-461.
Extended European Search Report dated Oct. 10, 2022 corresponding to EP Appl 19735699.1 filed Apr. 18, 2019; 8 pages.
Gopinath Adithya et al., IMMU-09. Disruption of the CCL2-CCR2 Axis Augments the Effects of Immune Checkpoint Inhibitors to Slow Progression of Gliomas. *Neuro-Oncology* Nov. 30, 2017, vol. 19, No. suppl_6, p. vi114 (Abstract; 1 page).

* cited by examiner

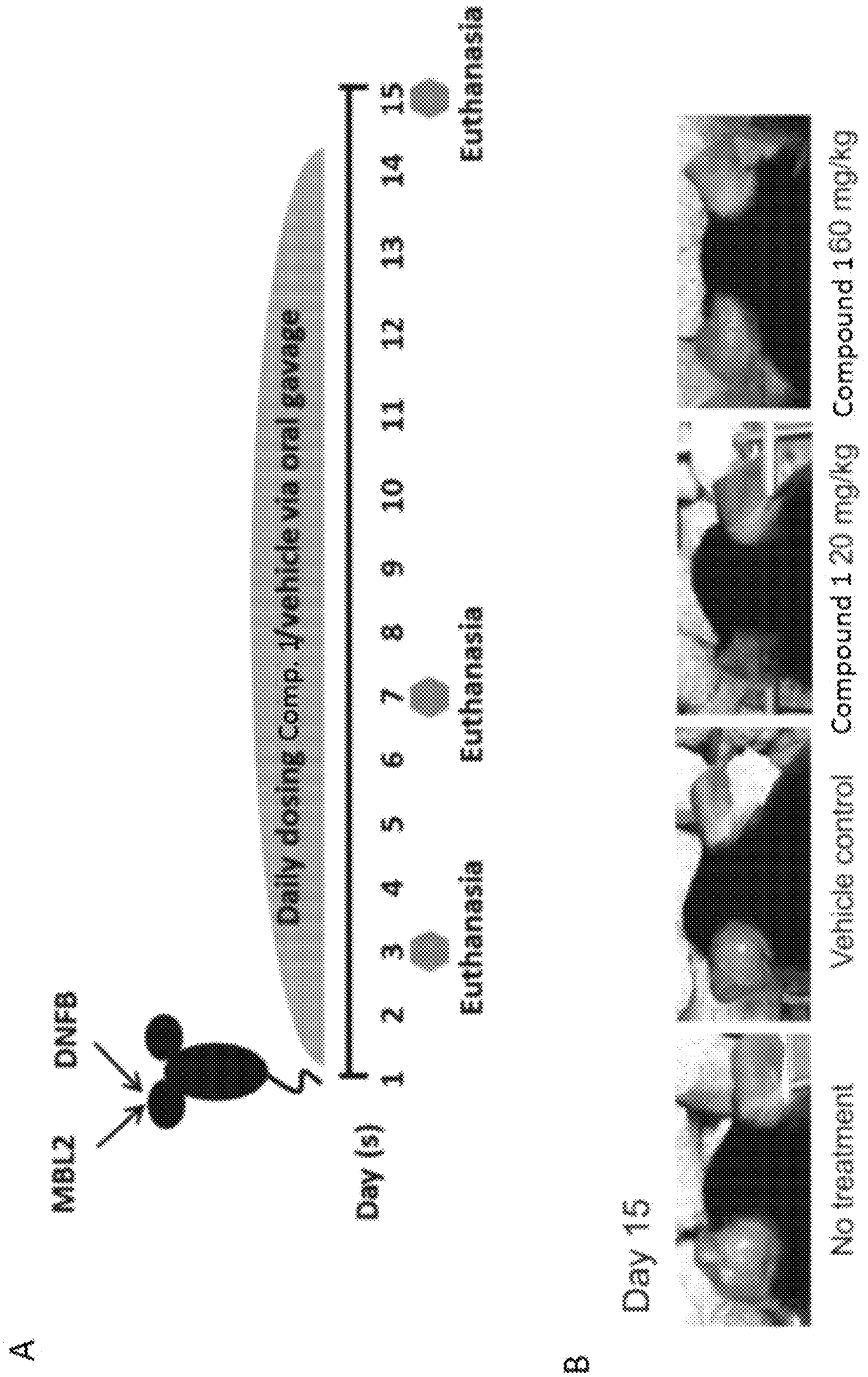
FIG. 1A-B

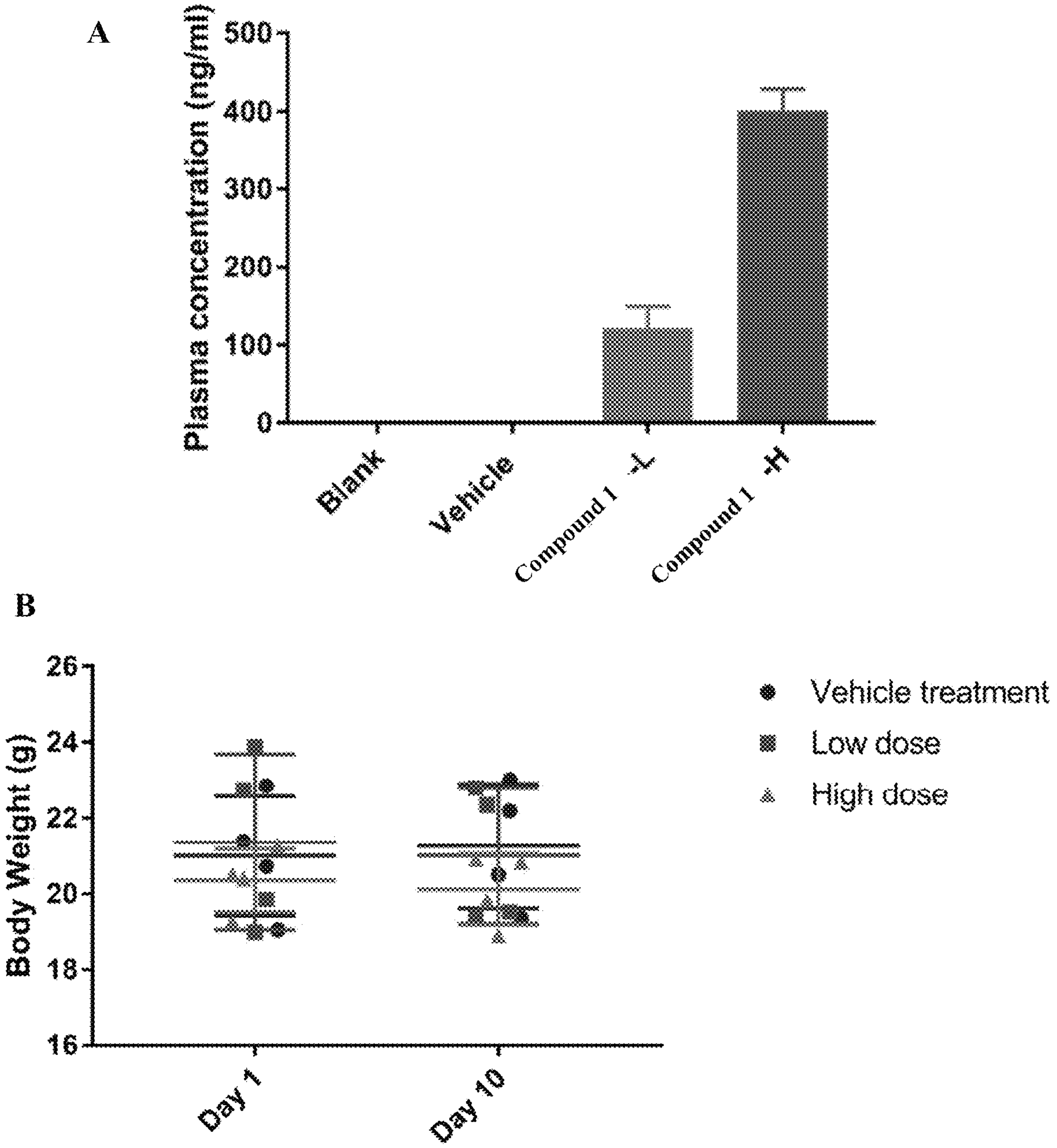
FIG. 2A-B

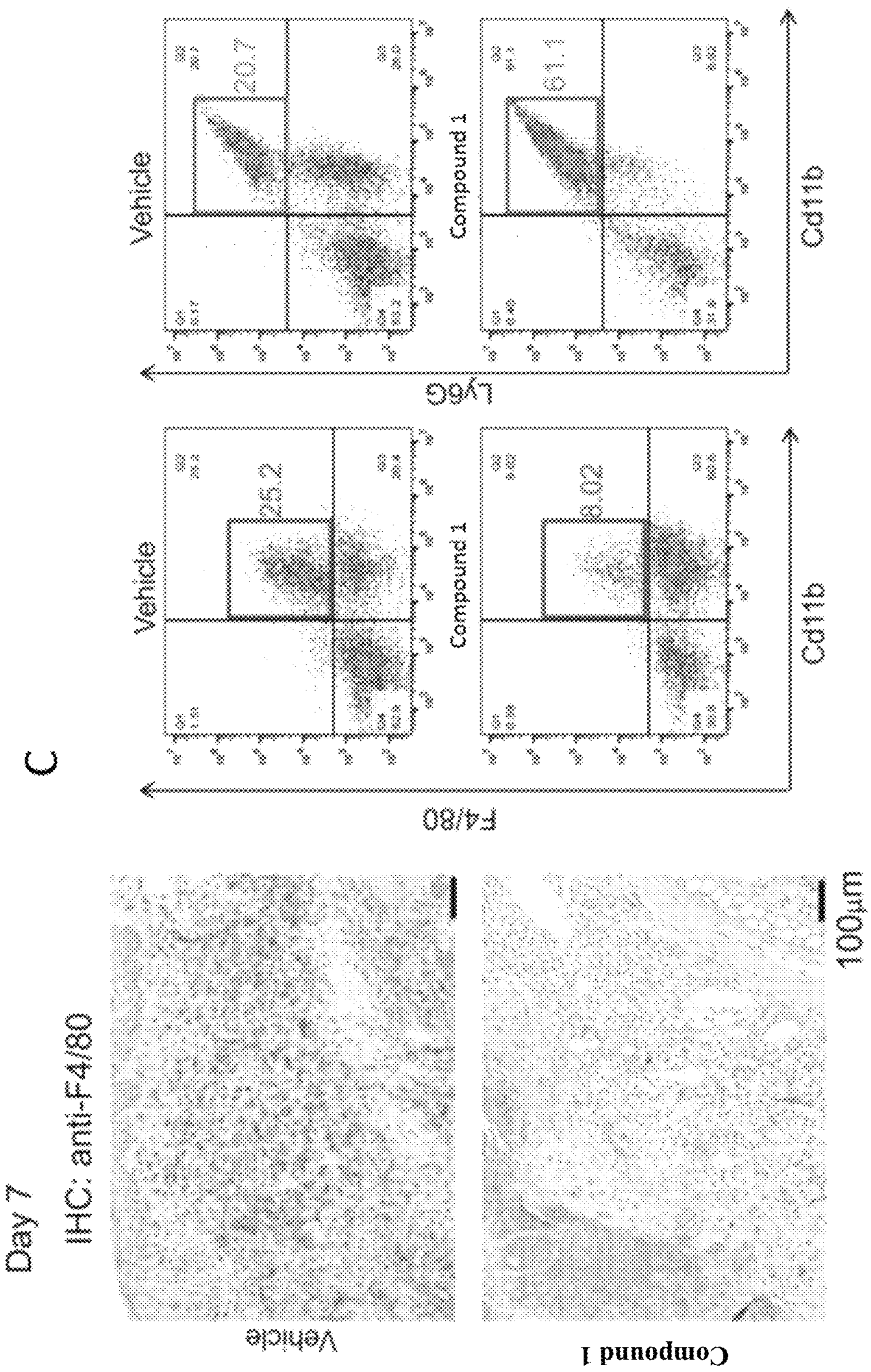
FIG. 4B-C

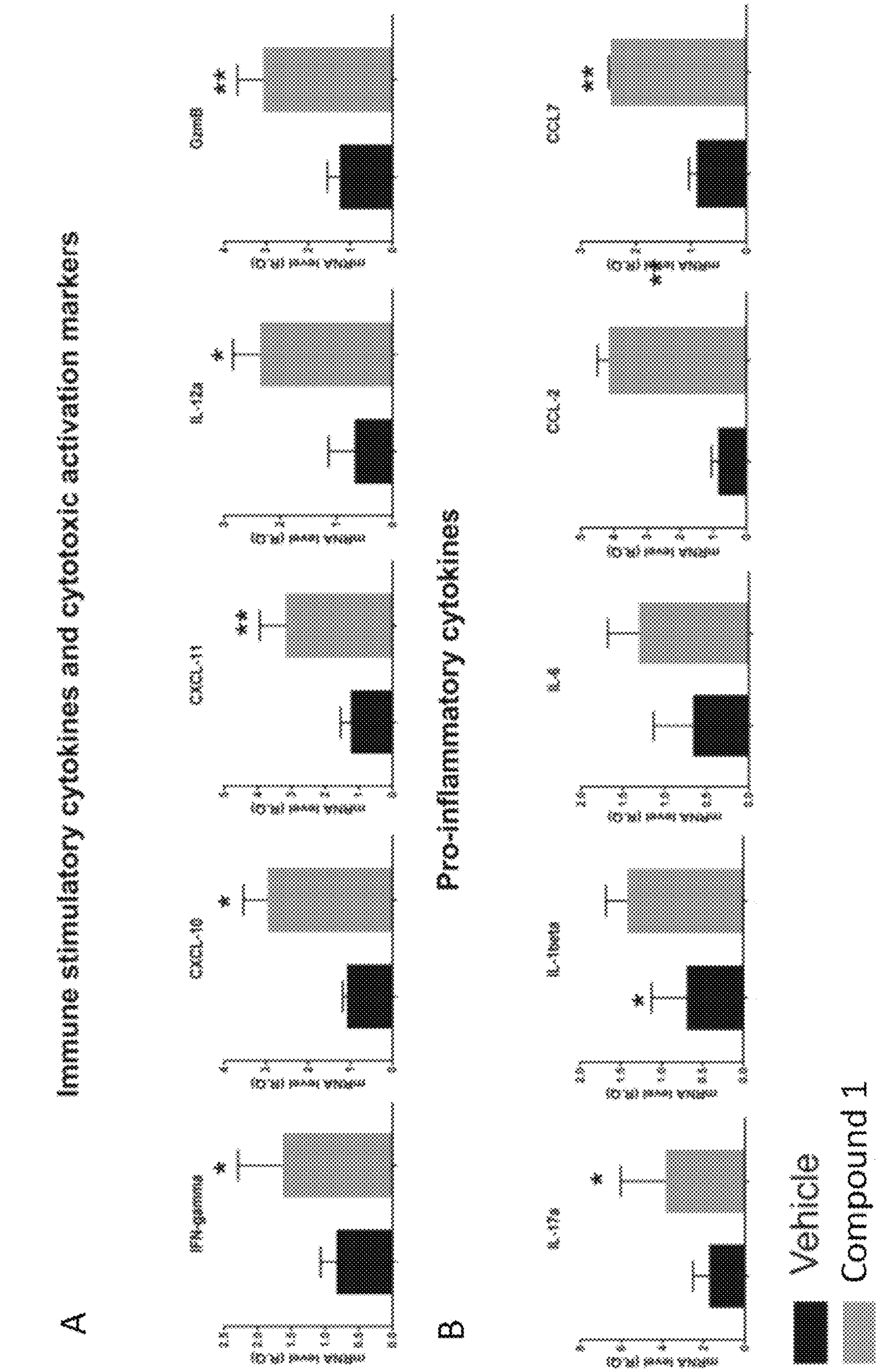
FIG. 5A-B

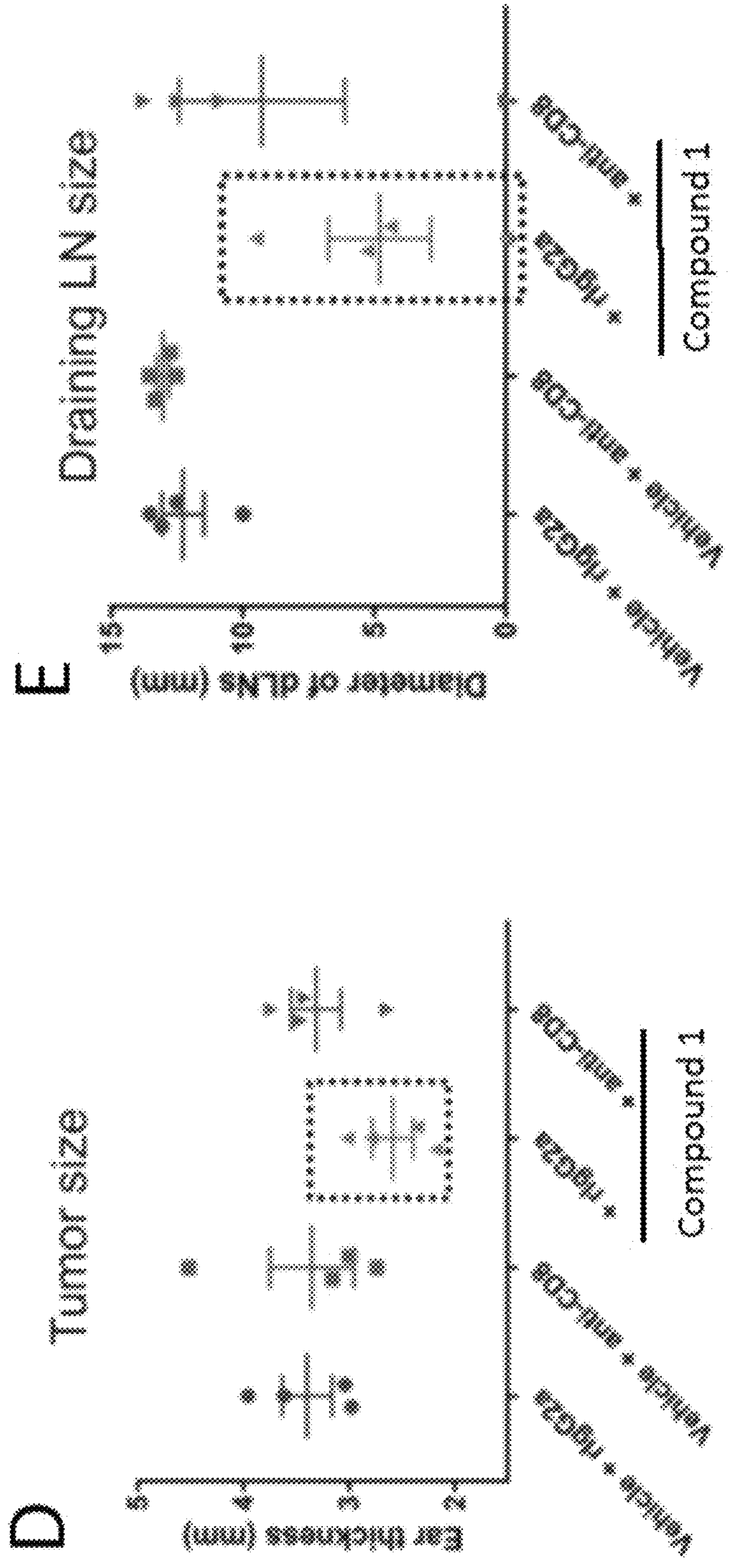
FIG. 7D-E

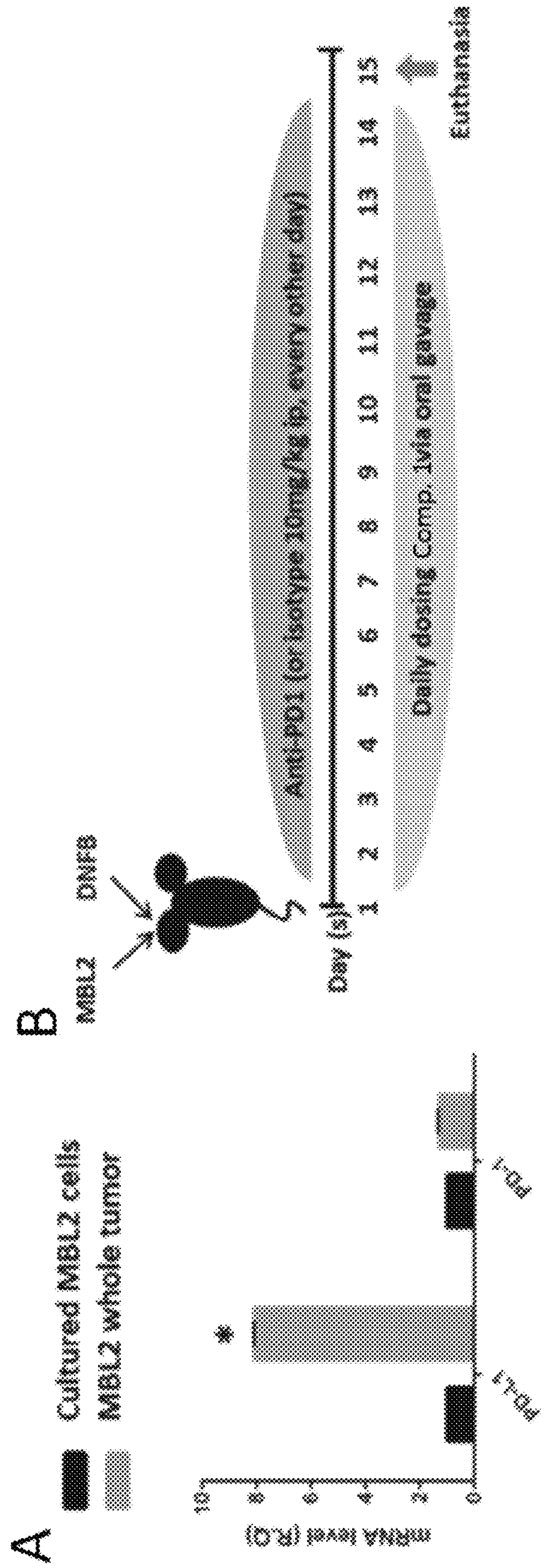
FIG. 8A-B

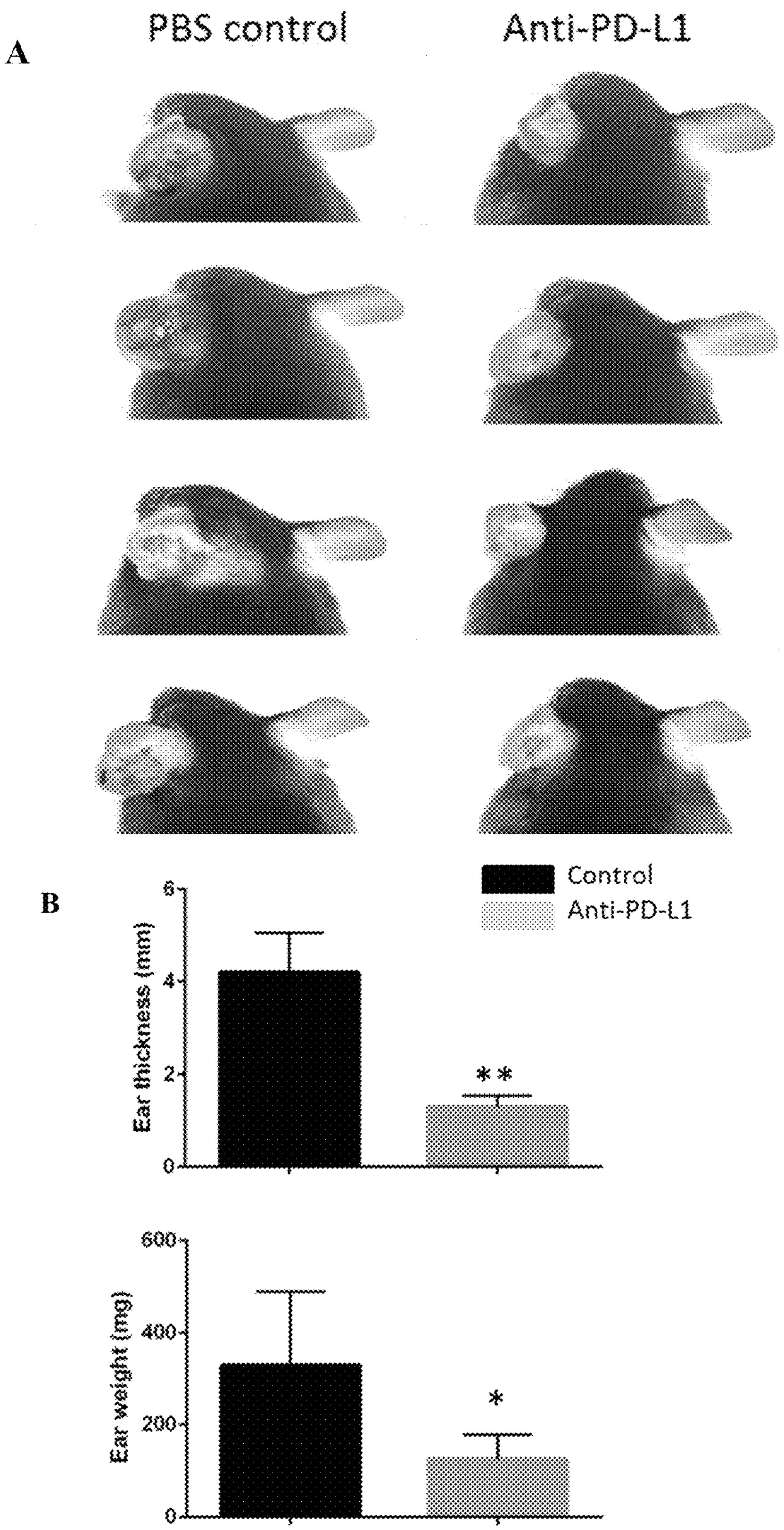
FIG. 9A-B

METHODS OF TREATING SOLID TUMORS WITH CCR2 ANTAGONISTS

CROSS-REFERENCES TO RELATED APPLICATIONS

This application is a continuation of U.S. patent application Ser. No. 16/241,391 filed Jan. 7, 2019, which application claims the benefit of priority under 35 U.S.C § 119 (e) to U.S. Provisional Application Ser. No. 62/614,923 filed Jan. 8, 2018, the disclosure of each is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

Tumor-associated macrophages (TAMs) are present in a large number in tumor tissues which enhance the cancer-promoting inflammation [1-3]. TAMs contribute to the immunosuppressive tumor microenvironment (TME) by secreting a number of chemokines that are crucial to the recruitment of immunosuppressive cells. Furthermore, they produce angiogenetic factors such as VEGF, platelet-derived growth factor, and transforming growth factor β to induce neovascularization. Moreover, PD-L1 (also known as B7H1) on macrophages confers TAMs with direct suppressive function by inducing antigen-specific tolerance in tumor-bearing hosts [3-5].

The abundance of macrophages in the TME and inverse correlation with survival has been frequently reported in malignancies, including prostate, breast, colorectal, pancreas, and lymphomas [4, 6]. High macrophage density in tumors are associated with poor patient prognosis and treatment resistance, and has fueled cancer therapeutic strategies targeting TAMs [7]. Of note, the presence of TAMs in human non-Hodgkin's lymphoma has been shown to not only correlate with patient's survival but also the responses to treatment [8]. Macrophage colony stimulating factor 1 receptor (CSF1R)-mediated signaling directs monocyte survival and macrophage differentiation [9]. However, clinical trials applying strategies of CSF1R blockade are inconsistent in showing patient improvement. The main reason for imperfect CSF1R inhibition may be caused by the dependency of the agent's ability to access malignant cells in the TME, potentially reducing the therapeutic effect of CSF1R blockade [7, 10-12].

Blocking monocyte recruitment to tumors by targeting the CCL2-CCR2 axis provides another promising strategy [13]. Neutralizing CCL2 antibodies have been demonstated to slow tumor progression in preclinical studies [14]. Clinical trials, however, showed limited clinical responses. Pharmacokinetic data revealed a rapid dissociation of the antibody and an undesired increase in serum CCL2 concentrations when targeting the CCL2/CCR2 axis in metastatic prostate cancer with a monoclonal CCL2 antibody [15-18].

CCR2 antagonists have become attractive for targeting the CCL2-CCR2 axis in light of the limitations mentioned above [19, 20]. In a phase 1b study, CCR2 blockade by orally dosed small molecule CCR2 antagonist (PF-04136309) has demonstrated a reduction in TAM infiltration and an endogenous anti-tumor immune response in pancreatic ductal adenocarcinoma (PDAC)[21]. Overall, there is a scarcity of clinical trials with beneficial outcomes, and further studies are required to quantify the impact in different cancers. Mechanistically, how CCR2 antagonists reshape the TME and how CCR2 antagonists activate anti-tumor immunity yet remain to be described in preclinical tumor models with respect to cellular immunomodulation. Additionally, optimized selection and combination of standard chemotherapies for TAM targeting with radiotherapy or immunotherapy await development [22].

The present disclosure addresses these needs and provides related advantages as well.

BRIEF SUMMARY

In one aspect, present disclosure provides methods of treating a solid tumor, said method comprising administering effective amount of a Chemokine Receptor 2 (CCR2) antagonist.

In some embodiments, the tumor is a lymphoma. In some embodiments the lymphoma is cutaneous T cell lymphoma (CTCL).

In still another aspect, present disclosure provides methods of reducing the number of macrophages in a solid tumor microenvironment, said method comprising administering effective amount of a Chemokine Receptor 2 (CCR2) antagonist.

In yet another aspect, the present disclosure provides methods of increasing the number CD8+ T cells in a solid tumor microenvironment, said method comprising administering effective amount of a Chemokine Receptor 2 (CCR2) antagonist.

In some embodiments, the CCR2 receptor antagonist has the formula I (I)

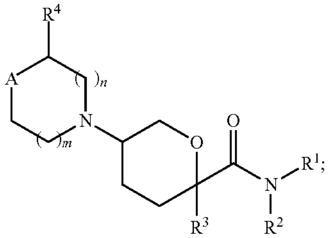

where each variable is described below.

In some embodiments, the CCR2 antagonist has the formula selected from the group consisting of

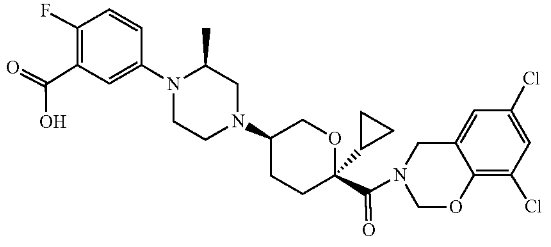

-continued

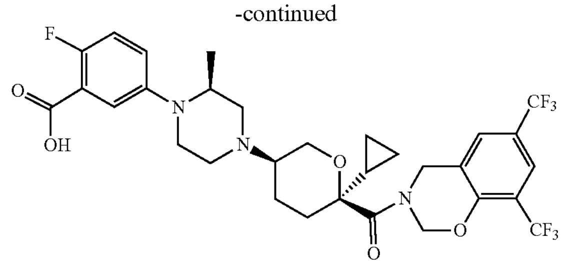

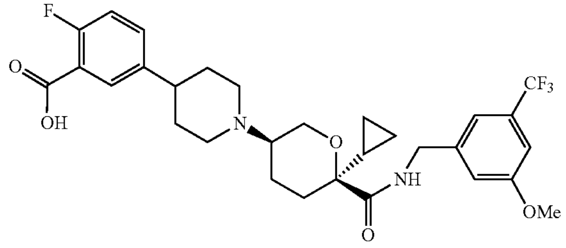

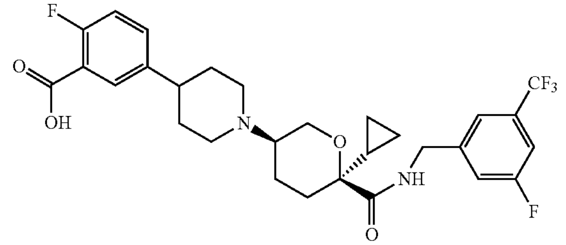

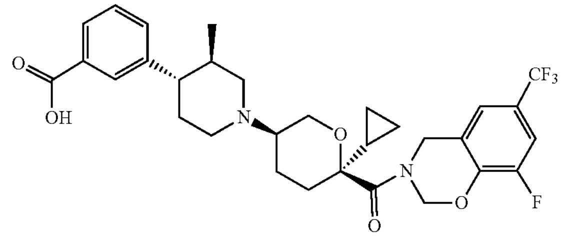

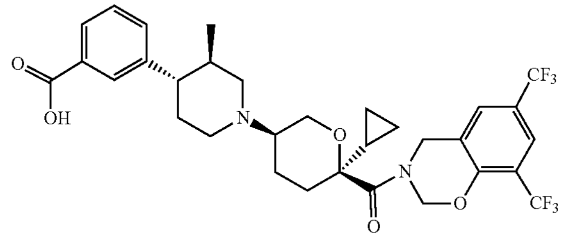

or a pharmaceutically acceptable salt thereof.

In some embodiments, the CCR2 antagonist has the formula (Compound 1)

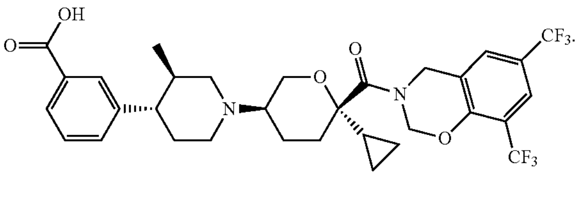

or a pharmaceutically acceptable salt thereof.

In some embodiments, the CCR2 antagonist has the formula (Compound 2)

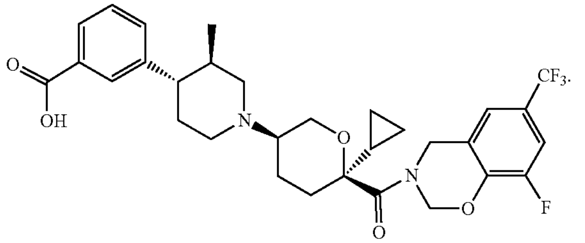

or a pharmaceutically acceptable salt thereof.

In some embodiments, the CCR2 antagonist has the formula (Compound 3)

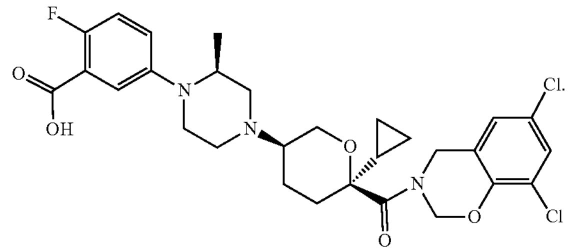

or a pharmaceutically acceptable salt thereof.

BRIEF DESCRIPTION OF THE DRAWINGS

FIG. 1A-C. Oral administration of Compound 1 inhibits tumor growth in the MBL2/DNFB mouse model. (A) Scheme for the treatment regimen. Compound 1 is orally fed at 20 or 60 mg/kg daily for two weeks. Mice are euthanized on day 15 for examining the ear tumors. Extra mice are euthanized on day 3 or day 7 for determining earlier therapeutic responses. (B) Examination on ear tumors in MBL2/DNFB mice which were treated with two different doses of Compound 1 and vehicle for two weeks. One representative ear from each group of 8 is shown. (C) Ear thickness and ear weight are measured immediately after euthanasia on day 15 (*: $p \leq 0.05$, ***: $p \leq 0.001$).

FIG. 2A-B. Orally administration of Compound 1 is dose-dependently absorptive and well tolerant in mice. (A) Mice were orally dosed for Compound 1 daily at a lower concentration (20 mg/kg per day) or a higher concentration (60 mg/kg per day) for consecutive ten days. Plasma concentration of Compound 1 was detected by chemistry analyst 24 hours after the last dosing. (B) The same groups of mice in panel (A) were recorded for body weight before the first and after the last oral administration (n=4 per group). Statistical analysis is performed by two-way ANOVA in GraphPad PRISM (GraphPad Software, San Diego, CA).

FIG. 4A-C. Enhanced inflammation is associated with CCR2 antagonism by Compound 1 in the tumor microenvironment. (A, B) Ear tissues were collected from mice treated by Compound 1 (60 mg/kg) or vehicle on day 7. Representative images for HE sections and IHC staining with anti-F4/80 were shown for the ear tissues from Compound 1 and vehicle treated group. (C) Ears from day 7 were also analyzed by flow cytometry to quantify the numbers of the two major myeloid subpopulations in TME with antibodies for CD11b, F4/80 and Ly6G.

FIG. 5A-C. Compound 1 treatment altered the expression of cytokines and biomarkers produced from the TME. Quantitative RT-PCR was performed for the ear tissues collected on day 7. Genes that are involved in cancer inflammation and immunity crosstalk are selectively detected. Comparative expression is performed between the Compound 1 and vehicle treated groups. (A) Shows immune stimulatory cytokines and cytotoxic activation markers; (B) shows pro-inflammatory cytokines; and (C) shows neutrophil chemoattractants and biomarkers. Gene expression values are normalized to endogenous expression of GAPDH (* $p<0.05$, ** $p<0.01$; n=3 mice per group).

FIG. 7A-E. CD8 T cells are compulsory in CCR2 antagonist-mediated anti-tumor immunity. (A) Tumor tissues were collected from mice euthanized after two weeks of treatment. Groups are as indicated in the graph. IHC staining with CD8a antibody was performed. The numbers of CD8 positive T cells were counted by taking three random images of HPF (high power field) in each section from all four mice per group. (B) Scheme for neutralizing CD8 T cells along with Compound 1 treatment. Neutralizing anti-CD8 or rat-IgG2a was administrated via intraperitoneal injection one day before MBL2 tumor inoculation followed by a second dose after 7 days. Tumor formation was examined in two weeks after the treatment with Compound 1 or vehicle. (C) Mice treated in experiment (B) were euthanized on day 3 for flow analysis of the cervical draining lymph nodes in order to determine the effect of CD8 depletion (three mice per group). (D) Mice were euthanized on day 15 after the two weeks of Compound 1/vehicle treatment with or without CD8 T cell neutralization. Ear thickness is measured for presenting tumor size. (E) Draining lymph nodes are also measured for the lymph node metastasis (n=4).

FIG. 8A-D. Compound 1 and anti-PD1 synergize the anti-tumor effect in MBL2 tumors. (A) qRT-PCR was performed to compare the expression of PD1 and PD-L1 respectively in MBL2 tumors formed in ear skin compared to in vitro cultured MBL2 cells. (B) Scheme for combining treatment with anti-PD1 with Compound 1 or vehicle control. (C) Spleens from the mice after two weeks of treatment were processed for single cell suspension followed by intracellular staining for flow analysis (Representative flow graph from each group is shown). (D) Ear tumors were examined in mice euthanized after two weeks of treatment. Representative ear photo from each group is shown (* $p<0.05$, n=8 mice per group). The dotted line in ear thickness bar graph indicates a borderline between a positive and a negative ability for tumor formation.

FIG. 9A-B. Anti-PD-L1 inhibits MBL2/DNFB tumor growth in mouse ears. Anti-PD-L1 (BioXcell, 150 ug per mouse, three times a week through IP) was administered starting from the same day of MBL2 tumor implantation. Mice were euthanized after two weeks of treatment. Ear tumor sizes and tumor weights were recorded. (A) Pictures are shown for two groups of mice treated with either anti-PD-L1 or PBS control. (B) Ear thickness and ear weight were measured (* $p<0.05$, ** $p<0.01$, n=4 mice per group)

DETAILED DESCRIPTION OF THE INVENTION

I. General

Figure 1C:
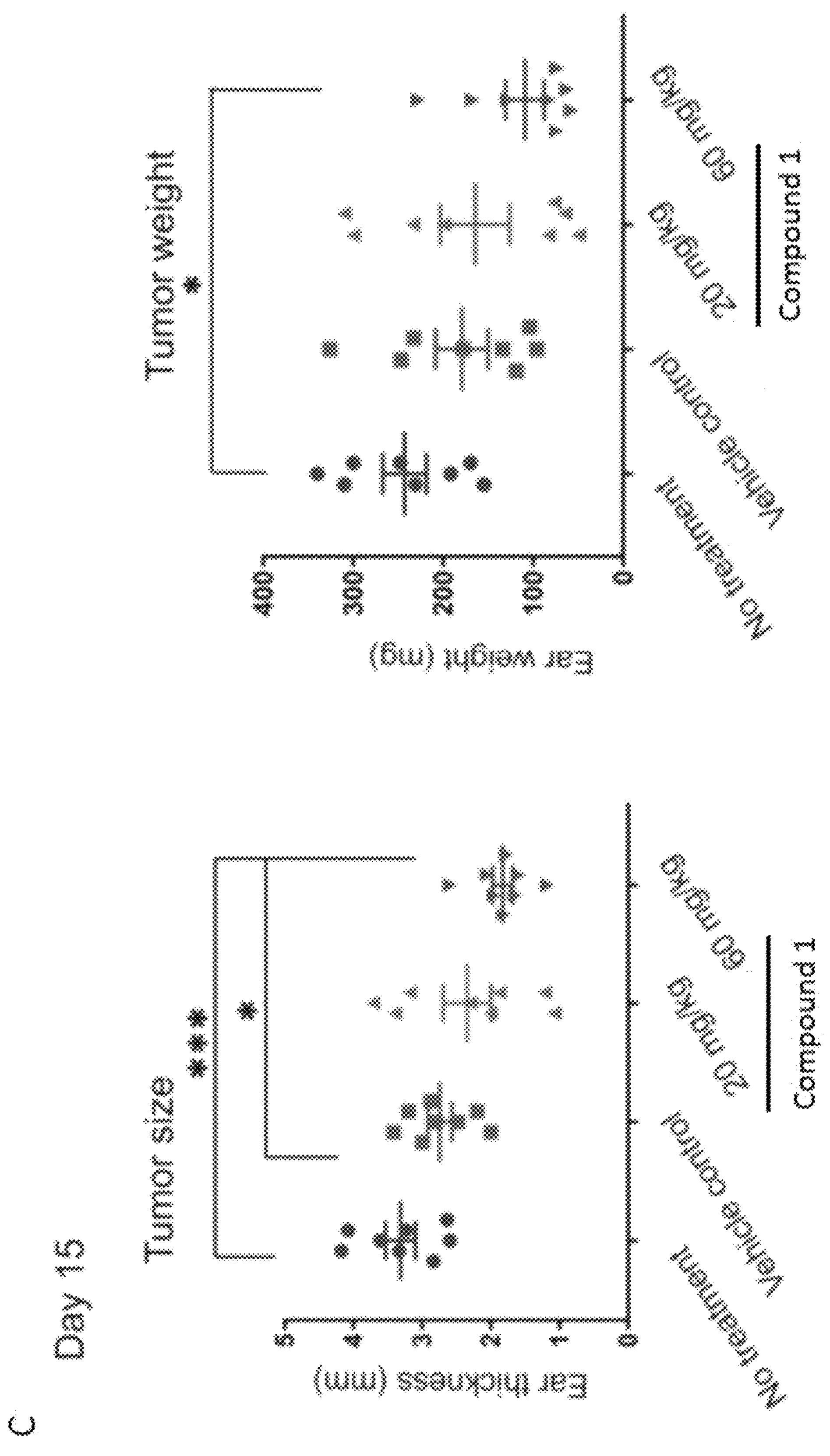

The present disclosure is drawn, in part, to the surprising and unexpected finding that a CCR2 antagonist can be used to effectively treat a solid tumor and related lymphomas.

Cutaneous T cell lymphomas (CTCLs) are a heterogeneous group of T cell neoplasms that are primarily localized to skin, comprising the two most common types, mycosis fungoides (MF) and Sézary syndrome (SS) [23]. Evidence of skin inflammation is common in CTCLs [24, 25]. In lesional skin of MF or SS, the numbers of CD163-positive macrophages are increased and CC chemokine ligand 18 expression by macrophages promotes a T-helper (Th)2-dominant microenvironment by inducing chemotaxis of Th2 cells. Such a tumor microenvironment is regarded as a determining factor to progressive clinical behavior of CTCL [26, 27]. By targeting TAMs in the TME with a CCR2 antagonist, we provide alternative strategies for patients at tumor-stage CTCL, where good therapeutic options are limit.

Prior reports have established a high grade T cell lymphoma model in mouse skin by injection of MBL2 T lymphoma cells in ear skin followed by application of 2,4-dinitro-1-fluorobenzene (DNFB)[28]. Tumor formation in this model is strictly dependent on the topical application of DNFB, which triggers an inflammatory skin response that promotes tumor formation. Herein, we demonstrate that Compound 1, a small molecule CCR2 antagonist, depletes macrophages in the TME in the ear, leading to significantly more production of anti-tumor cytokines, such as IFN-γ. Administration of a CCR2 antagonist led to expansion of CD8 T cells and consequently decreased the growth of implanted tumor cells. This mechanism is supported by the observation that this anti-tumor effect can be abrogated by simultaneously administering neutralizing CD8 monoclonal antibody. Finally, we demonstrate that treatment efficacy of the CCR2 antagonist is increased by co-administration of anti-PD1 antibody. Together, this report demonstrates that blocking the recruitment of TAMs into the TME may be an effective strategy for treating T cell lymphoma and more generally, solid tumors.

II. Abbreviations and Definitions

CTCL (cutaneous T cell lymphoma); MF (mycosis fungoides); Tumor microenvironment (TME); DNFB (2,4-dinitro-1-fluorobenzene); PD-1 (programmed death ligand 1);

qRT-PCR (Quantitative real-time PCR); TAMs (tumor-associated macrophages); IP (intraperitoneal); mAb (monoclonal antibody); IHC (immunohistochemistry).

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom. For terms such as cycloalkylalkyl and heterocycloalkylalkyl, it is meant that a cycloalkyl or a heterocycloalkyl group is attached through an alkyl or alkylene linker to the remainder of the molecule. For example, cyclobutylmethyl—is a cyclobutyl ring that is attached to a methylene linker to the remainder of the molecule.

The term "alkylene" by itself or as part of another substituent means a divalent radical derived from an alkane, as exemplified by $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH{=}CH—N(CH_3)—CH_3$. Up to two heteroatoms may be consecutive, such as, for example, $—CH_2—NH—OCH_3$ and $—CH_2—O—Si(CH_3)_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom (s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by $—CH_2—CH_2—S—CH_2CH_2—$ and $—CH_2—S—CH_2—CH_2—NH—CH_2—$, $—O—CH_2—CH{=}CH—$, $—CH_2—CH{=}C(H)CH_2—O—CH_2—$ and $—S—CH_2{\equiv}C—$. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as $—NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group that is attached to the remainder of the molecule (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —CN and —$NO_2$ in a number ranging from zero to (2 m'+1), where m' is the total number of carbon atoms in such radical. R', R" and R"' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)$CH_3$, —C(O)$CH_2CH_2$OR' and the like).

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula —T—C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

For the compounds provided herein, a bond that is drawn from a substituent (typically an R group) to the center of an aromatic ring (e.g., benzene, pyridine, and the like) will be understood to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When compounds are provided herein with an identified stereochemistry (indicated as R or S, or with dashed or wedge bond designations), those compounds will be understood by one of skill in the art to be substantially free of other isomers (e.g., at least 80%, 90%, 95%, 98%, 99%, and up to 100% free of the other isomer).

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^{3}H$), iodine-125 ($^{125}I$) or carbon-14 ($^{14}C$), or non-radioactive isotopes, such as deuterium ($^{2}H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

As used herein, the term “solid tumor” refers to a malignant neoplasm. A solid tumors is generally localized mass of tissue; however, solid tumors are able to invade surrounding tissue and metastasize to new body sides. Solid tumors may be benign (not cancer), or malignant (cancer). Different types of solid tumors are named for the type of cells that form them. Examples of solid tumors are sarcomas, carcinomas, and lymphomas. The term “solid tumor” does not include leukemia. (cancers of the blood). “Sarcomas” are cancers arising from connective or supporting tissues such as bone or muscle. “Carcinomas” are cancers arising from glandular cells and epithelial cells, which line body tissues. “Lymphomas” are cancers of the lymphoid organs such as the lymph nodes, spleen, and thymus. As these cells occur in most tissues of the body, lymphomas may develop in a wide variety of organs. Exemplary solid tumors include but are not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing’s tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm’s tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, cutaneous T cell lymphoma (CTCL), melanoma, neuroblastoma, and retinoblastoma.

III. Detailed Description of Embodiments

A. Methods

In one aspect, the present disclosure provides methods of treating a solid tumor, said method comprising administering effective amount of a Chemokine Receptor 2 (CCR2) antagonist.

In some embodiments the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing’s tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm’s tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, cutaneous T cell lymphoma (CTCL), melanoma, neuroblastoma, and retinoblastoma.

In some embodiments, the solid tumor is brain cancer, breast cancer, triple negative breast cancer, bladder cancer, bone cancer, colorectal cancer, lung cancer, kidney cancer, liver cancer, stomach cancer, prostate cancer, sarcoma, melanoma, carcinoma, or a lymphoma.

In some embodiments, the solid tumor is prostate cancer, breast cancer, colorectal cancer, pancreatic cancer, or a lymphoma.

In some embodiments the solid tumor is a lymphoma. In some embodiments, the lymphoma is cutaneous T cell lymphoma (CTCL). As described above cutaneous T cell lymphomas (CTCLs) are a hetergenous group of T cell neoplasms primarily localized to the skin.

CTCL is commonly broken into four separate stages (including sub-stages). Early stage CTCL (Stage IA and IB) includes the skin being covered in red patches or plaques. The difference between Stage IA and Stage IB is the amount of skin affected by red patches or plaques. At Stage IIA in additional to skin patches/plaques, the lymph nodes of affected individuals are enlarged, but the cancer has not spread to the notes. Stage IIB is the stage where one or more tumors are found on the skin (i.e., "tumor-stage CTCL"), the lymph nodes may be enlarged, but cancer has not spread to the lymph nodes. In Stage III CTCL, nearly all of the skin is reddened including patches, plaques, and/or tumors, lymph nodes may be enlarged, but cancer has not spread to the lymph nodes. In Stage IV, the cancer has spread to the lymph nodes or to other organs.

The present disclosure contemplates treating any of stages I-IV with the methods described herein. In some embodiments, subjects have early stage CTCL (i.e. Stage IA, IB, or IIA). In some embodiments, subjects with CTCL are in Stage IIB or a more advanced stage (i.e., the "tumor-stage CTCL). Thus, in some embodiments, the subject is diagnosed with Stage IIB or a more advanced form of CTCL. In some embodiments, the subject is diagnosed with Stage IIB CTCL.

In some embodiments, the CTCL is a specific subtype of CTCL. In some embodiment, the CTCL is mycosis fungoides (MF). In some embodiments, the CTCL is Sézary syndrome (SS).

In a second aspect, the present disclosure provides methods of reducing the number of macrophages in a solid tumor microenvironment, said method comprising administering effective amount of a Chemokine Receptor 2 (CCR2) antagonist.

In a third aspect, the present disclosure provides methods of increasing the number CD8+ T cells in a solid tumor microenvironment, said method comprising administering effective amount of a Chemokine Receptor 2 (CCR2) antagonist.

B. CCR2 Antagonists

In some embodiments, the CCR2 antagonist is a small molecule antagonist of CCR2 having the formula (I):

(I)

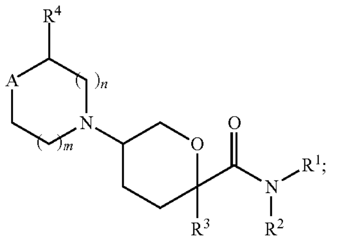

or a pharmaceutically acceptable salt, hydrate, stereoisomer or rotamer thereof; wherein A is $C(R^5)(R^6)$ or $N(R^5)$ the subscripts m and n are each independently integers of from 0 to 2, and m+n is ≤3;

$R^1$ is selected from the group consisting of aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 5 $R^x$ substituents;

$R^2$ is selected from the group consisting of H, $C_{1-8}$ alkyl, $C_{3-8}$ cycloalkyl, $C_{3-8}$ cycloalkyl-$C_{1-4}$ alkyl, aryl, aryl-$C_{1-4}$ alkyl, heteroaryl and heteroaryl-$C_{1-4}$ alkyl, wherein the heteroaryl portion has from 1-3 heteroatoms as ring members selected from N, O and S; and wherein said aryl and heteroaryl groups or portions are optionally substituted with from 1 to 4 $R^x$ substituents;

or optionally, $R^1$ and $R^2$ are combined with the nitrogen atom to which each is attached to form a 6- to 11-membered monocyclic or fused bicyclic-heterocyclic or heteroaryl ring, wherein the $—NR^1R^2$ is optionally further substituted with from 1 to 4 $R^x$ substituents;

$R^3$ is selected from the group consisting of H, $C_{1-8}$ alkyl, $C_{3-8}$ cycloalkyl and $C_{3-8}$ cycloalkyl-$C_{1-4}$ alkyl, each of which is optionally substituted with from 1-3 $R^y$ substituents;

$R^4$ is selected from the group consisting of H, $C_{1-8}$ alkyl optionally substituted with 1 to 2 $R^y$, and $—CO_2H$:

$R^5$ is selected from the group consisting of $C_{1-8}$ alkyl, $C_{1-8}$ alkoxy, $C_{3-8}$ cycloalkyl, $C_{3-8}$ cycloalkyloxy, $C_{3-8}$ cycloalkyl-$C_{1-4}$ alkyl, $C_{1-8}$ alkylamino, di-$C_{1-8}$ alkylamino, aryl, aryloxy, arylamino, aryl-$C_{1-4}$ alkyl, heteroaryl, heteroaryloxy, heteroarylamino and heteroaryl-$C_{1-4}$ alkyl, each of which is optionally substituted with from 1 to 5 $R^z$ substituents;

$R^6$ is selected from the group consisting of H, F, OH, $C_{1-8}$ alkyl and $C_{1-8}$ alkoxy, wherein the $C_{1-8}$ alkyl and $C_{1-8}$ alkoxy groups are optionally substituted with from 1 to 3 $R^z$ substituents;

or optionally, $R^5$ and $R^6$ are joined to form a spirocyclic 5- or 6-membered cycloalkyl ring which is optionally unsaturated, and has a fused aryl group which is optionally substituted with from 1 to 4 $R^z$ substituents;

each $R^x$ is independently selected from the group consisting of halogen, —CN, $—R^c$, $—CO_2R^a$, $—CONR^aR^b$, $—C(O)R^a$, $—OC(O)NR^aR^b$, $—NR^bC(O)R^a$, $—NR^bC(O)_2R^c$, $—NR^a—C(O)NR^aR^b$, $—NR^a(O)NR_aR^b$, $—NR^aR^b$, $—OR^a$, $—O—X^1—OR^a$, $—O—X^1—NR^aR^b$, $—O—X^1—O—X^1—CO_2R^a$, $—O—X^1—CONR^aR^b$, $—X^1—NR^aR^b$, $—X^1—CO_2R^a$, $—X^1—CONR^aR^b$, $—SF_5$, $—S(O)_2NR^aR^b$, and 5- or 6-membered aryl or heteroaryl, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^c$ is independently selected from the group consisting of $C_{1-8}$ alkyl, $C_{1-8}$ haloalkyl and $C_{3-6}$ cycloalkyl; and optionally when two $R^x$ substituents are on adjacent atoms, are combined to form a fused five or six-membered carbocyclic ring, and wherein the aryl or heteroaryl groups are optionally substituted with 1-3 members selected from halogen, hydroxyl, $C_{1-4}$ alkyl, $C_{1-4}$ alkoxy, $C_{1-4}$ haloalkyl, and $C_{1-4}$ haloalkoxy;

each $R^y$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dC(O)NR^dR^e$, —$NR^d R^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl and $C_{3-6}$ cycloalkyl;

each $R^z$ is independently selected from the group consisting of halogen, —CN, —$R^i$, —$CO_2R^g$, —$CONR^gR^h$, —$C(O)R^g$, —$OC(O)NR^gR^h$, —$NR^hC(O)R^g$, —$NR^hC(O)_2R^i$, —$NR^gC(O)NR^gR^h$, —$NR^gR^h$, —$OR^g$, —$S(O)_2\ NR^gR^h$, —$X^1$—$R^j$, —$X^1$—$NR^gR^h$, —$X^1$—$CONR^gR^h$, —$X^1$—$NR^hC(O)R^g$, —$NHR^j$, —$NHCH_2R^j$, and tetrazole; wherein each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 2 additional heteroatoms as ring members selected from N, O or S and is optionally substituted with one or two oxo; each $R^i$ is independently selected from the group consisting of $C_{1-8}$ alkyl, $C_{1-8}$ haloalkyl and $C_{3-6}$ cycloalkyl; and each $R^j$ is selected from the group consisting of $C_{3-6}$ cycloalkyl, pyrrolinyl, piperidinyl, morpholinyl, tetrahydrofuranyl, and tetrahydropyranyl.

It shall be understood that when $R^1$ and $R^2$ are combined with the nitrogen atom to which each is attached to form a 6- to 11-membered monocyclic or fused bicyclic-heterocyclic ring, the 6- to 11-membered monocyclic or fused bicyclic-heterocyclic ring encompasses monocyclic heterocyclic rings fused with an aryl or a heteroaryl ring.

In formula I, the substituent $R^3$ is, in one embodiment, selected from the group consisting of H, methyl, ethyl, propyl, isopropyl, buty, isobutyl, sec-butyl, cyclopropyl, cyclopropylmethyl, cyclobutyl and cyclobutylmethyl.

In the descriptions herein, one of skill in the art will understand that the wavy line intersecting a bond is meant to identify the point of attachment of a given substituent or group to the remainder of the molecule.

As noted above, the subscripts m and n are each integers selected from 0, 1 and 2, and m+n is ≤3. When the subscript is 0, one of skill in the are will understand that a cyclic structure with ring vertex A is intended, but that adjacent ring vertices on either side of the parentheses are joined by a bond. Accordingly, the present invention includes the structures wherein the ring having A as a vertex is meant to include:

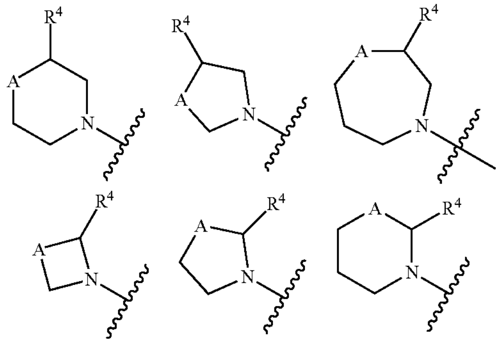

-continued

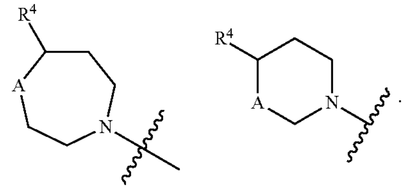

In one selected group of embodiments, m and n are both 0. In another selected group of embodiments, m and n are both 1. In yet another group of selected embodiments, m is 1 and n is 0. In still another group of embodiments, m is 1 and n is 2.

In still other selected embodiments, the ring having vertex A is represented by a formula selected from:

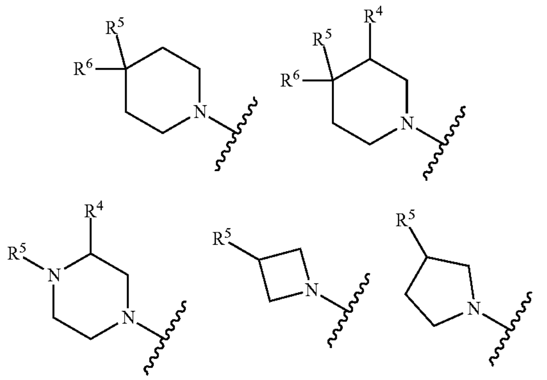

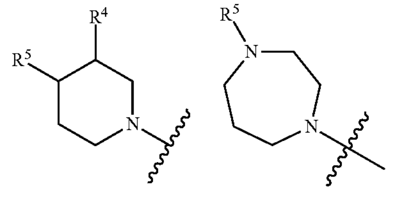

and

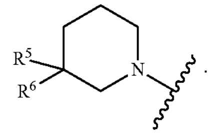

In one subgroup of embodiments, the compounds of formula (I) are represented by:

(Ia)

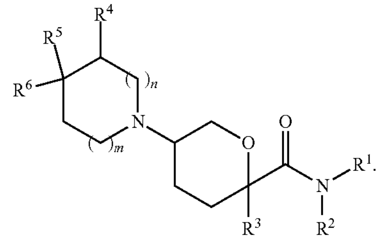

Within formula (Ia), a number of selected embodiments are provided as formulae Ia1, Ia2, Ia3, Ia4 and Ia5.

(Ia1)

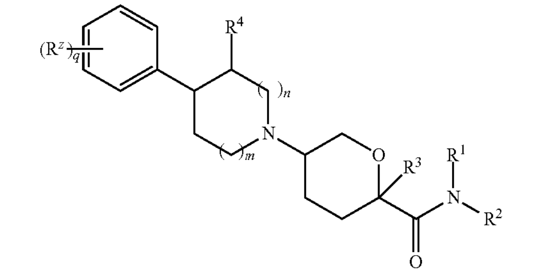

(Ia2)

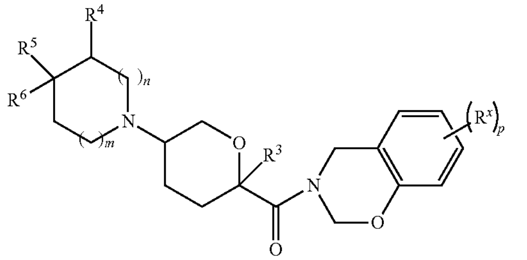

(Ia3)

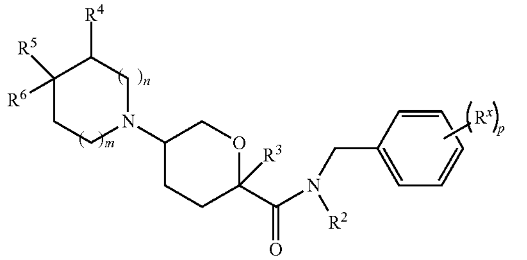

(Ia4)

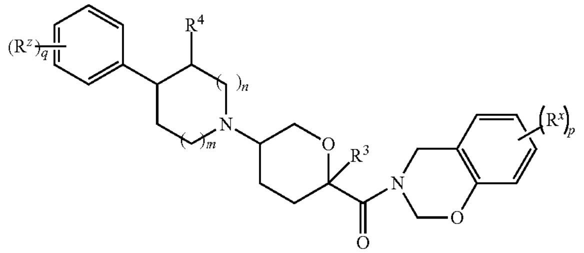

(Ia5)

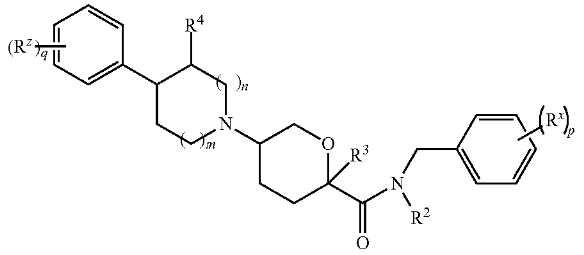

In each of formulae Ia, Ia1, Ia2, Ia3, Ia4 and Ia5, the noted substituents ($R^1$ through $R^6$, $R^x$ and $R^z$) and subscripts m and n have the meanings provided above with respect to formula I. The subscripts, p and q, have the following meanings: for Ia1, Ia4 and Ia5, the subscript q is an integer of from 0 to 5; for Ia2 and Ia4, the subscript p is an integer of from 0 to 4; and for Ia3 and Ia5, the subscript p is an integer of from 0 to 5.

In still other selected embodiments, the compounds provided herein are represented by formulae selected from:

(Ia1')

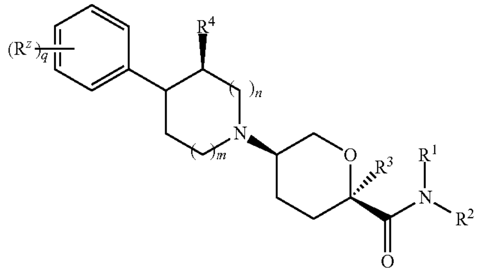

(Ia2')

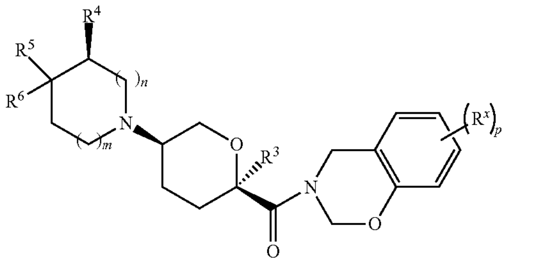

(Ia3')

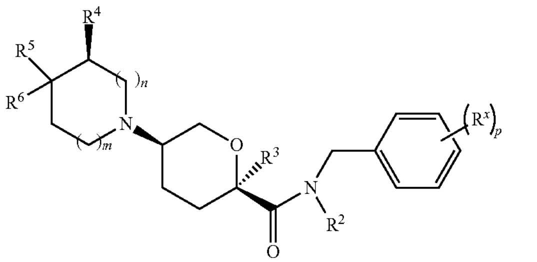

(Ia4')

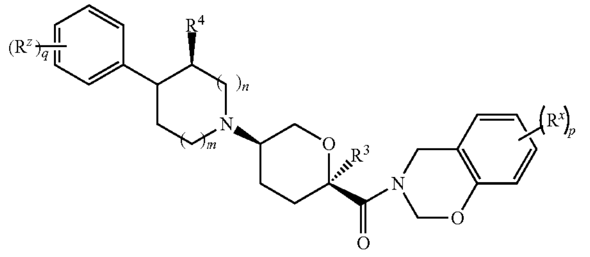

(Ia5')

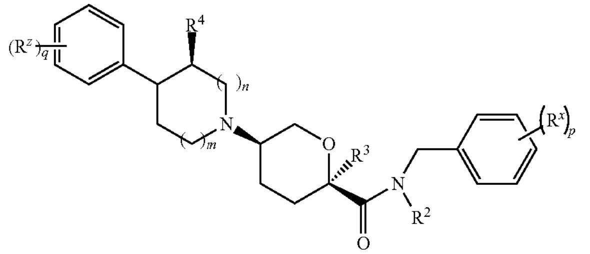

wherein each compound is substantially free of other stereoisomers, and wherein the noted substituents ($R^1$ through $R^6$, $R^x$ and $R^z$) and subscripts m and n have the meanings provided above with respect to formula I. The subscripts, p and q, have the following meanings: for Ia1', Ia4' and Ia5', the subscript q is an integer of from 0 to 5; for Ia2' and Ia4', the subscript p is an integer of from 0 to 4; and for Ia3' and Ia5', the subscript p is an integer of from 0 to 5.

In another group of embodiments of formula I, A is $C(R^5)(R^6)$, wherein $R^5$ and $R^6$ are combined to form a ring. Selected embodiments are provided as follows:

(Ib)

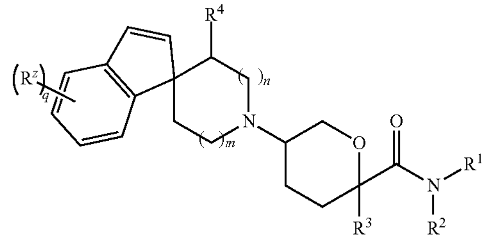

(Ib1)

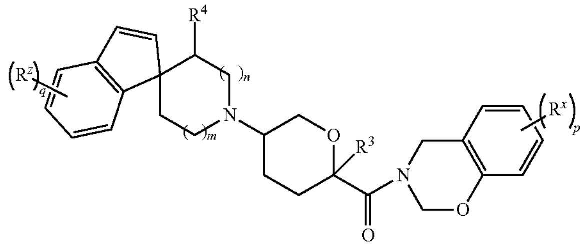

(Ib2)

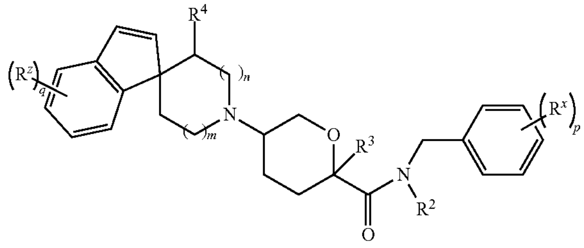

In each of formulae Ib, Ib1 and Ib2, the noted substituents ($R^1$ through $R^6$, $R^x$ and $R^z$) and subscripts m and n have the meanings provided above with respect to formula I. The subscripts, p and q, have the following meanings: for Ib, Ib1 and Ib2, the subscript q is an integer of from 0 to 5; for Ib1, the subscript p is an integer of from 0 to 4; and for Ib2, the subscript p is an integer of from 0 to 5.

In another group of embodiments of formula I, A is $NR^5$ (see formula Ic). Selected embodiments are provided as follows:

(Ic)

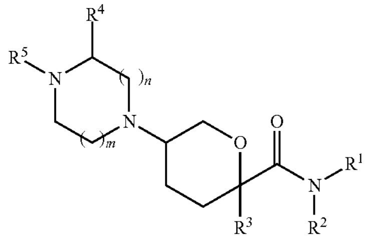

-continued (Ic1)

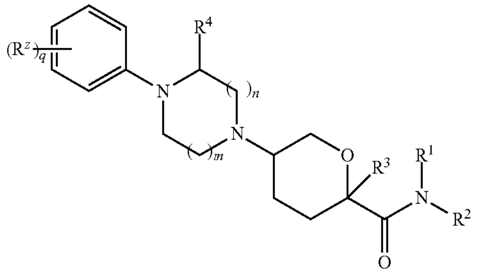

(Ic2)

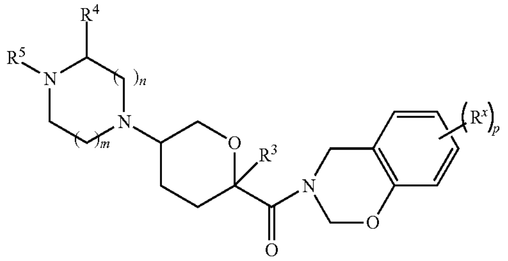

(Ic3)

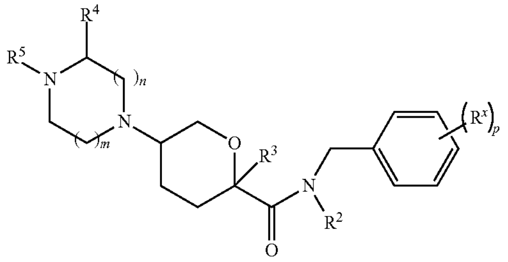

(Ic4)

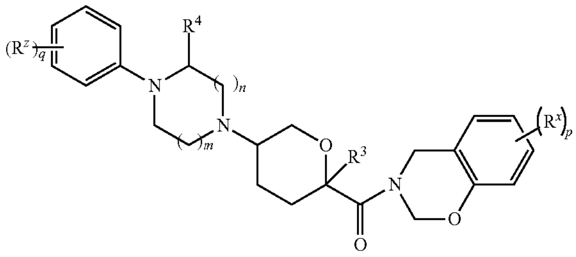

(Ic5)

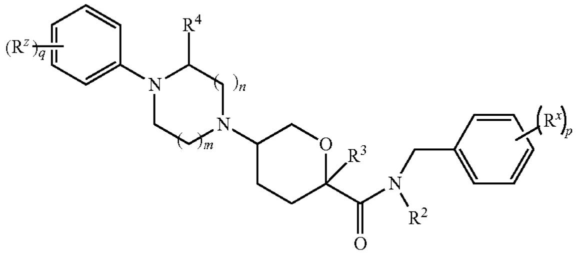

In each of formulae Ic, Ic1, Ic2, Ic3, Ic4 and Ic5, the noted substituents ($R^1$ through $R^6$, $R^x$ and $R^z$) and subscripts m and n have the meanings provided above with respect to formula I. The subscripts, p and q, have the following meanings: for Ic1, Ic4 and Ic5, the subscript q is an integer of from 0 to 5; for Ic2 and Ic4, the subscript p is an integer of from 0 to 4; and for Ic3 and Ic5, the subscript p is an integer of from 0 to 5.

In still other selected embodiments, the compounds provided herein are represented by formulae selected from:

(Ic1')

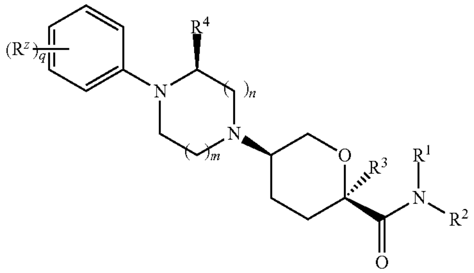

(Ic2')

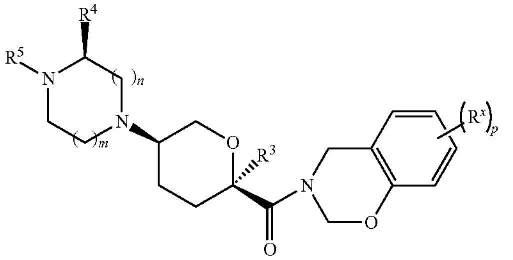

(Ic3')

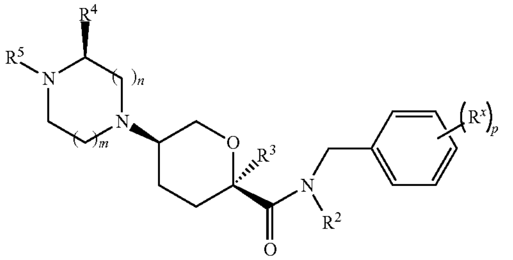

(Ic4')

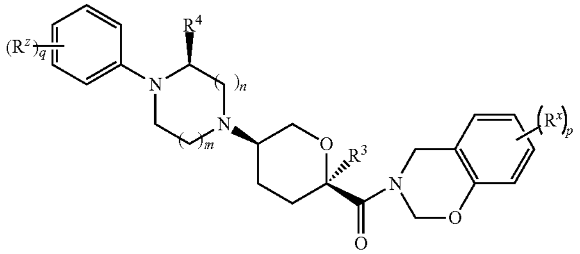

(Ic5')

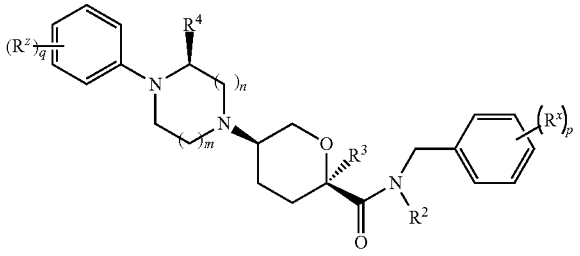

wherein each compound is substantially free of other stereoisomers, and wherein the noted substituents ($R^1$ through $R^6$, $R^x$ and $R^z$) and subscripts m and n have the meanings provided above with respect to formula I. The subscripts, p and q, have the following meanings: for Ic1', Ic4' and Ic5', the subscript q is an integer of from 0 to 5; for Ic2' and Ic4', the subscript p is an integer of from 0 to 4; and for Ic3' and Ic5', the subscript p is an integer of from 0 to 5.

Other selected embodiments, compounds are provided in each of I, Ia, Ia1, Ia1', Ib, Ic, Ic1 and Ic1', described above, wherein —$N(R^1)(R^2)$ is selected from:

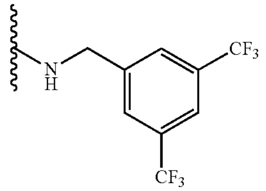
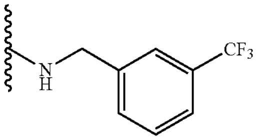
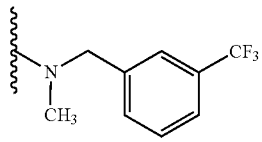
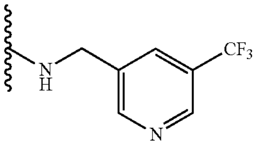
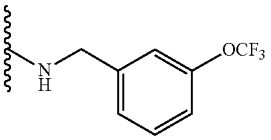
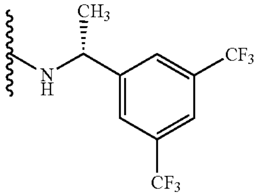
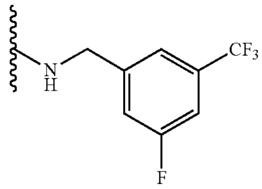
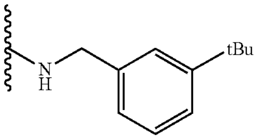
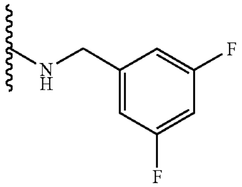
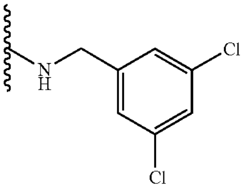
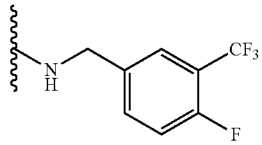
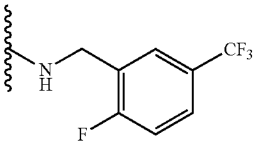
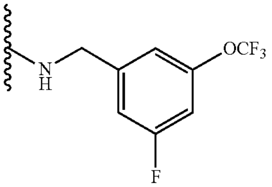
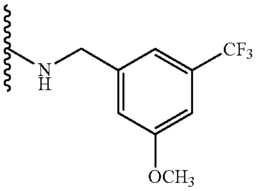
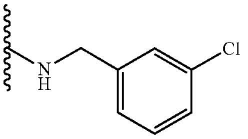
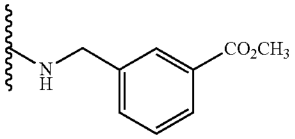
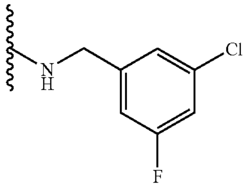
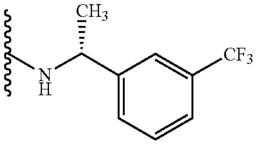

-continued
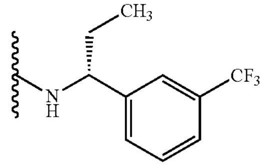
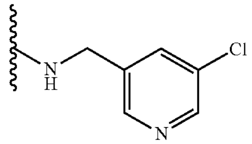
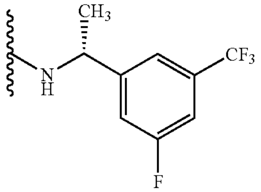
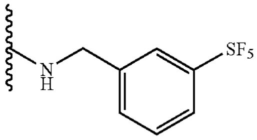
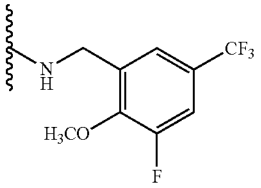
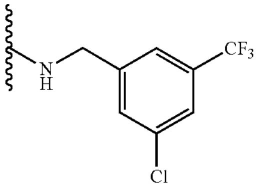
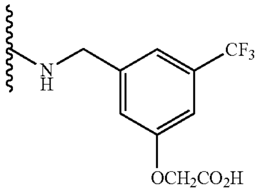
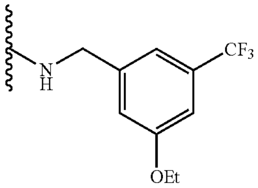
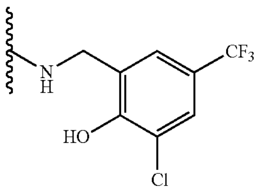
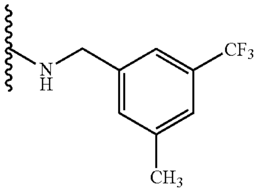
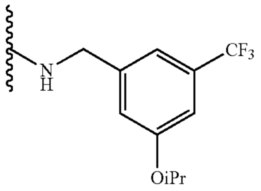
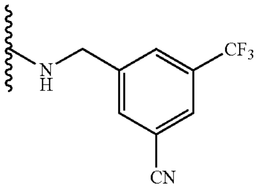
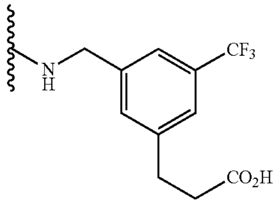
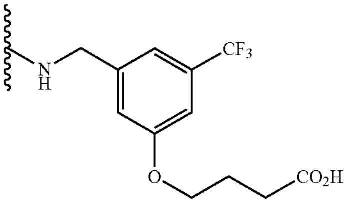
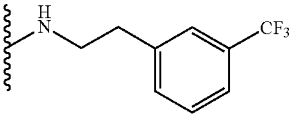
and
-continued
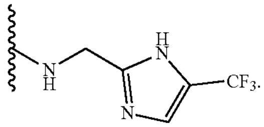
Still other selected embodiments, are provided in each of I, Ia, Ia1, Ia1', Ib, Ic, Ic1 and Ic1', described above, wherein —$N(R^1)(R^2)$ is selected from:
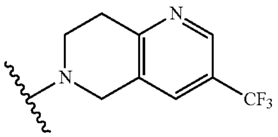
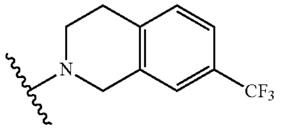
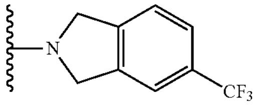
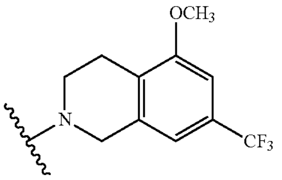
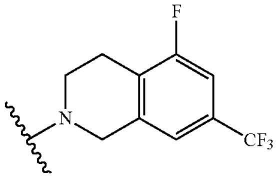
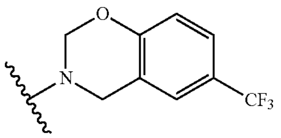
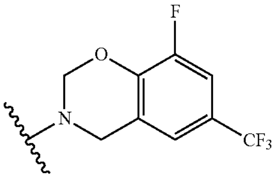
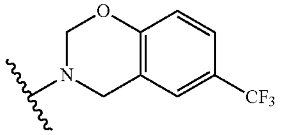
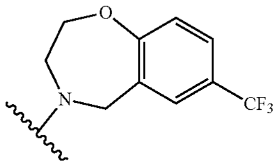
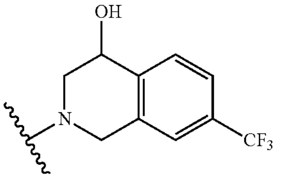
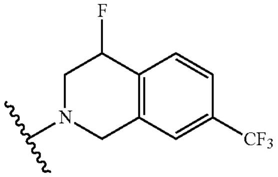
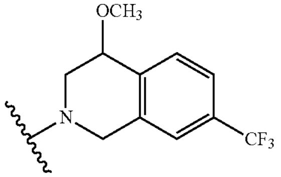
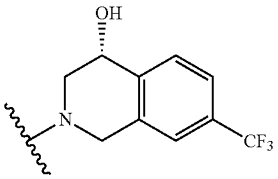
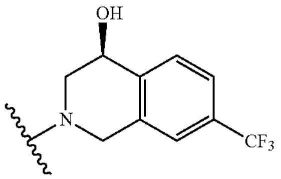
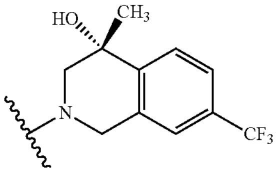
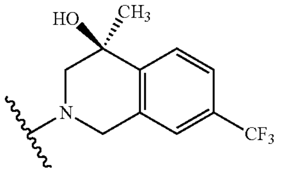

-continued

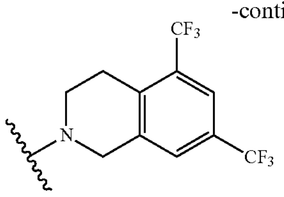
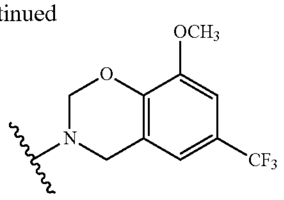
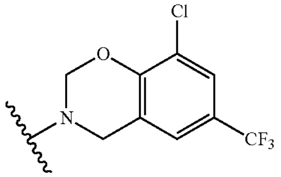
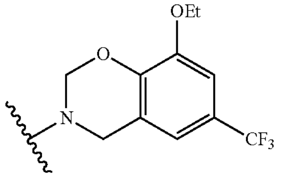
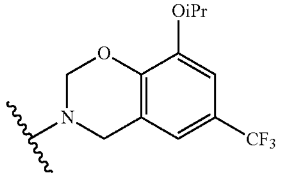
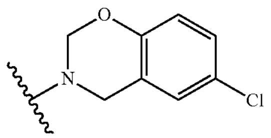
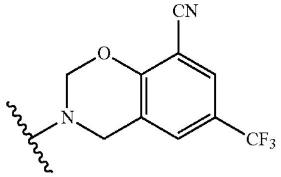
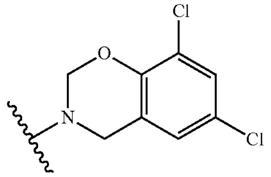
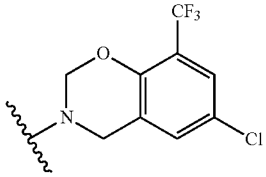
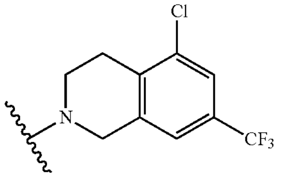
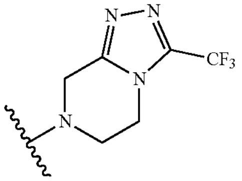
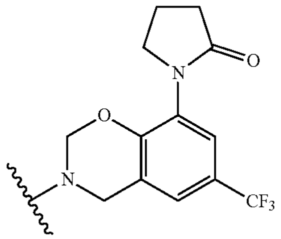

and

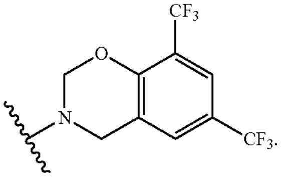

Yet other selected embodiments, are provided in each of I, Ia, Ia1, Ia1', Ib, Ic, Ic1 and Ic1', described above, wherein —N($R^1$)($R^2$) is selected from:

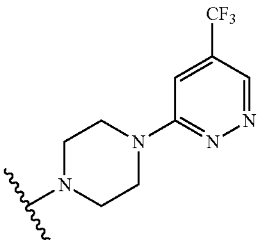
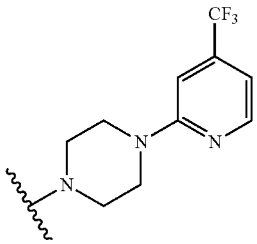

-continued

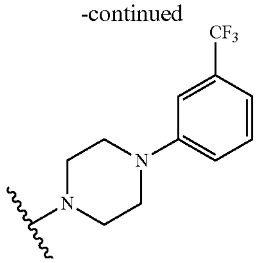
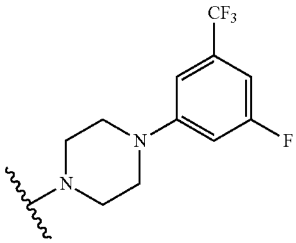

and

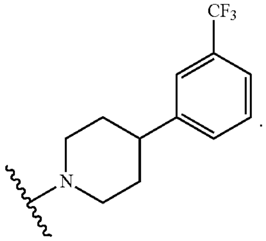

In some embodiments, compounds of formulae I, Ia, Ia2, Ia3, Ia2' and Ia3', are provided wherein A is C($R^5$)($R^6$), or is shown in the formula as C($R^5$)($R^6$), wherein $R^5$ is selected from aryl, aryloxy, arylamino, aryl-$C_{1-4}$ alkyl, heteroaryl, heteroaryloxy, heteroarylamino and heteroaryl-$C_{1-4}$ alkyl, wherein the aryl or heteroaryl groups or portions are selected from:

Group 1

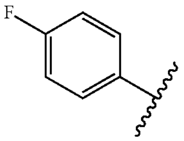
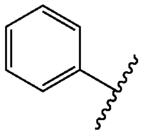
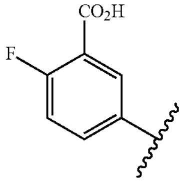
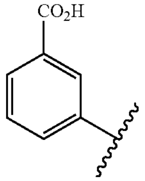
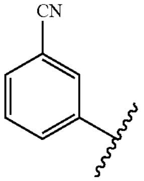
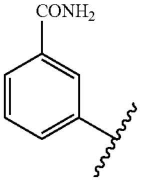
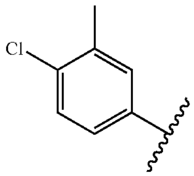
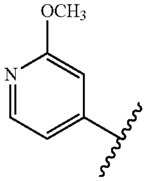
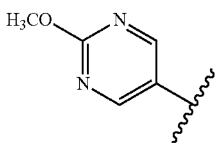
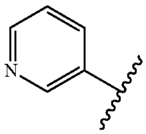
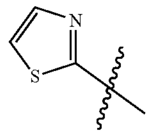
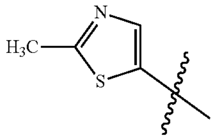

-continued

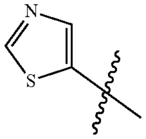 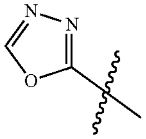 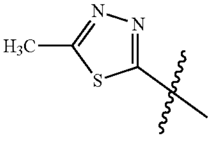

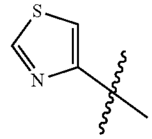 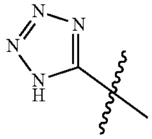 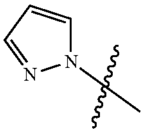

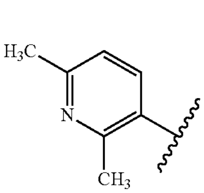 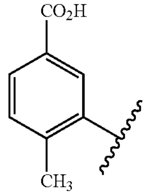 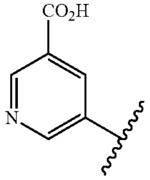

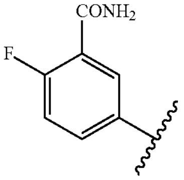 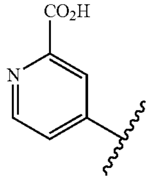 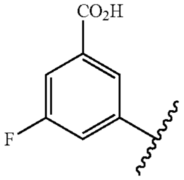

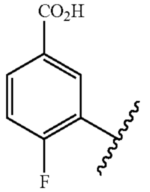 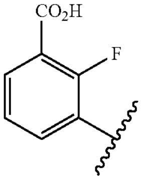 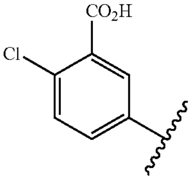

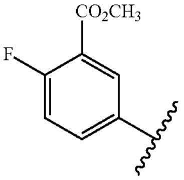 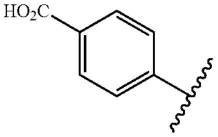

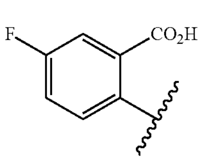 and 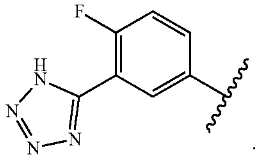 .

In certain selected embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from aryl, aryloxy, arylamino and aryl-$C_{1-4}$ alkyl, wherein the aryl group or portion is selected from:

Subgroup 1a

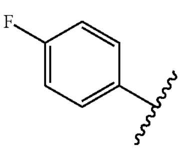 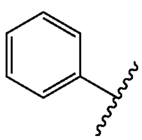 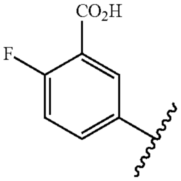

-continued

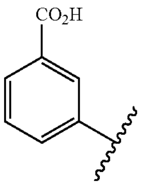 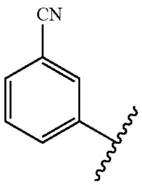 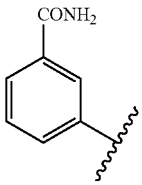

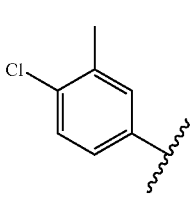 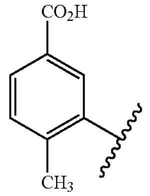 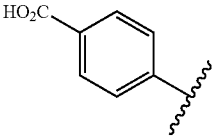

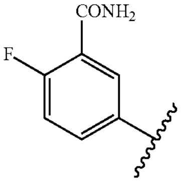 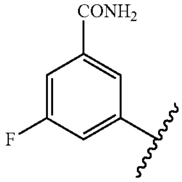 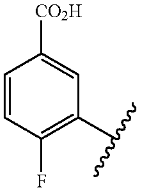

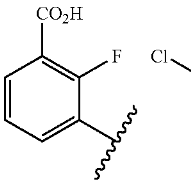 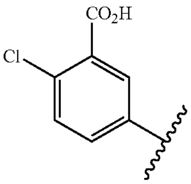 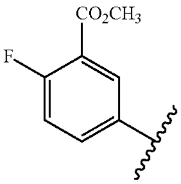

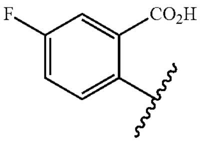 and 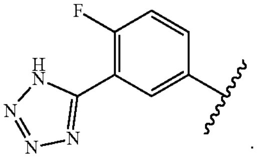 .

In still other selected embodiments, compounds of formulae I, Ia, Ia2, Ia3, Ia2' and Ia3', are provided wherein A is $C(R^5)(R^6)$, or is shown in the formula as $C(R^5)(R^6)$, wherein $R^5$ is selected from heteroaryl, heteroaryloxy, heteroarylamino and heteroaryl-$C_{1-4}$ alkyl, wherein the heteroaryl group or portion is selected from:

Subgroup 1b

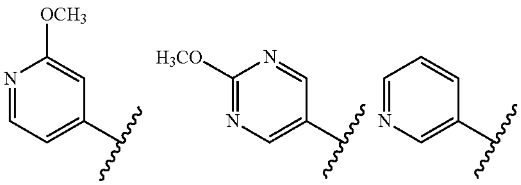

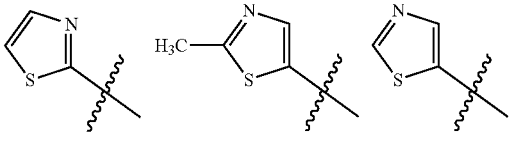

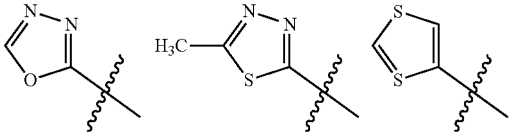

-continued

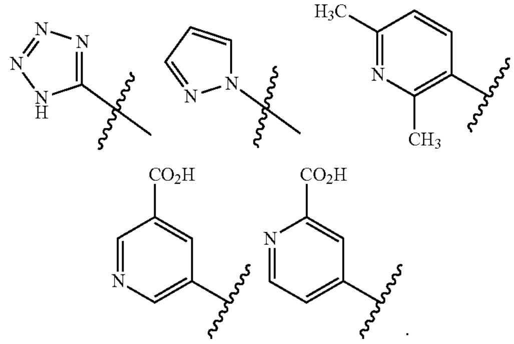

In some embodiments, compounds of formulae I, Ic, Ic2, Ic3, Ic2' and Ic3', are provided wherein A is $N(R^5)$, or is shown in the formula as $N(R^5)$, wherein $R^5$ is selected from aryl, aryl-$C_{1-4}$ alkyl, heteroaryl and heteroaryl-$C_{1-4}$ alkyl, wherein the aryl or heteroaryl groups or portions are selected from Group 1 above. In certain selected embodiments, compounds of formulae I, Ic, Ic2, Ic3, Ic2' and Ic3', are provided wherein A is $N(R^5)$, or is shown in the formula as $N(R^5)$, wherein $R^5$ is selected from aryl and aryl-$C_{1-4}$ alkyl, wherein the aryl group or portion is selected from Subgroup 1a, above. In still other selected embodiments, compounds of formulae I, Ic, Ic2, Ic3, Ic2' and Ic3', are provided wherein A is $N(R^5)$, or is shown in the formula as $N(R^5)$, wherein $R^5$ is selected from heteroaryl and heteroaryl-$C_{1-4}$ alkyl, wherein the heteroaryl group or portion is selected from Subgroup 1b, above.

In some embodiments, the CCR2 antagonist has the formula selected from the group consisting of

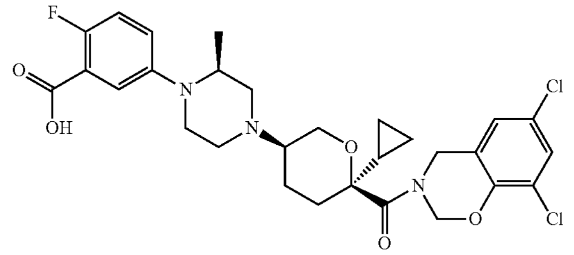

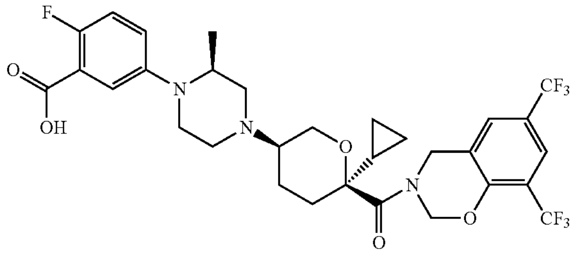

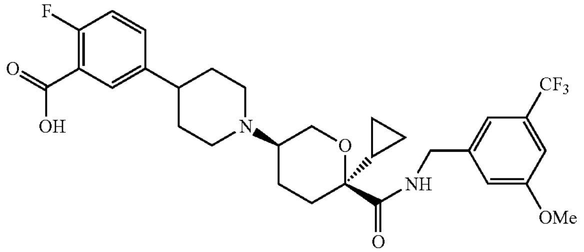

-continued

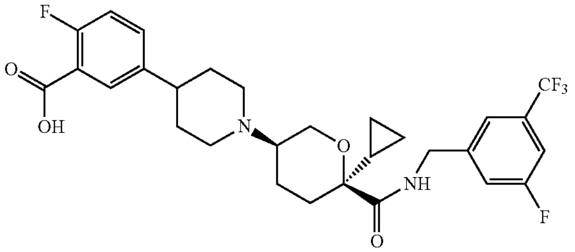

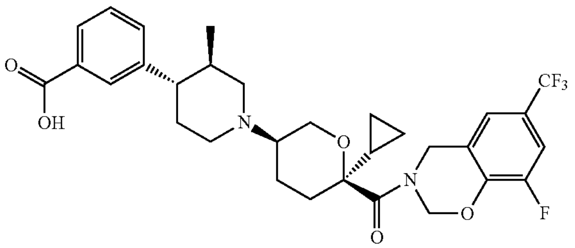

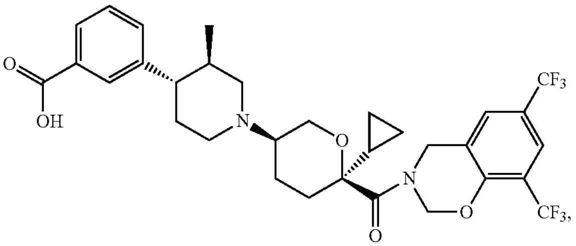

or a pharmaceutically acceptable salt thereof.

In some embodiments, the CCR2 antagonist has the formula of Compound 1

(Compound 1)

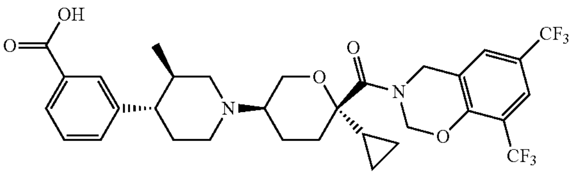

or a pharmaceutically acceptable salt thereof.

In some embodiments, the CCR2 antagonist has the formula of Compound 2

(Compound 2)

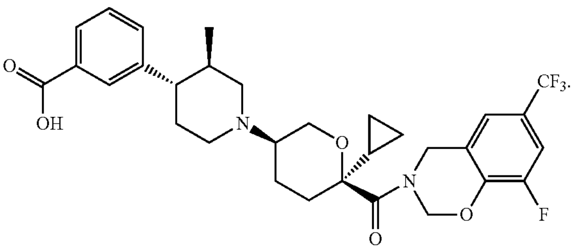

or a pharmaceutically acceptable salt thereof.

In some embodiments, the CCR2 antagonist has the formula of Compound 3

(Compound 3)

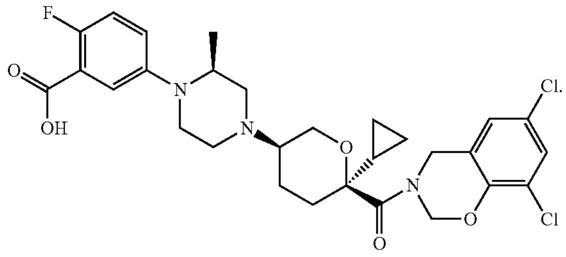

or a pharmaceutically acceptable salt thereof.

In some embodiments, the CCR2 antagonist is selected from the compounds or pharmaceutical compositions disclosed in US2016/0340356, stemming from application Ser. No. 15/158,713, filed on May 19, 2016 by ChemoCentryx, the content of which is incorporated herein for all purposes.

In some embodiments, the CCR2 chemokine receptor antagonist is selected from the group consisting of AZ889, AZD2423, NCB-8761, MK-0812, BMS-813160, NCB-003284, PF-04634817, BMS-741672, Cenicriviroc, CCX-140.

C. Methods of Administration

The term "therapeutically effective amount" means the amount of the subject compound that will elicit the biological or medical response of a cell, tissue, system, or animal, such as a human, that is being sought by the researcher, veterinarian, medical doctor or other treatment provider.

In general, treatment methods provided herein comprise administering to a patient an effective amount of a compound one or more compounds provided herein. In a preferred embodiment, the compound(s) of the invention are preferably administered to a patient (e.g., a human) orally or topically. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional nontoxic pharmaceutically acceptable carriers, adjuvants and vehicles appropriate for each rouse of administration. The present invention also contemplates administration of the compounds and compositions of the present invention in a depot formulation.

Dosage levels of the order of from about 0.1 mg to about 140 mg per kilogram of body weight per day are useful in the treatment or preventions of conditions involving pathogenic CCR2 activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In some embodiments, the treatment or prevention of conditions which require CCR2 receptor modulation, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

D. Combination Therapy

In treating, preventing, ameliorating, controlling or reducing solid tumor growth and metastases, the compounds of the present invention may be used in conjunction with the following: (1) cancer vaccination strategies, (2) immune-checkpoint modulators such as antagonistic antibodies against immune-checkpoint inhibitors (anti-PD1, anti-PD-L1, anti-CTLA4, anti-Tim3, anti-VISTA, anti-KIR) or agonistic antibodies against immune-accelators (anti-Lag3, anti-OX40, anti-ICOS, anti-4-1BB, (3) blocking or depleting antibodies against cell surface proteins commonly up-regulated in transformed cells (CEACAM1, Syndecan-2, GRP78), (4) anti-angiogenic therapies (anti-VEGF, anti-VEGFR, VEGFR small molecule inhibitors), (5) anti-lymphangiogenesis (blocking antibodies or inhibitors against VEGF, FDF2, PDGF as well as its respective receptors), (6) standard chemotherapeutic therapies (Gemcitabine, Paclitaxel, FOLFORINOX), (7) irradiation therapy, (8) other chemokine antagonists (CCR1, CCR4, CCR6, CXCR4, CXCR2, CXCR7 small molecule inhibitors, blocking antibodies, or depleting antibodies), (9) depleting antibodies against chemokines that activate the aforementioned chemokine receptors, (10) inhibitors targeting common somatic mutations in cancer such as those specifically targeting the following genes (BRAF, KRAS, NRAS, EGFR, CTNNB1, NOTCH1, PIK3CA, PTEN, APC, FLT3, IDH1, IDH2, KIT, TP53, JAK2). Combination therapy is also contemplated in methods of increasing the number CD8+ T cells in a solid tumor microenvironment and methods of reducing the number of macrophages in a solid tumor microenvironment.

In some embodiments, the compounds of the present invention may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing anti-inflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

In some embodiments, the immune checkpoint inhibitor is a PD-1 and/or PD-L1 inhibitor. In some embodiments, a PD-L1 inhibitor can be durvalumab or atezolizumab or avelumab or BMS-936559 (MDX-1105) or ALN-PDL or TSR-042 or KD-033 or CA-170 or CA-327 or STI-1014 or MEDI-0680 or KY-1003. Durvalumab (MEDI4736) is a human monoclonal antibody directed against PD-L1. Atrexolizumab (MPDL3280A) is a fully humanized, engineered IgG1 monoclonal antibody against PD-L1. Avelumab (MSB0010718C) is a fully humanized, engineered IgG1 monoclonal antibody against PD-L1. BMS-936559 (MDX-1105) is a fully human IgG4 monoclonal antibody against PD-L1. ALN-PDL is an inhibitory RNA (RNAi) targeting PD-L1. TSR-042 refers to an engineered chimeric antibody that is directed against the PD-1/PD-L1 pathway. KD-033 refers to a bifunctional anti-PD-L1/IL-15 fusion protein wherein the anti-PD-L1 antibody is linked at its tail to the cytokine IL-15 by the sushi domain of the IL-15 receptor. CA-170 refers to a small molecule antagonist of PD-L1 and VISTA. STI-1014 refers to an anti-PD-L1 antibody. KY-1003 is a monoclonal antibody against PD-L1. CA-327 refers to a small molecule antagonist of PD-L1 and TIM3.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-Ll/BCMA bispecific antibody (Immune Pharmaceuticals), PD-1/Ox40 targeting bispecific antibody (Immune Pharmaceuticals), BMS-936559, anti-PD-1NEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some embodiments, a PD-1 inhibitor can be pembrolizumab or nivolumab or IBI-308 or mDX-400 or BGB-108 or MEDI-0680 or SHR-1210 or PF-06801591 or PDR-001 or GB-226 or STI-1110. Nivolumab (also known as OPDIVO™, MDX-1106, BMS-936558, and ONO-4538) is a human IgG4 monoclonal antibody against PD-1. Pembrolizumab (also known as KEYTRUDA®, lambrolizumab, and MK-34) is a humanized IgG4 kappa isotype monoclonal antibody against PD-1. IBI-308 refers to a monoclonal antibody directed to PD-1. mDX-400 refers to a mouse antibody against PD-1. BGB-108 is a humanized monoclonal antibody against PD-1. MEDI-0680 (AMP-514) is a humanized IgG4 monoclonal antibody against PD-1. SHR-1210 refers to a monoclonal antibody against PD-1. PF-06801591 is a monoclonal antibody against PD-1. PDR-001 refers to a monoclonal antibody against PD-1. GB-226 refers to a monoclonal antibody against PD-1. STI-1110 refers to a monoclonal antibody against PD-1.

In some embodiments, the PD-1 inhibitor is RPM1-14.

In some embodiments, the PD-1 inhibitor is an antibody selected from Nivolumab, Pembrolizumab, and Pidilizumab.

The anti-PD-1 antibodies, and antibody fragments described herein encompass proteins having amino acid sequences that vary from those of the described antibodies, but that retain the ability to bind PD-1.

In some embodiments, the anti-PD-1 antibodies include bispecific antibodies and antibody-like therapeutic proteins including DARTs®, DUOBODIES®, BITES®, XmAbs®, TandAbs®, Fab derivatives, and the like that bind to PD-1.

The anti-PD-L1 antibodies and antibody fragments described herein encompass proteins having amino acid sequences that vary from those of the described antibodies, but that retain the ability to bind PD-L1. Such variant antibodies and fragments thereof can comprise one or more additions, deletions, or substitutions of amino acids when compared to the parent sequence, but exhibit biological activity that is essentially equivalent or essentially bioequivalent to that of the described antibodies.

In some embodiments, the anti-PD-L1 antibodies include bispecific antibodies and antibody-like therapeutic proteins including DARTs®, DUOBODIES®, BITES®, XmAbs®, TandAbs®, Fab derivatives, and the like that bind to PD-L1.

Non-limiting examples of additional PD-1/PD-L1 pathway inhibitors are described in, e.g., Chen and Han, *Jour Clin Invest,* 2015, 125(9):3384-3391, U.S. Pat. Nos. 8,168,757; 8,354,509; 8,552,154; 8,741,295; and 9,212,224; U.S. Patent App. Publ. Nos. 2014/0341917; 2015/0203580 and 2015/0320859; International Patent App. Publ. No. WO2015/026634.

In some embodiments, the immune checkpoint inhibitor is a CTLA-4 inhibitor. A number of CTLA-4 inhibitors are known in the art. In some embodiments, the CTLA-4 inhibitor is an antibody. In some embodiments the CTLA-4 inhibitor antibody is selected from Ipilimumab, Tremelimumab, AGEN1884, and AGEN2041. In some embodiments, the CTLA-4 inhibitor antibody is Ipilimumab. In some embodiments, the CTLA-4 inhibitor antibody is Tremelimumab. In some embodiments, the CTLA-4 inhibitor antibody is AGEN1884. In some embodiments, the CTLA-4 inhibitor antibody is AGEN2041.

A biological product, e.g., an antibody or a fragment thereof, is considered a biosimilar if, for example, the biological product is highly similar to an already FDA-approved biological product, known as the reference product. A biosimilar has no clinically meaningful differences in terms of safety and effectiveness from the reference product. A biosimilar can also have the same mechanism of action, route of administration, dosage form, and strength as its reference product.

Two biological products, e.g., antibodies or fragments thereof, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two biological products (e.g., two antibodies or fragments thereof) are bioequivalent if there are no clinically meaningful differences in their safety, purity, or potency.

In other embodiments, two biological products (e.g., two antibodies or fragments thereof) are bioequivalent if a patient can be switched one or more times between the reference product and the biological product without an expected increase in the risk of adverse effects, including a clinically significant change in immunogenicity, or diminished effectiveness, as compared to continued therapy without such switching.

In yet other embodiments, two biological products (e.g., two antibodies or fragments thereof) are bioequivalent if they both act by a common mechanism of action for the condition of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Biobetter variants of the antibodies described herein may be based on an existing reference antibody specific for an target antigen, e.g., PD-1 or PD-L1, which has undergone changes such that, for example, it has a higher binding affinity to its target antigen and/or binds to a different epitope than the reference antibody, or has more desirable therapeutic efficacy, expression and/or biophysical characteristics.

In some embodiments, the PD-1 and/or PD-L1 inhibitor is a small molecule PD-1/PD-L1 inhibitor of having the formula:

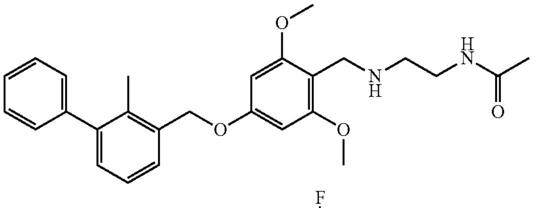

or

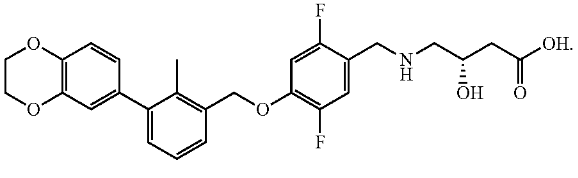

In some embodiments, the PD-1 and/or PD-L1 inhibitor is a small molecule PD-1/PD-L1 inhibitor having the formula (II)

(II)

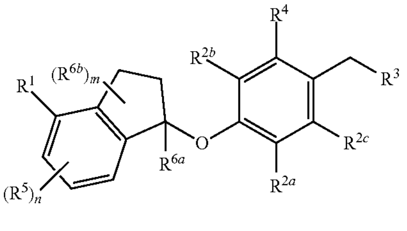

or a pharmaceutically acceptable salt thereof; wherein:

$R^1$ is selected from the group consisting of halogen, $C_{5-8}$ cycloalkyl, $C_{6-10}$ aryl and thienyl, wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —$C(O)R^a$, —$OC(O)NR^aR^b$, —$NR^bC(O)R^a$, —$NR^bC(O)_2R^c$, —$NR^a$—$C(O)NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$NR^aR^b$, —$X^1$—$CO_2R^a$, —$X^1$—$CONR^aR^b$, —$SF_5$, and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^x$ substituents are on adjacent atoms, they are combined to form a fused five, six or seven-membered carbocyclic or heterocyclic ring optionally substituted with from 1 to 3 substituents independently selected from halo, oxo, $C_{1-8}$ haloalkyl and $C_{1-8}$ alkyl;

each $R^{2a}$, $R^{2b}$ and $R^{2c}$ is independently selected from the group consisting of H, halogen, —CN, —$R^d$, —$CO_2R^e$, —$CONR^eR^f$, —$C(O)R^e$, —$OC(O)NR^eR^f$, —$NR^fC(O)R^e$, —$NR^fC(O)_2R^d$, —$NR^e$—$C(O)NR^eR^f$, —$NR^eR^f$, —$OR^e$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^2$, —$X^2$—$CONR^eR^f$, —$SF_5$, —$S(O)_2NR^eR^f$, $C_{6-10}$ aryl and $C_{5-10}$ heteroaryl, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O and S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of —$NR^gR^h$ and $C_{4-12}$ heterocyclyl, wherein the $C_{4-12}$ heterocyclyl is optionally substituted with 1 to 6 $R^y$;

each $R^y$ is independently selected from the group consisting of halogen, —CN, —$R^i$, —$CO_2R^j$, —$CONR^jR^k$, —$CONHC_{1-6}$ alkyl-OH, —$C(O)R^j$, —$OC(O)NR^jR^k$, —$NR^jC(O)R^k$, —$NR^jC(O)_2R^k$, CONOH, $PO_3H_2$, —$NR^j$—$C_{1-6}$ alkyl-$C(O)_2R^k$, —$NR^jC(O)NR^jR^k$, —$NR^jR^k$, —$OR^j$, —$S(O)_2NR^jR^k$, —O—$C_{1-6}$alkyl-$OR^j$, —O—$C_{1-6}$ alkyl-$NR^jR^k$, —O—$C_{1-6}$ alkyl-$CO_2R^j$, —O—$C_{1-6}$ alkyl-$CONR^jR^k$, —$C_{1-6}$ alkyl-$OR^j$, —$C_{1-6}$ alkyl-$NR^jR^k$, —$C_{1-6}$ alkyl-$CO_2R^j$, —$C_{1-6}$ alkyl-$CONR^jR^k$, and $SF_5$, wherein the $C_{1-6}$ alkyl portion of $R^y$ is optionally further substituted with OH, $SO_2NH_2$, $CONH_2$, CONOH, $PO_3H_2$, COO—$C_{1-8}$alkyl or $CO_2H$, wherein each $R^j$ and $R^k$ is independently selected from hydrogen, $C_{1-8}$ alkyl optionally substituted with 1 to 2 substituents selected from OH, $SO_2NH_2$, $CONH_2$, CONOH, $PO_3H_2$, COO—$C_{1-8}$alkyl or $CO_2H$, and $C_{1-8}$ haloalkyl optionally substituted with 1 to 2 substituents selected from OH, $SO_2NH_2$, $CONH_2$, CONOH, $PO_3H_2$, COO—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of —OH, $C_{1-8}$ alkyl, $C_{2-8}$ alkenyl, and $C_{1-8}$ haloalkyl each of which may be optionally substituted with OH, $SO_2NH_2$, $CONH_2$, CONOH, $PO_3H_2$, COO—$C_{1-8}$alkyl or $CO_2H$;

$R^g$ is selected from the group consisting of H, $C_{1-8}$ haloalkyl and $C_{1-8}$ alkyl;

$R^h$ is selected from —$C_{1-8}$ alkyl, $C_{1-8}$ haloalkyl, $C_{1-8}$ alkyl-COOH, $C_{1-8}$ alkyl-OH, $C_{1-8}$ alkyl-$CONH_2$, $C_{1-8}$ alkyl-$SO_2NH_2$, $C_{1-8}$ alkyl-$PO_3H_2$, $C_{1-8}$ alkyl-CONOH, $C_{1-8}$ alkyl-$NR^{h1}R^{h2}$, —C(O)—$C_{1-8}$alkyl, —C(O)—$C_{1-8}$ alkyl-OH, —C(O)—$C_{1-8}$alkyl-COOH, $C_{3-10}$ cycloalkyl, —$C_{3-10}$ cycloalkyl-COOH, —$C_{3-10}$ cycloalkyl-OH, $C_{4-8}$ heterocyclyl, —$C_{4-8}$ heterocyclyl-COOH, —$C_{4-8}$ heterocyclyl-OH, —$C_{1-8}$ alkyl-$C_{4-8}$ heterocyclyl, —$C_{1-8}$ alkyl-$C_{3-10}$ cycloalkyl, $C_{5-10}$ heteroaryl, —$C_{1-8}$alkyl-$C_{5-10}$ heteroaryl, $C_{10}$ carbocyclyl, —$C_{1-8}$ alkyl-$C_{6-10}$ aryl, —$C_{1-8}$ alkyl-(C═O)—$C_{6-10}$ aryl, —$C_{1-8}$ alkyl-NH(C═O)—$C_{1-8}$ alkenyl, —$C_{1-8}$ alkyl-NH(C═O)—$C_{1-8}$ alkyl, —$C_{1-8}$ alkyl-NH(C═O)—$C_{1-8}$ alkynyl, —$C_{1-8}$ alkyl-(C═O)—NH—$C_{1-8}$ alkyl-COOH, and —$C_{1-8}$ alkyl-(C═O)—NH—$C_{1-8}$ alkyl-OH optionally substituted with $CO_2H$; or $R^h$ combined with the N to which it is attached is a mono-, di- or tri-peptide comprising 1-3 natural amino acids and 0-2 non-natural amino acids, wherein the non-natural amino acids have an alpha carbon substituent selected from the group consisting of $C_{2-4}$ hydroxyalkyl, $C_{1-3}$ alkyl-guanidinyl, and $C_{1-4}$ alkyl-heteroaryl, the alpha carbon of each natural or non-natural amino acids are optionally further substituted with a methyl group, and the terminal moiety of the mono-, di-, or tri-peptide is selected from the group consisting of C(O)OH, C(O)O—$C_{1-6}$ alkyl, and $PO_3H_2$, wherein $R^{h1}$ and $R^{h2}$ are each independently selected from the group consisting of H, $C_{1-6}$ alkyl, and $C_{1-4}$ hydroxyalkyl;

the $C_{1-8}$ alkyl portions of $R^h$ are optionally further substituted with from 1 to 3 substituents independently selected from OH, COOH, $SO_2NH_2$, $CONH_2$, CONOH, COO—$C_{1-8}$ alkyl, $PO_3H_2$ and $C_{5-6}$ heteroaryl optionally substituted with 1 to 2 $C_{1-3}$ alkyl substituents, the $C_{10}$ carbocyclyl, $C_{5-10}$ heteroaryl and the $C_{6-10}$ aryl portions of $R^h$ are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$alkyl-$PO_3H_2$, $C_{1-4}$alkyl-COOH, and phenyl and the $C_{4-8}$ heterocyclyl and $C_{3-10}$ cycloalkyl portions of $R^h$ are optionally substituted with 1 to 4 $R^w$ substituents;

each $R^w$ substituent is independently selected from $C_{1-4}$ alkyl, $C_{1-4}$ alkyl-OH, $C_{1-4}$ alkyl-COOH, $C_{1-4}$ alkyl-$SO_2NH_2$, $C_{1-4}$ alkyl $CONH_2$, $C_{1-4}$ alkyl-CONOH, $C_{1-4}$ alkyl-$PO_3H$, OH, COO—$C_{1-8}$ alkyl, COOH, $SO_2NH_2$, $CONH_2$, CONOH, $PO_3H_2$ and oxo;

$R^4$ is selected from the group consisting of O—$C_{1-8}$ alkyl, O—$C_{1-8}$ haloalkyl, O—$C_{1-8}$ alkyl-$R^z$, $C_{6-10}$ aryl, $C_{5-10}$ heteroaryl, —O—$C_{1-4}$ alkyl-$C_{6-10}$aryl and —O—$C_{1-4}$ alkyl-$C_{5-10}$ heteroaryl, wherein the $C_{6-10}$ aryl and the $C_{5-10}$ heteroaryl are optionally substituted with 1 to 5 $R^z$;

each $R^z$ is independently selected from the group consisting of halogen, —CN, —$R^m$, —$CO_2R^n$, —$CONR^nR^p$, —$C(O)R^n$, —$OC(O)NR^nR^p$, —$NR^nC(O)R^p$, —$NR^nC(O)_2R^m$, —$NR^n$—$C(O)NR^nR^p$, —$NR^nR^p$, —$OR^n$, —O—$X^3$—$OR^n$, —O—$X^3$—$NR^nR^p$, —O—$X^3$—$CO_2R^n$, —O—$X^3$—$CONR^nR^p$, —$X^3$—$OR^n$, —$X^3$—$NR^nR^p$, —$X^3$—$CO_2R^n$, —$X^3$—$CONR^nR^p$, —$SF_5$, —$S(O)_2R^nR^p$, —$S(O)_2NR^nR^p$, and three to seven-membered carbocyclic or four to seven-membered heterocyclic ring wherein the three to seven-membered carbocyclic or four to seven-membered heterocyclic ring is optionally substituted with 1 to 5 $R^t$, wherein each $R^t$ is independently selected from the group consisting of $C_{1-8}$ alkyl, $C_{1-8}$haloalkyl, —$CO_2R^n$, —$CONR^nR^p$, —$C(O)R^n$, —$OC(O)NR^nR^p$, —$NR^nC(O)R^p$, —$NR^nC(O)_2R^m$, —$NR^n$—$C(O)NR^nR^p$, —$NR^nR^p$, —$OR^n$, —O—$X^3$—$OR^n$, —O—$X^3$—$NR^nR^p$, —O—$X^3$—$CO_2R^n$, —O—$X^3$—$CONR^nR^p$, —$X^3$—$OR^n$, —$X^3$—$NR^nR^p$, —$X^3$—$CO_2R^n$, —$X^3$—$CONR^nR^p$, —$SF_5$, and —$S(O)_2NR^nR^p$;

wherein each $X^3$ is a $C_{1-4}$ alkylene; each $R^n$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^m$ is independently selected from the group consisting of $C_{1-8}$ alkyl, $C_{2-8}$ alkenyl, and $C_{1-8}$ haloalkyl; and optionally when two $R^z$ substituents are on adjacent atoms, they are combined to form a fused five or six-membered carbocyclic or heterocyclic ring optionally substituted with oxo;

n is 0, 1, 2 or 3;

each $R^5$ is independently selected from the group consisting of halogen, —CN, —$R^q$, —$CO_2R^r$, —$CONR^rR^s$, —$C(O)R^r$, —$OC(O)NR^rR^s$, —$NR^rC(O)R^s$, —$NR^rC(O)_2R^q$, —$NR^r$—$C(O)NR^rR^s$, —$NR^rR^s$, —$OR^r$, —O—$X^4$—$OR^r$, —O—$X^4$—$NR^rR^s$, —O—$X^4$—$CO_2R^r$, —O—$X^4$—$CONR^rR^s$, —$X^4$—$OR^r$, —$X^4$—$NR^rR^s$, —$X^4$—$CO_2R^r$, —$X^4$—$CONR^rR^s$, —$SF_5$, —$S(O)_2NR^rR^s$, wherein each $X^4$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^q$ is independently selected from the group consisting of $C_{1-8}$ alkyl, and $C_{1-8}$ haloalkyl;

$R^{6a}$ is selected from the group consisting of H, $C_{1-4}$ alkyl and $C_{1-4}$ haloalkyl;

each $R^{6b}$ is independently selected from the group consisting of F, $C_{1-4}$ alkyl, O—$R^u$, $C_{1-4}$ haloalkyl, $NR^uR^v$, wherein each $R^u$ and $R^v$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; and m is 0, 1, 2, 3 or 4.

In some embodiments, the small molecule PD-1/PD-L1 inhibitor is selected from the compounds or pharmaceutical compositions disclosed in WO 2018/005374 filed by ChemoCentryx on Jun. 26, 2017. The contents of which is incorporated herein for all purposes.

The PD-1 and/or PD-L1 inhibitors of the present disclosure can be formulated to retard the degradation of the compound or antibody or to minimize the immunogenicity of the antibody. A variety of techniques are known in the art to achieve this purposes.

In the combination therapy described herein, the CCR2 antagonist can be formulated together with the additional therapeutic agent or separately. Both the CCR2 antagonist and the additional therapy will be formulated in suitable dosage unit formulations (either alone or together) containing conventional nontoxic pharmaceutically acceptable carriers, adjuvants and vehicles appropriate for each rouse of administration. It will be understood, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

Biological products such as antibodies may be constituted in a pharmaceutical composition containing one or antibodies or a fragment thereof and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

In some embodiments, the therapeutic compound and agent are each provided in an amount that would be sub-therapeutic if provided alone or without the other. Those of skill in the art will appreciate that "combinations" can involve combinations in treatments (i.e., two or more drugs can be administered as a mixture, or at least concurrently or at least introduced into a subject at different times but such that both are in a subject at the same time).

Likewise, compounds, agents and compositions of the present invention may be used in combination with other drugs that are used in the treatment, prevention, suppression or amelioration of cancer. Such other drugs may be administered, by a route and in an amount commonly used therefor, contemporaneously or sequentially with a compound, agent or composition of the present invention. When a compound, agent or composition of the present invention is used contemporaneously with one or more other drugs, a pharmaceutical composition containing such other drugs in addition to the compound, agent or composition of the present invention is preferred. Accordingly, pharmaceutical compositions can include those that also contain one or more other active ingredients or therapeutic agents, in addition to a compound, agent or composition of the present invention.

Combination therapy includes co-administration of the CCR2 antagonist and an additional therapeutic agent, sequential administration of the CCR2 antagonist and an additional therapeutic agent, administration of a composition containing the CCR2 antagonist and an additional therapeutic agent 1 inhibitor, or simultaneous administration of separate compositions such that one composition contains the CCR2 antagonist and another composition contains an additional therapeutic agent.

IV. EXAMPLES

The following examples are offered to illustrate, but not to limit, the claimed invention.

Materials & Methods

Animals and cell lines. Female C57BL/6 mice (6-8 weeks old) were purchased from Charles River (Hollister, CA) and housed in animal facilities at University of California Davis (UCDAVIS), Sacramento, CA. All animal experiments were conducted in accordance with the guidelines and approval of the Institutional Animal Care and Usage Committee at UCDAVIS. The MBL2 cell line is an established cell line derived from Moloney MuLV-induced T-cell lymphoma in C57BL/6 mice, in which the gag gene was deleted from the genome in order to lower virus-dependent immunogenicity. MBL2 cells were cultured in DMEM (Invitrogen, Carlsbad, CA) with 10% heat-inactivated FBS.

Establishment of MBL2 tumors in mice. The method of establishing mouse ear skin tumors was previously described [28]. Briefly, PBS-washed MBL2 cells ($4\times10^5$ in 20 μl PBS) were injected into the dermal space under the central dorsal surface of the ears and above the cartilage plane using a 28 g needle. Mice were then topically treated one time with DNFB (1-Fluoro-2,4-dinitrobenzene, 0.5% in a vehicle consisting of 4:1 (v/v) acetone and olive oil, 10 μl/ear) (Sigma, St. Louis, CA) on dorsal ear skins. Tumor growth was assessed for maximum ear thickness using a digital caliper, or by weight for the whole tumor-bearing ears removed from ear baseline. The endpoint determination is based on the allowed maximal ear tumor size, or local erosion and bleeding, which usually occurred within two weeks after implantation.

Tumor treatment by CCR2 antagonist and/or anti-PD1. Small molecule compounds, Compound 1, either in a high concentration (6 mg/ml) or a low concentration (2 mg/ml), as well as vehicle control were all provided by ChemoCentryx (Mountain View, CA) in a lab-ready formulation. In therapeutic application, oral administration through gavage of Compound 1 or vehicle started on the same day of MBL2 cell inoculation, usually two hours apart. Compound 1 was adminstrated once a day (60 mg/kg for high dose or 20 mg/kg for low dose) for up to two weeks following tumor implantation. Mice were euthanized on day 3 or day 7 for analysis of early immune responses to the treatment. For tumor treatment with anti-PD1, in vivo MAb anti-mouse PD-1 (CD279) and rat-IgG2a (BioXcell, West Lebanon, NH) were injected via IP (10 mg/kg per mouse) three times a week starting on the same day of tumor implantation. For combination therapy, the above single agent regimen was kept the same.

H&E and Histoimmunochemistry. After mouse ear tumors were surgically removed at the ear base, the ear sample was cut into two parts along the long axis and placed in RNA later for RNA extraction or into 10% formalin for hematoxylin and eosin (H&E) staining or immunohistochemical staining with purified mouse antibodies (anti-CD8 and anti-F4/80 from Biolegend, San Diego, CA).

Quantitative real-time PCR. RNA (<2 μg per sample) was converted into cDNA with the high-capacity first-strand cDNA Kit (Qiagen). Real-time PCR was performed on a StepOne Plus Real-time PCR system (Applied Biosystem, Carlsbad, CA). QPCR primer paires were purchased from Integrated DNA technologies (Coralville, Iowa).

CD8 T cell depletion in tumor model. InVivoPlus anti-mouse CD8α (Clone 53-6.7), purchased from BioXcell, was injected via intraperitoneal route (250 μg per injection) in mice the day before tumor implantation. A second injection was performed after 7 days with the same dose. To analyze the effect of CD8 depletion, ear tumor-inoculated mice were euthanized three days after the first administration. Cervical draining lymph nodes were collected and cell suspension was isolated for flow cytometry analysis that included staining with FITC-anti-CD8 (a different clone 5H10-1, Biolegend, San Diego, CA).

Flow cytometry for mouse ear tissues, lymph nodes, and spleens. Anti-mouse CD45 (clone 30-F11), CD11b (M1/70), F4/80 (BM8), Ly6G (1A8), Ly6C (HK1.4), IFN-γ(XMG1.2) and CD8 (5H10-1) Abs were purchased from BioLegend (San Diego, CA). Ears or tumor tissues were digested to obtain skin cell suspensions as described [30]. Lymph nodes or spleens were directly minced and filtered through cell strainers with 100 μm micron pores (Thermo Fisher Scientific, Waltham, MA). Red blood cells in the spleen samples were removed by RBC lysis buffer (BioLegend). Intracellular staining was done after incubating cells for 4 h with brefeldin A and PMA/ionomycin as described. Flow cytometry was performed using an Acuri C6 or LSR II (BD Biosciences, San Jose, CA) in conjunction with FlowJo analysis software (Tree Star, San Carlos, CA).

Statistical analysis. All data are expressed as mean±SEM. Data were analyzed using GraphPad Prism version 6 (GraphPad Software, San Diego, CA). Simple comparisons of means and SEM of data were made by using a two-sided Student t test. A p value <0.05 was considered statistically significant.

Example 1: A Small Molecule CCR2 Antagonist Depletes Tumor Macrophages and Stimulates CD8 T Cell Accumulation in a Murine Model of Cutaneous T Cell Lymphoma (CTCL) (Summary)

Tumor-associated macrophages (TAMs) recruited from blood monocytes have been implicated to play a critical role in establishing an immunosuppressive tumor microenvironment (TME) that supports tumor growth. We have reported the establishment of high grade skin T cell lymphoma in syngeneic mouse skin by injection of MBL2 T lymphoma cells in ear skin followed by application of DNFB. In this model, macrophages play a key role in sustaining tumor growth. Thus, we hypothesize that blocking monocyte trafficking (through inhibition of specific chemokine receptors) into skin can influence tumor development. Herein, we examine the effects of oral administration of a small molecule drug, Compound 1, that blocks CCR2-mediated chemotaxis of monocytes in this tumor model. Following Compound 1 administration for two days after tumor initiation, we measured (by flow cytometry) a marked depletion of macrophages in the skin (17.7% of total leukocytes vs. 2.78% in vehicle—and Compound 1-treated mice, respectively). One week after treatment, neutrophilic abscesses and epidermal ulceration occurred at the tumor site of Compound 1-, but not vehicle-treated, mice. Flow cytometry identified significantly larger numbers of neutrophils in the TME following Compound 1 treatment. At two weeks, most of the mice in control group were euthanized because of large tumors. However, Compound 1-treated tumors were smaller and sometimes nearly eradicated because of an intense inflammatory response comprised of significantly larger numbers of CD8+ T cells within the tumor (identified by immunohistochemistry). In summary, our data show a marked reduction of tumoral macrophage accumulation in Compound 1-treated mice accompanied in many animals by a reduction in tumor size and an increase in CD8+ T cells in the TME. We suggest that a therapeutic strategy for CTCL based on inhibition of the CCR2 receptor and regulation of the tumor microenvironment warrants further exploration.

Example 2: Compound 1, a CCR2 Antagonist, Inhibited Tumor Progression in a Mouse Model of Skin T Cell Lymphoma We have previously reported an inflammation-dependent mouse T cell lymphoma model that was generated by implantation of MBL2 cells in subcutaneous skin followed by a single topical application of 2,4-Dinitro-1-fluorobenzene (DNFB) in the ears. Implantation of MBL2 cells alone in the subcutaneous ears, though in syngeneic mice, does not result in tumor formation, presumably because the inflammation triggered by DNFB is often required for efficient tumor formation. However, when mice are applied a single dose of DNFB, a well-studied contact allergen, on the dorsal skin immediately following tumor cell implantation, the resultant tumor microenvironments (TME) allows reproducible tumor generation in two weeks. The application of DNFB induces large amount of inflammatory cells infiltrating in the TME, which contains mainly myeloid cell populations, i.e. macrophages and neutrophils. By inducing macrophage "suicide" using clodronate liposomes, we have shown that the macrophages in the MBL2/DNFB model contribute to tumor growth [29]. Therefore, we hypothesize that compounds targeting the chemokine receptor CCR2 for blocking monocytes recruitment and macrophage differentiation in the TME would also potentially reduce growth of T cell lymphoma tumors in the skin.

Compound 1 is an orally-bioavailable CCR2 antagonist. After being administered with two different doses, 20 mg/kg or 60 mg/kg, through daily oral gavage, plasma concentration of Compound 1 in mice correlated well to the feeding doses (FIG. 2A). In addition, neither of the dosing schemes resulted in significant (>20%) weight changes in the mice (FIG. 2B), suggesting that the drug was well tolerated. For the experimental treatment regimen, we administered Compound 1 daily via oral gavage, starting on the same day of tumor implantation (FIG. 1*a*). Ear tumors in the mice treated with two different doses of Compound 1, but not the vehicle treated mice, showed visible reduction in tumor growth (FIG. 1C). Both ear thickness and ear weight (measured immediately after euthanasia) were significantly reduced with Compound 1 treatment compared to either the untreated group or vehicle-treated control (FIG. 1C). Thus, Compound 1 blocked tumor growth in an inflammation and macrophages dependent model of T cell lymphoma.

Figure 3A:
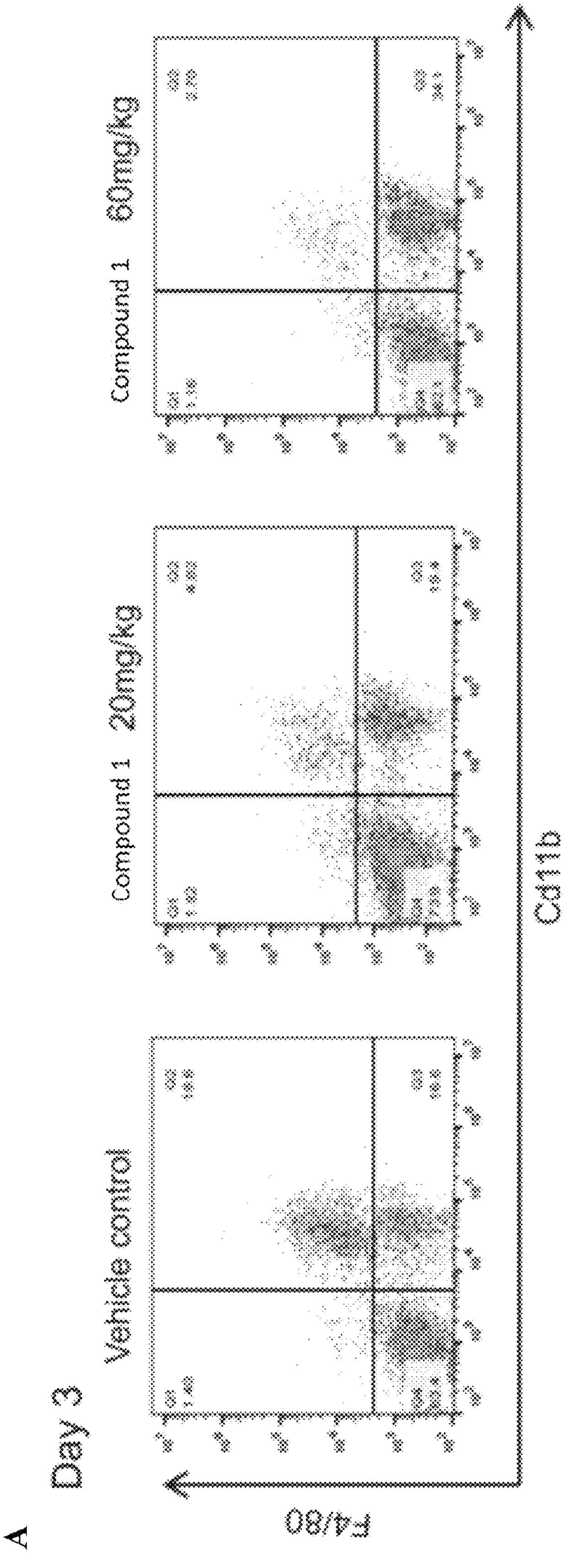
FIG. 3A-C. Compound 1 specifically targets macrophages, but not neutrophils. (A, B) Macrophages, defined by the CD11b+/F4/80+ cell populations in flow analysis, were presented in either percentage or absolute numbers in ear TME after only two daily doses of Compound 1 (dosages are indicated in the figure, * $p<0.05$, ** $p<0.01$ vs vehicle control). (C) Single cell suspension from the same tissues as in (A) were stained with antibodies for CD11b, F4/80, CCR2, Ly6G, and Ly6C. Cells gated on CD11b were further analyzed to differentiate the subpopulations. Solid circles indicate the cells which are targeted by Compound 1. Dotted circles circles indicate the cells which are not blocked by Compound 1.
Figure 3B:
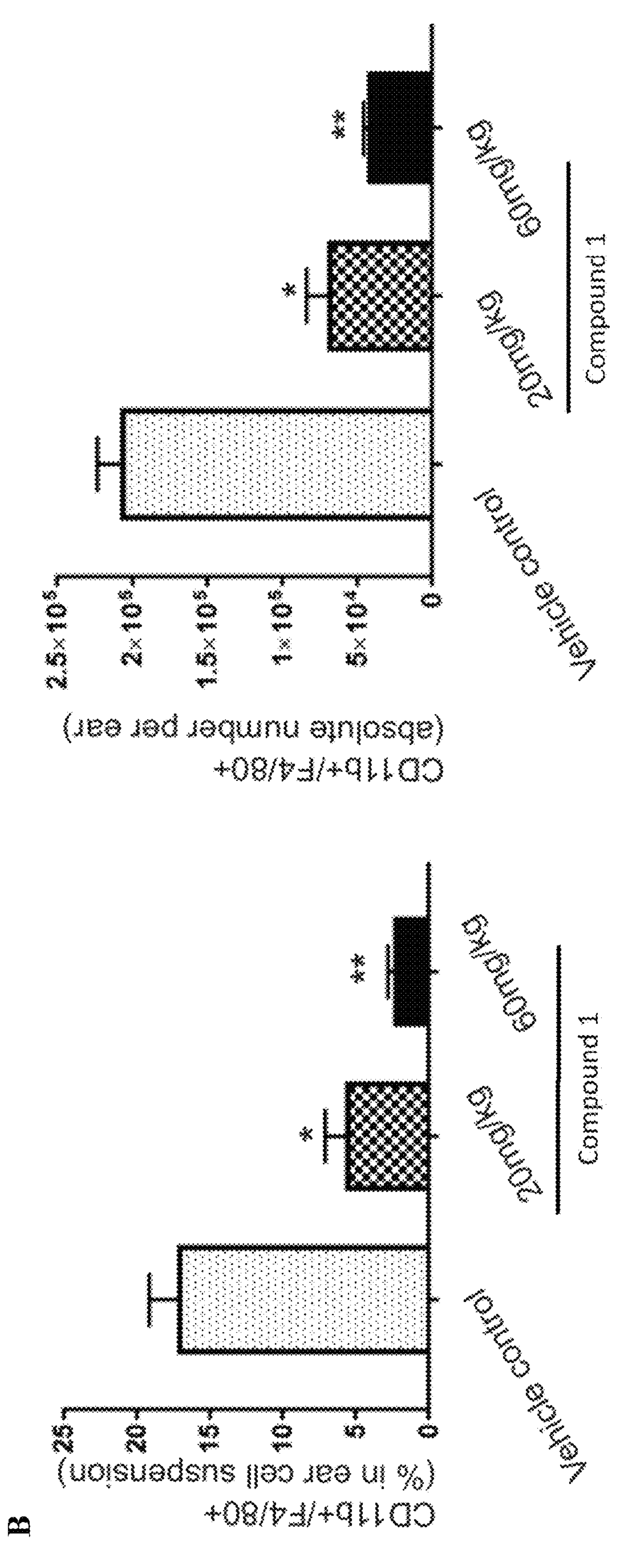

Example 3: $CCR2^+$ Macrophages are Specifically Depleted in the/Tumor Microenvironment (TME) after Compound 1 Treatment As we have previously shown, DNFB induces an inflammatory TME in the ear skin in the MBL2/DNFB model, i.e. ears exhibit redness, edema, and rapid accumulation of large numbers of inflammatory cells in just two days [28]. In order to reveal the mechanisms by which Compound 1 reduces tumor growth in mice, we examined mice that were treated with Compound 1 for two days after tumor implantation. Flow cytometry analysis of cell suspension from the ear tumors showed that levels of $CD11b^+/F4/80^+$ macrophages were significantly decreased by the Compound 1 treatment, which included both percentage values of live cells and absolute numbers by calculation in whole ears (FIGS. 3A & B). Since both flow data and tumor measurement indicated that the higher dosage of Compound 1 generated better treatment outcomes without side effects, we used 60 mg/kg per day as a standard dosage in subsequent experiments.

Figure 3C:
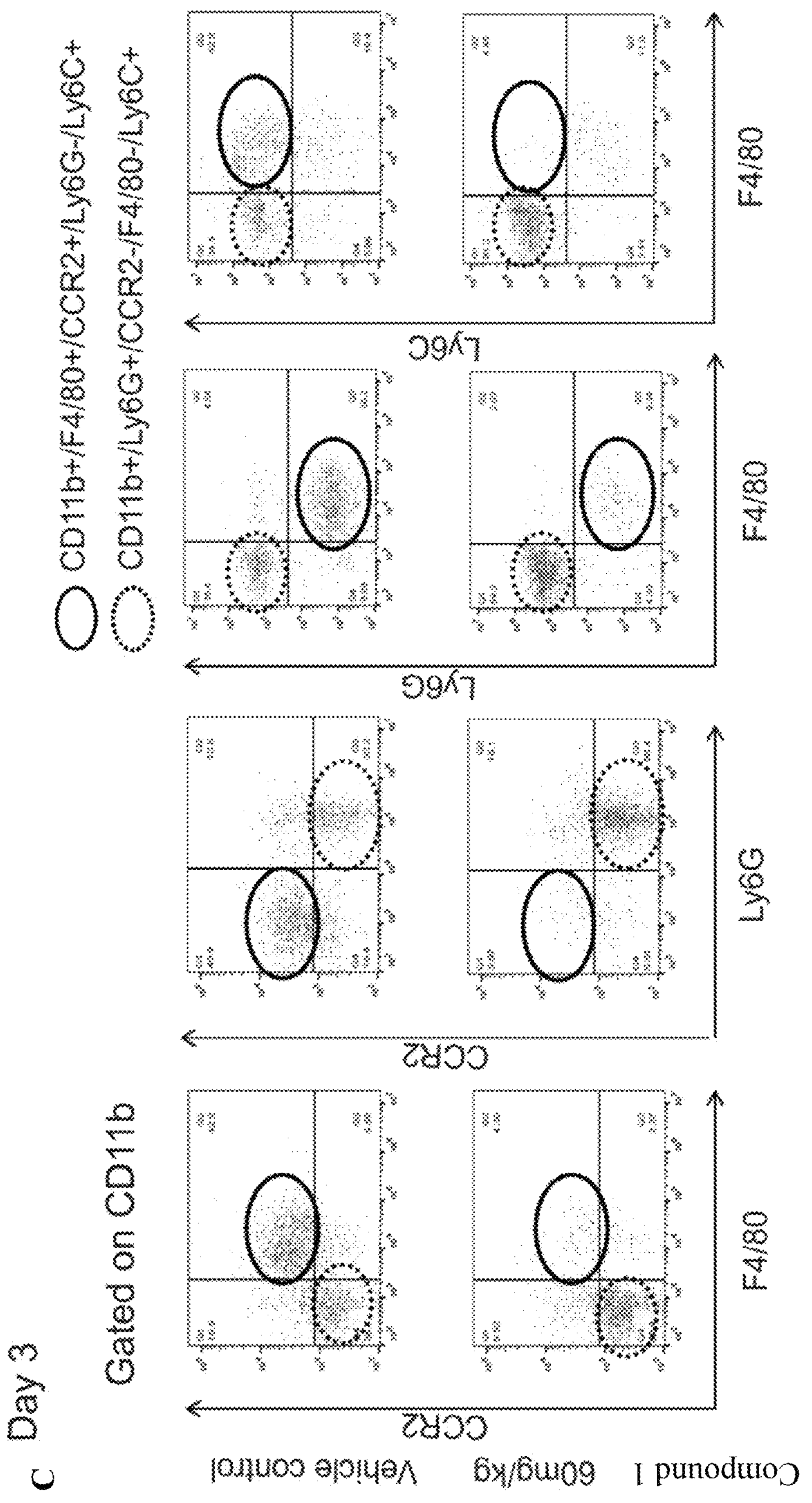

It is known that other myeloid-derived subpopulations that are closely related to macrophages in terms of immune function accumulate in the TME. We wondered if Compound 1 specifically targets the CD11b and F4/80 positive macrophages detected above. Combining the surface markers, i.e. CD11b, F4/80, Ly6G, Ly6C and CCR2, by flow cytometry on single cell suspension from the whole ear tissues, we saw that there were clearly two types of cells that dominated the myeloid cell population gated on CD11b (FIG. 3C). F4/80 positive cells, however, are the cell type that is targeted by Compound 1. This population co-expresses Ly6C and CCR2, the functional target of Compound 1. The other major cell population is comprised of CD11b- and Ly6G-positive cells, which also co-express Ly6C, but not CCR2 (FIG. 3C). Although these cells show neutrophil markers, we call them neutrophil-like cells because of their potentially immature nature and features similar to MDSCs (myeloid-derived suppressor cells) in the setting of the tumor microenvironment. As shown in FIG. 3C, accumulation of neutrophils was not blocked by Compound 1; on the contrary, their relative abundance increased because of the depletion of macrophages by CCR2 antagonism.

Example 4: Compound 1 Treatment Enhances Intratumoral Inflammation

Figure 4A:
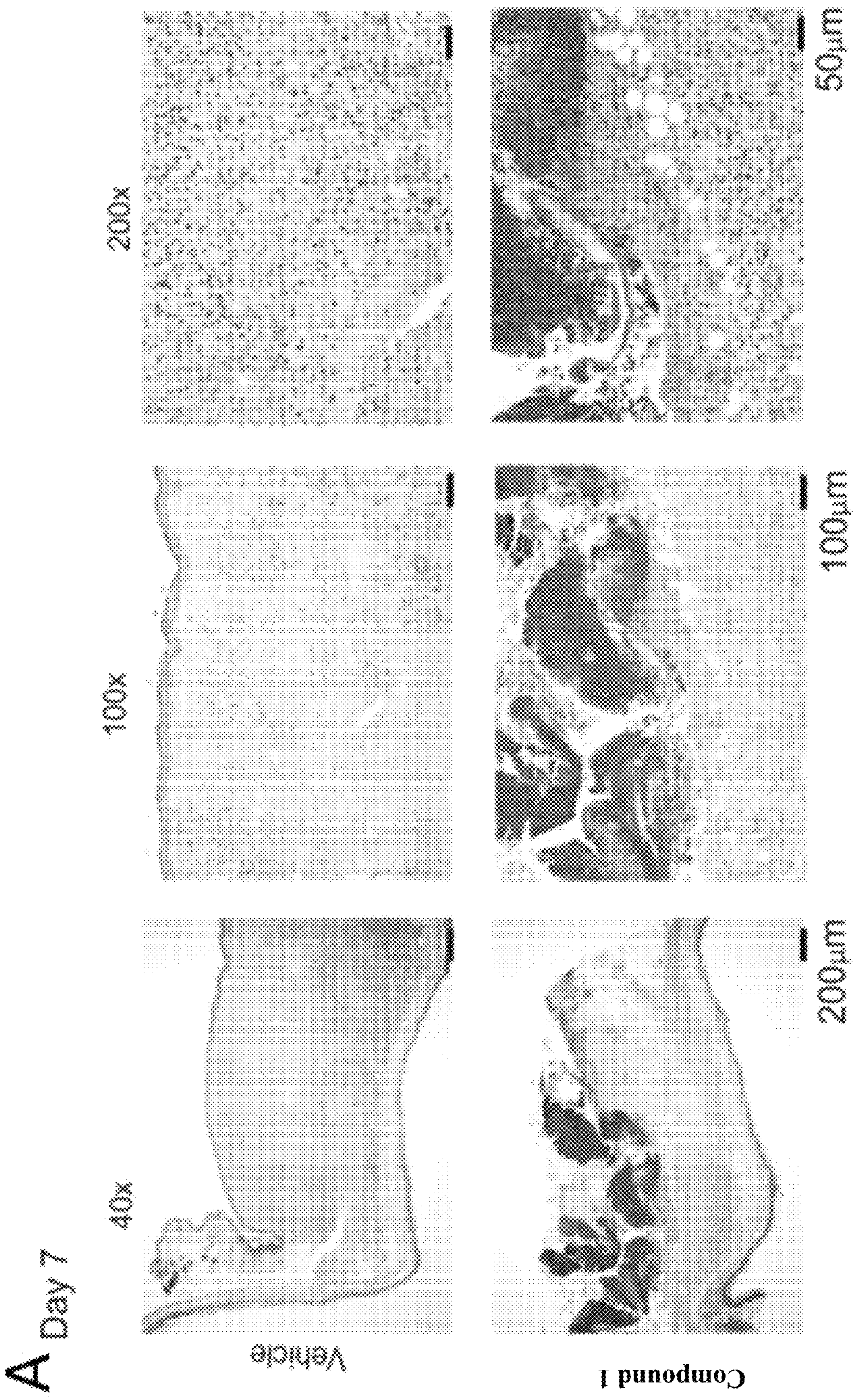

During tumor formation, the mice treated with Compound 1 showed significantly enhanced skin inflammation in the ears, which were redder and scalier than the control mice. Histological examination of tissues from day 7 revealed that ear surfaces on the dorsal side, i.e. DNFB-exposed side, exhibited surface ulceration, scaling, and obvious accumulation of inflammatory infiltrates microscopically (FIG. 4A). IHC staining with anti-F4/80 confirmed that macrophages were largely absent in the TME (FIG. 4B). Flow cytometry analysis on the tissues from the same time point showed a significant increase of neutrophil-like cells, which is consistent with histological manifestation (FIG. 4C). Of note, not only did the percentage increase, but also the total numbers increased, indicating that neutrophil-like cells were recruited to the TME accompanying the macrophage depletion. Thus, treatment with Compound 1 results in tumor cell necrosis and an increase in neutrophil-like cells in a TME that possesses low numbers of F4/80+ macrophages.

Figure 5C:
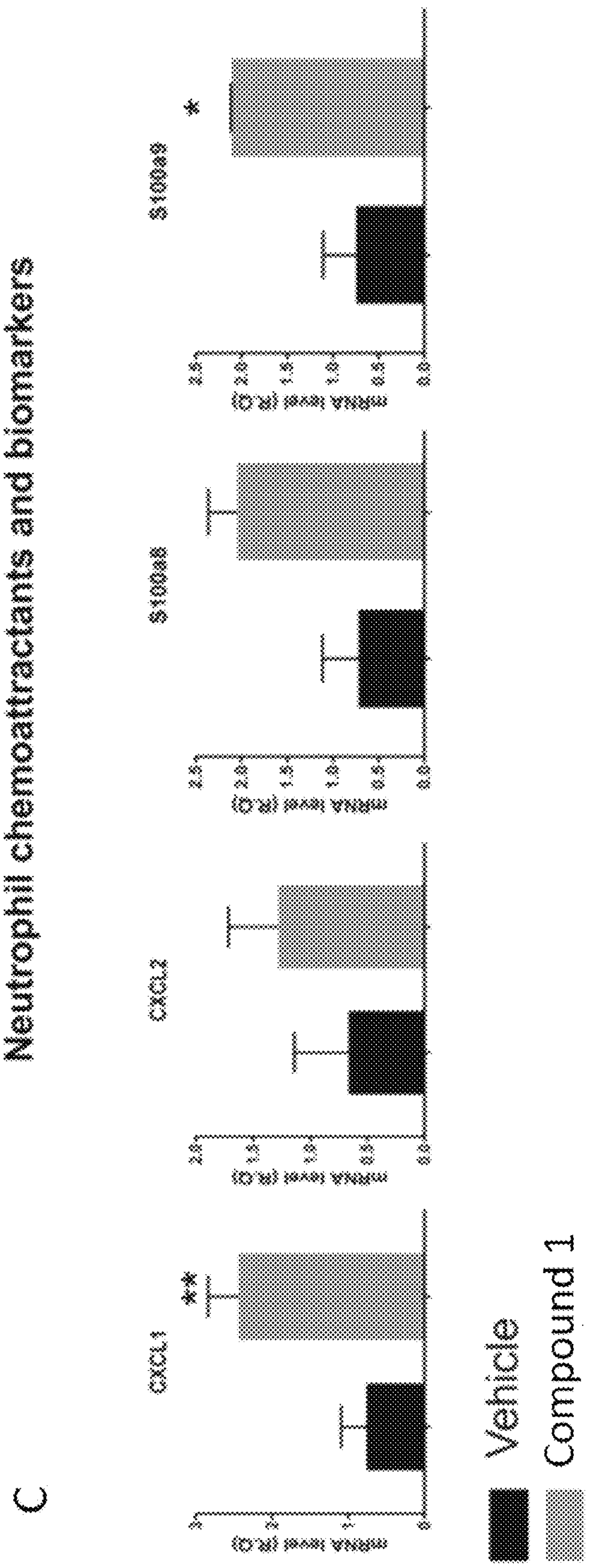
Figure 6:
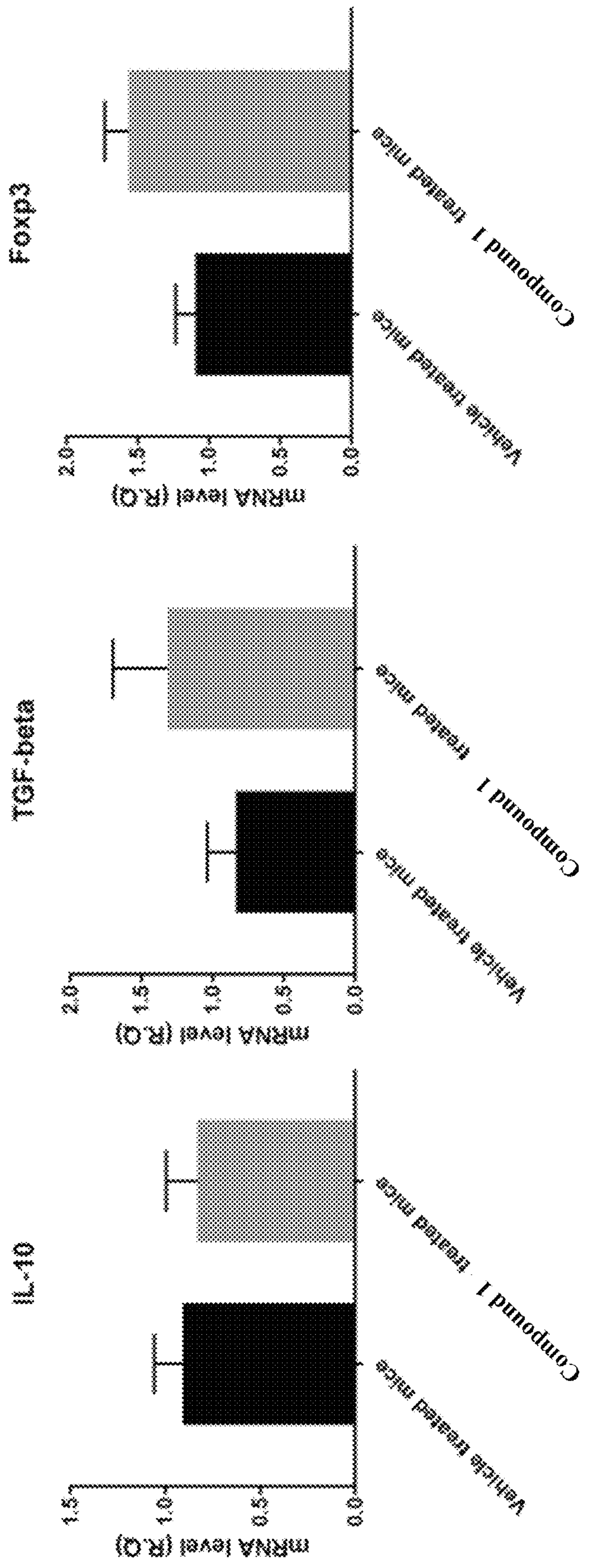
FIG. 6. Compound 1 treatment altered the expression of cytokines and biomarkers produced from the TME. Quantitative RT-PCR was performed for the ear tissues collected on day 7. Genes that are involved in immune suppression and anti-inflammation are selectively detected. Comparative expression is performed between the Compound 1 and vehicle treated groups. Gene expression values are normalized to endogenous expression of GAPDH (n=3 mice per group).

Example 5: Compound 1 Treatment Alters Cytokine and Immune Biomarkers in the TME To further understand mechanisms underlying Compound 1-mediated tumor inhibition, we quantified cytokines and chemokines known to be involved in anti-tumor immunity in Compound 1-treated tumors. Of interest, IFN-γ, IFN-γ-induced chemokines, CXCL10 and CXCL11 were all significantly increased in ears at the mRNA level by treatment with Compound 1. IL-12, another Th1 marker, was found to increase in Compound 1-treated mouse ears. We saw a consistent upregulation of granzyme B, another indication of activation of anti-tumor cytotoxic pathways (FIG. 5A). By contrast, expression of IL-10 and TGF-beta, representative Th2 cytokines, were similarly expressed between Compound 1-treated mice and controls (FIG. 6).

Additional analysis of gene expression showed that several major inflammatory cytokines, such as IL-17a, IL-1beta, and IL-6 were upregulated to variable extents in Compound 1-treated mice. Upregulation of CCL2, the ligand of CCR2, and its closely related chemokine CCL7, during CCR2 antagonism in the TME may reflect enhanced transcription of CCL2 in the setting of effective CCR2 inhibition (FIG. 5B). The last group of biomarkers noticeably increased in the TME after Compound 1 treatment are recognized neutrophil chemoattractants and biomakers, i.e. CXCL1/2 and S100A8/9 (FIG. 5C), which is consistent with the recruitment of neutrophil-like cells as shown by flow cytometry (FIG. 4C).

Figure 7A:
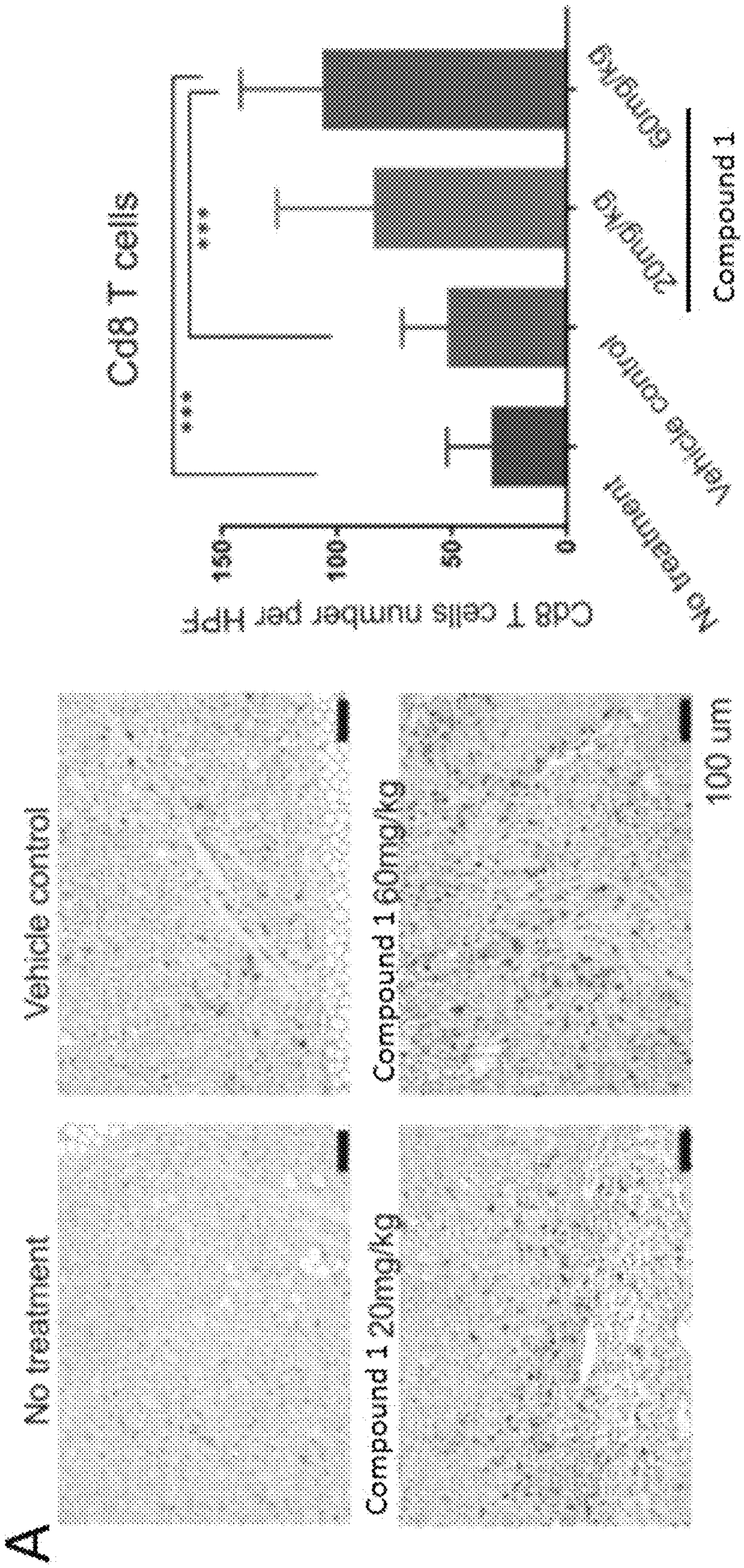

Example 6: CD8 T Cells Mediate the Anti-Tumor Activities Following Macrophage Blockade in the TME We next asked if CD8 T cells were required for Compound 1 to effectively block tumor growth. The tumor tissues were collected from tumor bearing mice receiving two weeks of treatment. Few CD8 T cells were observed in untreated and vehicle treated tumors by IHC staining (FIG. 7A). Compound 1 treatment, however, markedly increased the numbers of $CD8^+$ T cells infiltration in the TME in a dose-dependent manner (FIG. 7A).

Figure 7B:
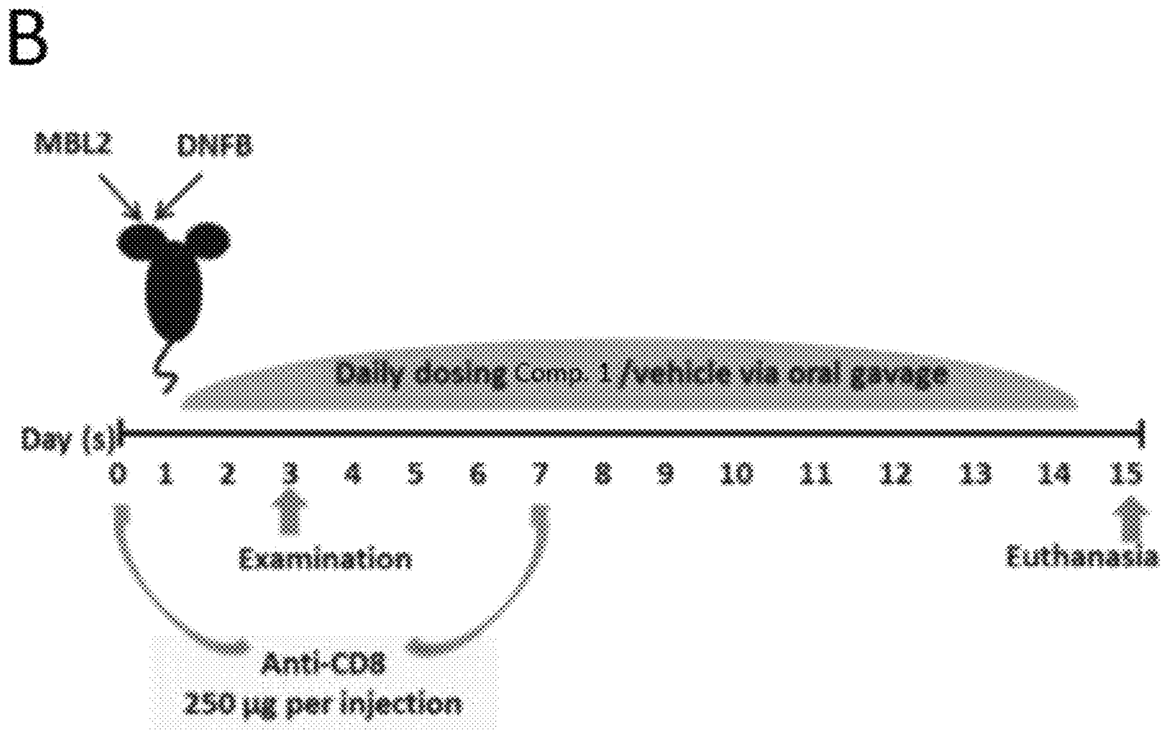
Figure 7C:
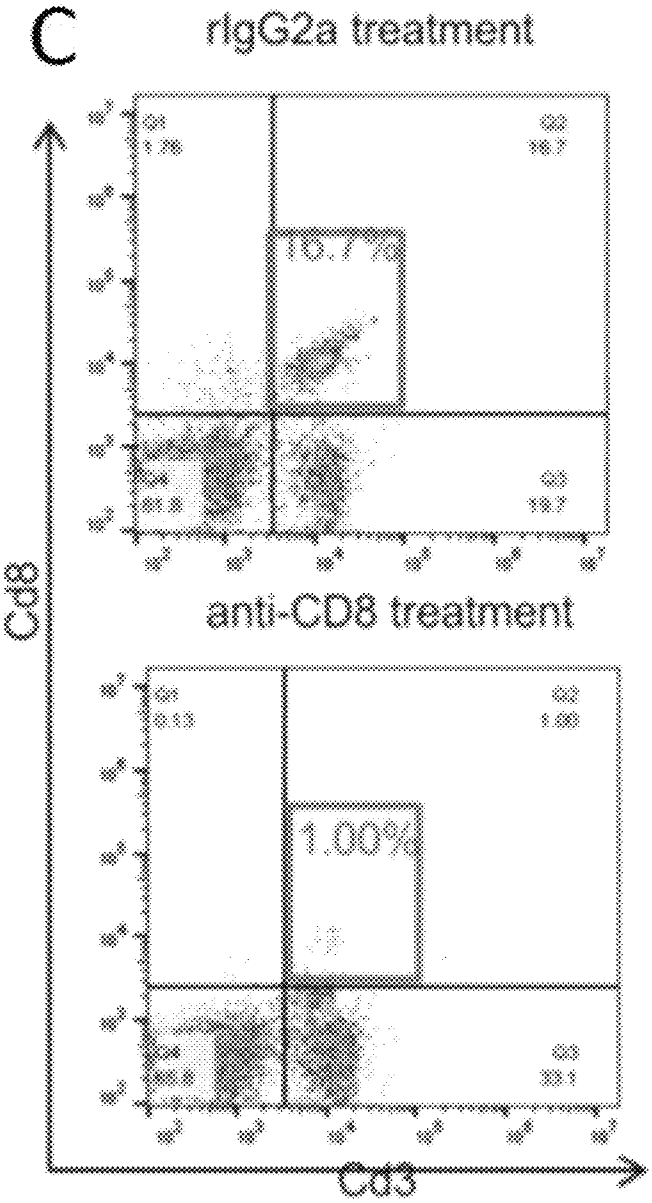

Next, we administrated neutralizing CD8 antibodies by IP injection concurrently with the Compound 1 treatment (FIG. 7B). Three days after the first injection of depleting anti-CD8 antibodies, we saw that CD3+/CD8+ T cells were virtually absent in the cervical draining lymph nodes in the antibody-treated mice (FIG. 7C). Two weeks after anti-CD8 treatment, measurement of the ear tumor size at the endpoint showed again that Compound 1-treatment inhibited tumor growth as indicated (outlined green triangles), whereas anti-CD8 abrogated this effect (similar to the levels of the vehicle treated groups) (FIG. 7D). In the DNFB-MBL2 model, the size of the ipsilateral cervical draining lymph nodes correlated well with nodal metastasis. As shown in FIG. 7E, reduction of cervical LN size with Compound 1 treatment was reversed by CD8 T cells depletion. Thus, Compound 1 treatment requires the presence of CD8+ T cells for effective reduction of tumor growth as well as LN metastasis.

Example 7: Macrophage Blockade Synergizes With Anti-PD1 in Constraining MBL2 Tumor Growth The role of PD1 in cancer immune evasion is well established in so far as tumor cells or antigen-presenting cells, such as macrophages, express PD-L1 and interact with PD-1 positive CD8-T cells to render them anergic with respect to antitumor activity. Thus, inhibitors blocking the interaction between PD-1 and PD-L1 can enhance T-cell responses, known as immune checkpoint blockade. Compared to the cultured MBL2 cells in vitro, MBL2 tumor formed in mice exhibited a significant increase of PD-L1 (FIG. 8A). Similar to results with Compound 1, antibody blockade of PD-1/PD-L1 axis in this MBL2 model could effectively delay the tumor growth, but was unable to eliminate the tumors (FIG. 9A-B). This prompted us to apply combination therapy over a single agent in order to achieve better anti-tumor effects.

Figure 8C:
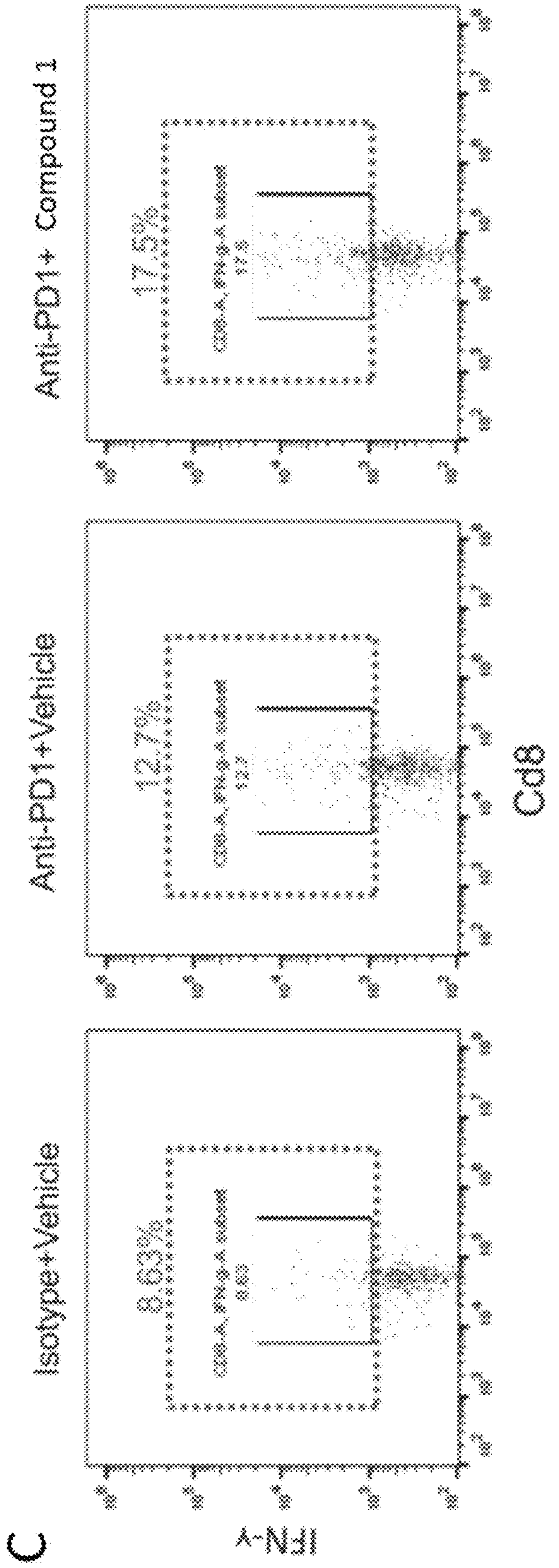
Figure 8D:
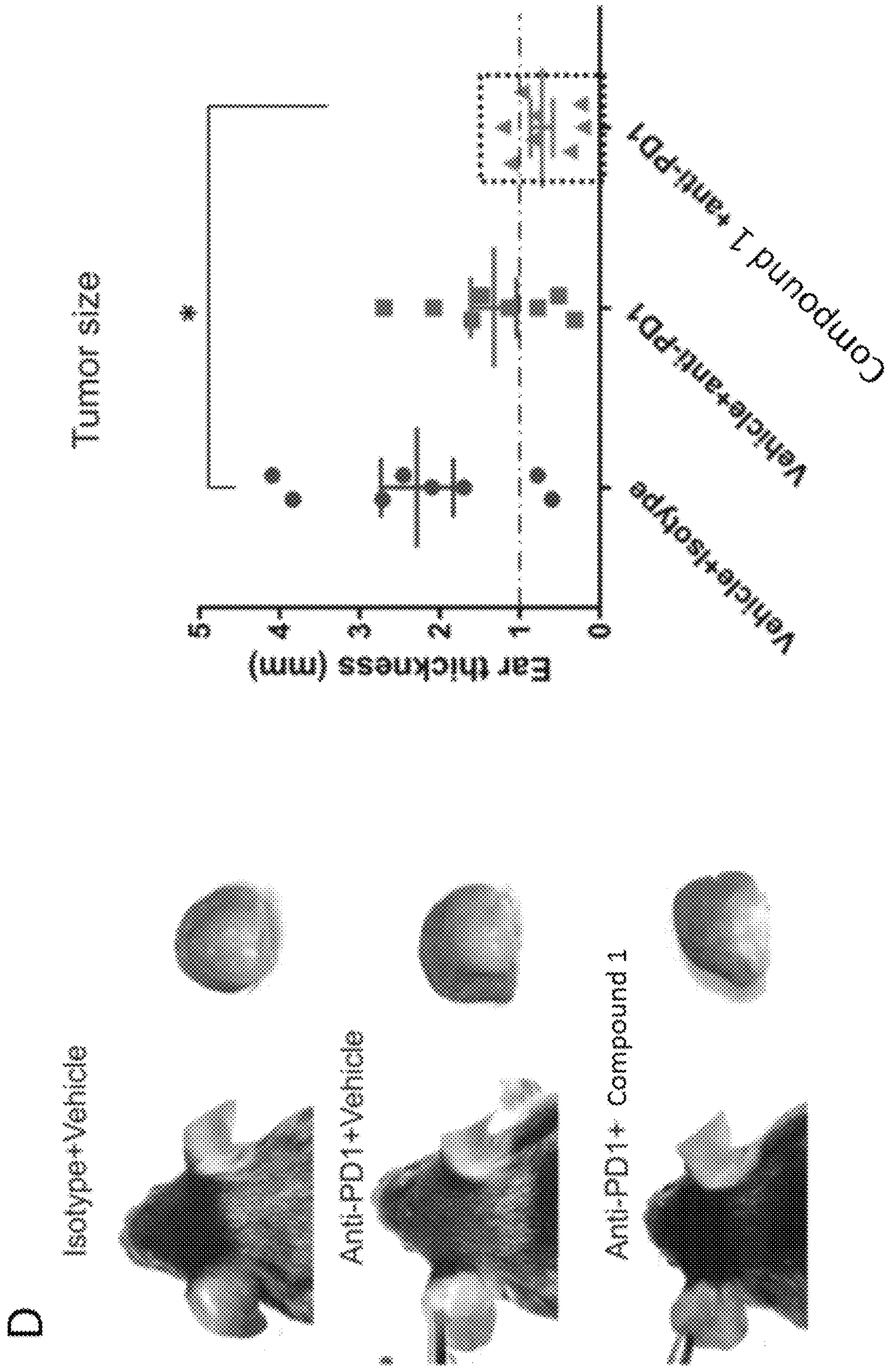

For the combination therapy, mice were treated with anti-PD1 at 10 mg/kg every other day beginning on the same day of the first Compound 1 treatment and tumor implantation (FIG. 8B). When mice were euthanized after completing the two weeks treatment, we analyzed the spleens in each group and found that the number of IFN-γ-producing CD8-T cells significantly increased in the group treated with the combination of Compound 1 and anti-PD1, suggesting these mice exhibit more robust anti-tumor immunity (FIG. 8C). In examining the size of ear tumors, we found that the combination therapy, but not the anti-PD1 and vehicle treatment, significantly inhibited the ear tumor growth compared to the control group treated with isotype and vehicle. According to our past observations of the MBL2/DNFB model for extended time periods, i.e. over 6 weeks after tumor implantation, mice with an ear thickness less than 1 mm at two weeks rarely, if ever, develop tumors. As shown by the horizontal dotted line in the graph, nearly 75% of the mice from combined treatment group had a tumor thickness less than 1 mm, suggestive of long term tumor clearance (FIG. 8D).

REFERENCES

1. Grivennikov S I, Greten F R, Karin M: Immunity, inflammation, and cancer. *Cell* 2010, 140:883-899.
2. Franklin R A, Liao W, Sarkar A, Kim M V, Bivona M R, Liu K, Pamer E G, Li MO: The cellular and molecular origin of tumor-associated macrophages. *Science* 2014, 344:921-925.
3. Yang L, Zhang Y: Tumor-associated macrophages: from basic research to clinical application. *J Hematol Oncol* 2017, 10:58.
4. Fujimura T, Kambayashi Y, Fujisawa Y, Hidaka T, Aiba S: Tumor-Associated Macrophages: Therapeutic Targets for Skin Cancer. *Front Oncol* 2018, 8:3.
5. Fujimura T, Ring S, Umansky V, Mahnke K, Enk A H: Regulatory T cells stimulate B7-H1 expression in myeloid-derived suppressor cells in ret melanomas. *J Invest Dermatol* 2012, 132:1239-1246.
6. Pedersen M B, Danielsen A V, Hamilton-Dutoit S J, Bendix K, Norgaard P, Moller M B, Steiniche T, d'Amore F: High intratumoral macrophage content is an adverse prognostic feature in anaplastic large cell lymphoma. *Histopathology* 2014, 65:490-500.
7. Tang X, Mo C, Wang Y, Wei D, Xiao H: Anti-tumour strategies aiming to target tumour-associated macrophages. *Immunology* 2013, 138:93-104.
8. Cheung K J, Johnson N A, Affleck J G, Severson T, Steidl C, Ben-Neriah S, Schein J, Morin R D, Moore R, Shah S P, et al: Acquired TNFRSF14 mutations in follicular lymphoma are associated with worse prognosis. *Cancer Res* 2010, 70:9166-9174.
9. Stanley E R, Chitu V: CSF-1 receptor signaling in myeloid cells. *Cold Spring Harb Perspect Biol* 2014, 6.
10. Papadopoulos K P, Gluck L, Martin L P, Olszanski A J, Tolcher A W, Ngarmchamnanrith G, Rasmussen E, Amore B M, Nagorsen D, Hill J S, Stephenson J, Jr.: First-in-Human Study of AMG 820, a Monoclonal Anti-Colony-Stimulating Factor 1 Receptor Antibody, in Patients with Advanced Solid Tumors. *Clin Cancer Res* 2017, 23:5703-5710.

11. Cannarile M A, Weisser M, Jacob W, Jegg A M, Ries C H, Ruttinger D: Colony-stimulating factor 1 receptor (CSF1R) inhibitors in cancer therapy. *J Immunother Cancer* 2017, 5:53.
12. Quail D F, Bowman R L, Akkari L, Quick M L, Schuhmacher A J, Huse J T, Holland E C, Sutton J C, Joyce J A: The tumor microenvironment underlies acquired resistance to CSF-1R inhibition in gliomas. *Science* 2016, 352:aad3018.
13. Zhang J, Patel L, Pienta K J: Targeting chemokine (C-C motif) ligand 2 (CCL2) as an example of translation of cancer molecular biology to the clinic. *Prog Mol Biol Transl Sci* 2010, 95:31-53.
14. Chen X, Wang Y, Nelson D, Tian S, Mulvey E, Patel B, Conti I, Jaen J, Rollins B J: CCL2/CCR2 Regulates the Tumor Microenvironment in HER-2/neu-Driven Mammary Carcinomas in Mice. *PLoS One* 2016, 11:e0165595.
15. Yao M, Smart C, Hu Q, Cheng N: Continuous Delivery of Neutralizing Antibodies Elevate CCL2 Levels in Mice Bearing MCF10CA1d Breast Tumor Xenografts. *Transl Oncol* 2017, 10:734-743.
16. Pienta K J, Machiels J P, Schrijvers D, Alekseev B, Shkolnik M, Crabb S J, Li S, Seetharam S, Puchalski T A, Takimoto C, et al: Phase 2 study of carlumab (CNTO 888), a human monoclonal antibody against CC-chemokine ligand 2 (CCL2), in metastatic castration-resistant prostate cancer. *Invest New Drugs* 2013, 31:760-768.
17. Sandhu S K, Papadopoulos K, Fong P C, Patnaik A, Messiou C, Olmos D, Wang G, Tromp B J, Puchalski T A, Balkwill F, et al: A first-in-human, first-in-class, phase I study of carlumab (CNTO 888), a human monoclonal antibody against CC-chemokine ligand 2 in patients with solid tumors. *Cancer Chemother Pharmacol* 2013, 71:1041-1050.
18. Lim S Y, Yuzhalin A E, Gordon-Weeks A N, Muschel R J: Targeting the CCL2-CCR2 signaling axis in cancer metastasis. *Oncotarget* 2016, 7:28697-28710.
19. Yao W, Ba Q, Li X, Li H, Zhang S, Yuan Y, Wang F, Duan X, Li J, Zhang W, Wang H: A Natural CCR2 Antagonist Relieves Tumor-associated Macrophage-mediated Immunosuppression to Produce a Therapeutic Effect for Liver Cancer. *EBioMedicine* 2017, 22:58-67.
20. Zheng Y, Qin L, Zacarias N V, de Vries H, Han G W, Gustaysson M, Dabros M, Zhao C, Cherney R J, Carter P, et al: Structure of CC chemokine receptor 2 with orthosteric and allosteric antagonists. *Nature* 2016, 540: 458-461.
21. Nywening T M, Wang-Gillam A, Sanford D E, Belt B A, Panni R Z, Cusworth B M, Toriola A T, Nieman R K, Worley L A, Yano M, et al: Targeting tumour-associated macrophages with CCR2 inhibition in combination with FOLFIRINOX in patients with borderline resectable and locally advanced pancreatic cancer: a single-centre, open-label, dose-finding, non-randomised, phase 1b trial. *Lancet Oncol* 2016, 17:651-662.
22. Roblek M, Calin M, Schlesinger M, Stan D, Zeisig R, Simionescu M, Bendas G, Borsig L: Targeted delivery of CCR2 antagonist to activated pulmonary endothelium prevents metastasis. *J Control Release* 2015, 220:341-347.
23. Hwang S T, Janik J E, Jaffe E S, Wilson W H: Mycosis fungoides and Sezary syndrome. *Lancet* 2008, 371:945-957.
24. Krejsgaard T, Lindahl L M, Mongan N P, Wasik M A, Litvinov I V, Iversen L, Langhoff E, Woetmann A, Odum N: Malignant inflammation in cutaneous T-cell lymphoma-a hostile takeover. *Semin Immunopathol* 2017, 39:269-282.
25. Wu X, Hwang S T: Cutaneous T-Cell Lymphoma: The Yin and Yang of Inflammation and Neoplasia. *J Investig Dermatol Symp Proc* 2015, 17:34-35.
26. Sugaya M, Miyagaki T, Ohmatsu H, Suga H, Kai H, Kamata M, Fujita H, Asano Y, Tada Y, Kadono T, et al: Association of the numbers of CD163(+) cells in lesional skin and serum levels of soluble CD163 with disease progression of cutaneous T cell lymphoma. *J Dermatol Sci* 2012, 68:45-51.
27. Miyagaki T, Sugaya M, Suga H, Ohmatsu H, Fujita H, Asano Y, Tada Y, Kadono T, Sato S: Increased CCL18 expression in patients with cutaneous T-cell lymphoma: association with disease severity and prognosis. *J Eur Acad Dermatol Venereol* 2013, 27:e60-67.
28. Wu X, Sells R E, Hwang S T: Upregulation of inflammatory cytokines and oncogenic signal pathways preceding tumor formation in a murine model of T-cell lymphoma in skin. *J Invest Dermatol* 2011, 131:1727-1734.
29. Wu X, Schulte B C, Zhou Y, Haribhai D, Mackinnon A C, Plaza J A, Williams C B, Hwang S T: Depletion of M2-like tumor-associated macrophages delays cutaneous T-cell lymphoma development in vivo. *J Invest Dermatol* 2014, 134:2814-2822.
30. Broggi A, Cigni C, Zanoni I, Granucci F: Preparation of Single-cell Suspensions for Cytofluorimetric Analysis from Different Mouse Skin Regions. *J Vis Exp* 2016: e52589.
31. Bonapace L, Coissieux M M, WyckoffJ, Mertz K D, Varga Z, Junt T, Bentires-Alj M: Cessation of CCL2 inhibition accelerates breast cancer metastasis by promoting angiogenesis. *Nature* 2014, 515:130-133.
32. Hitchcock J R, Watson C J: Anti-CCL2: building a reservoir or opening the floodgates to metastasis? *Breast Cancer Res* 2015, 17:68.
33. Xue C B, Wang A, Han Q, Zhang Y, Cao G, Feng H, Huang T, Zheng C, Xia M, Zhang K, et al: Discovery of INCB8761/PF-4136309, a Potent, Selective, and Orally Bioavailable CCR2 Antagonist. *ACS Med Chem Lett* 2011, 2:913-918.
34. Wein L, Savas P, Luen S J, Virassamy B, Salgado R, Loi S: Clinical Validity and Utility of Tumor-Infiltrating Lymphocytes in Routine Clinical Practice for Breast Cancer Patients: Current and Future Directions. *Front Oncol* 2017, 7:156.
35. Cohen I J, Blasberg R: Impact of the Tumor Microenvironment on Tumor-Infiltrating Lymphocytes: Focus on Breast Cancer. *Breast Cancer* (*Auckl*) 2017, 11:1178223417731565.
36. Peranzoni E, Lemoine J, Vimeux L, Feuillet V, Barrin S, Kantari-Mimoun C, Bercovici N, Guerin M, Biton J, Ouakrim H, et al: Macrophages impede CD8 T cells from reaching tumor cells and limit the efficacy of anti-PD-1 treatment. *Proc Natl Acad Sci* USA 2018, 115:E4041-E4050.
37. Ahmadzadeh M, Johnson L A, Heemskerk B, Wunderlich J R, Dudley M E, White D E, Rosenberg S A: Tumor antigen-specific CD8 T cells infiltrating the tumor express high levels of PD-1 and are functionally impaired. *Blood* 2009, 114:1537-1544.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating cutaneous T cell lymphoma (CTCL), said method comprising administering to a subject in need thereof an effective amount of a Chemokine Receptor 2 (CCR2) antagonist, wherein said CCR2 antagonist is a pharmaceutically acceptable salt of a compound selected from the group consisting of

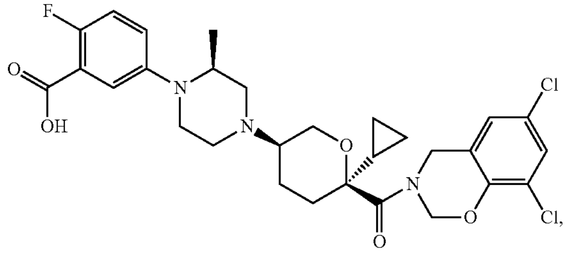

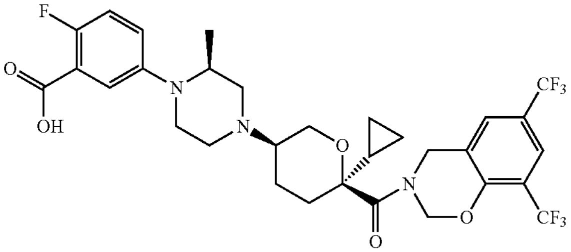

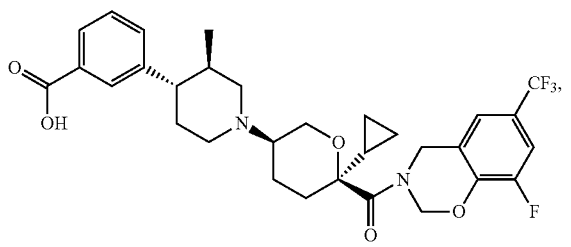

and

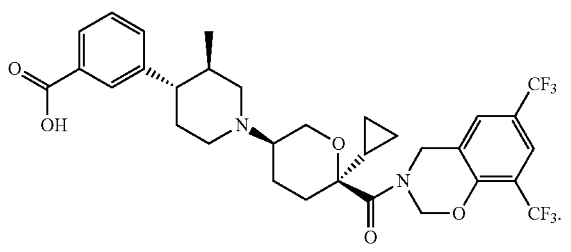

2. The method of claim 1, wherein said CCR2 antagonist is a pharmaceutically acceptable salt of a compound having the formula of Compound 1

(Compound 1)

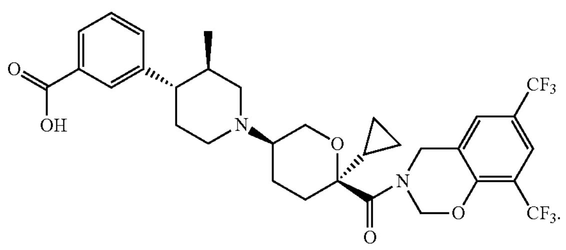

3. The method of claim 1, wherein said CCR2 antagonist is a pharmaceutically acceptable salt of a compound having the formula of Compound 2

(Compound 2)

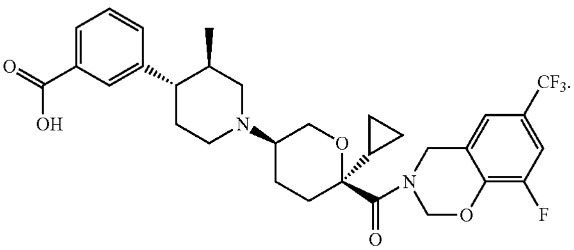

4. The method of claim 1, further comprising administering one or more additional therapeutic agents.

5. The method of claim 4, wherein the one or more additional therapeutic agents is an immune-checkpoint inhibitor.

6. The method of claim 5, wherein the immune-checkpoint inhibitor is a PD-1 and/or PD-L1 inhibitor.

7. The method of claim 6, wherein the PD-1 and/or PD-L1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

8. The method of claim 6, wherein the PD-1 and/or PD-L1 inhibitor is selected from the group consisting of nivolumab, pembrolizumab, and pidilizumab.

9. The method of claim 6, wherein the PD-1 and/or PD-L1 inhibitor is selected from the group consisting of durvalumab, atezolizumab, avelumab, BMS-936559, ALN-PDL, TSR-042, KD-033, CA-170, CA-327, STI-1014, and KY-1003.

10. A method of treating cutaneous T cell lymphoma (CTCL), said method comprising administering to a subject in need thereof an effective amount of a Chemokine Receptor 2 (CCR2) antagonist, wherein said CCR2 antagonist is a compound selected from the group consisting of

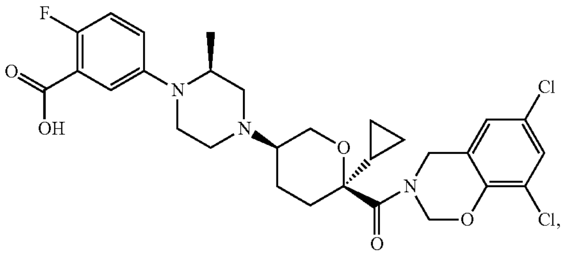

-continued

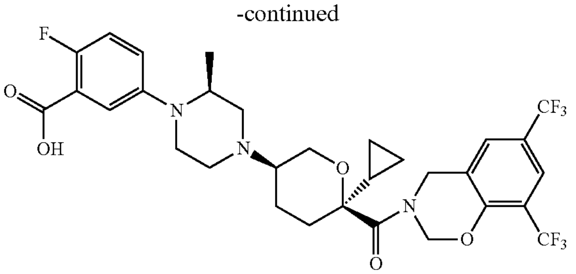

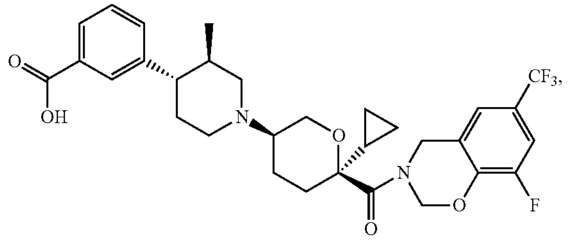

and

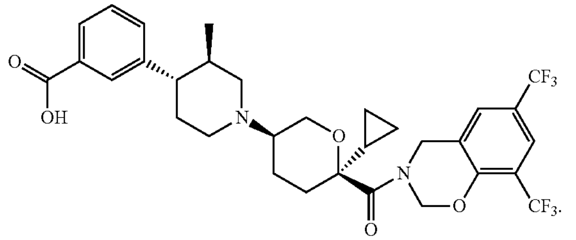

11. The method of claim 10, wherein said CCR2 antagonist is a compound having the formula of Compound 1

(Compound 1)

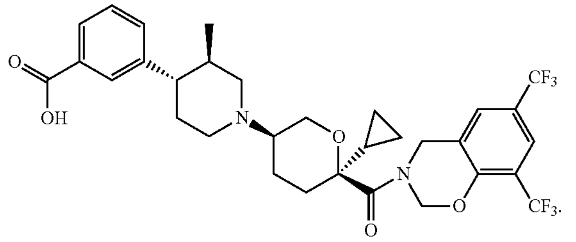

12. The method of claim 10, wherein said CCR2 antagonist is a compound having the formula of Compound 2

(Compound 2)

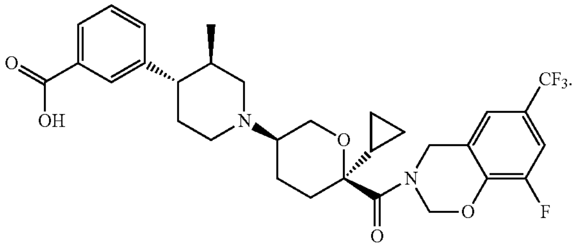

13. The method of claim 10, further comprising administering one or more additional therapeutic agents.

14. The method of claim 13, wherein the one or more additional therapeutic agents is an immune-checkpoint inhibitor.

15. The method of claim 14, wherein the immune-checkpoint inhibitor is a PD-1 and/or PD-L1 inhibitor.

16. The method of claim 15, wherein the PD-1 and/or PD-L1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

17. The method of claim 15, wherein the PD-1 and/or PD-L1 inhibitor is selected from the group consisting of nivolumab, pembrolizumab, and pidilizumab.

18. The method of claim 15, wherein the PD-1 and/or PD-L1 inhibitor is selected from the group consisting of durvalumab, atezolizumab, avelumab, BMS-936559, ALN-PDL, TSR-042, KD-033, CA-170, CA-327, STI-1014, and KY-1003.

* * * * *